(12) United States Patent
van Peij et al.

(10) Patent No.: US 8,642,290 B2
(45) Date of Patent: Feb. 4, 2014

(54) FUNGAL TRANSCRIPTIONAL ACTIVATORS USEFUL IN METHODS FOR PRODUCING A POLYPEPTIDE

(75) Inventors: Noël Nicolaas Maria Elisabeth van Peij, Delft (NL); Lucie Parenicova, Den Haag (NL)

(73) Assignee: DSM IP Assets B.V., Heerlen (NL)

( * ) Notice: Subject to any disclaimer, the term of this patent is extended or adjusted under 35 U.S.C. 154(b) by 240 days.

(21) Appl. No.: 12/801,954

(22) Filed: Jul. 2, 2010

(65) Prior Publication Data
US 2011/0165656 A1 Jul. 7, 2011

Related U.S. Application Data

(62) Division of application No. 11/664,291, filed as application No. PCT/EP2005/055145 on Oct. 11, 2005, now Pat. No. 7,794,974.

(30) Foreign Application Priority Data
Oct. 12, 2004 (EP) .................................... 04105001

(51) Int. Cl.
*C12P 21/06* (2006.01)
*C07H 21/02* (2006.01)
*C07K 14/00* (2006.01)

(52) U.S. Cl.
USPC ......................... 435/69.1; 536/23.1; 530/350

(58) Field of Classification Search
USPC ......................... 435/69.1; 536/23.1; 530/350
See application file for complete search history.

(56) References Cited

U.S. PATENT DOCUMENTS 6,806,062 B1 10/2004 Hjort et al.
7,303,877 B2 12/2007 Connelly et al.
7,794,974 B2 * 9/2010 Peij et al. ..................... 435/69.1

FOREIGN PATENT DOCUMENTS

WO  WO 00/20596   4/2000
WO  WO 01/68864   9/2001

OTHER PUBLICATIONS

Amino Acid Sequence Alignment of SEQ ID No. 3 with USP 6,806,062; Jan. 2013.*
Nucleic Acid Sequence Alignment of SEQ ID No. 2 with USP 6,806,062, Jan. 2013.*
Database EMBL "EST827069 *Aspergillus flavus* normalized cDNA expression library *Aspergillus flavus* cDNA clone NAGFG44 5' end, mRNA sequence" Accession No. EM_EST:CO152016, Database Accession No. CO152016, all pages, Jun. 19, 2004.
van den Hornbergh et al. "Production of the homologous pectin lyase B protein in six genetically defined protease-deficient *Aspergillus niger* mutant strains" Current Genetics, vol. 32, No. 1, pp. 73-81, Jul. 1997.

* cited by examiner

*Primary Examiner* — Karen Cochrane Carlson
(74) *Attorney, Agent, or Firm* — Miles & Stockbridge, P.C.

(57) ABSTRACT

The present invention relates to functional cDNA and genomic sequences encoding PrtT proteins, which are transcriptional activity on a protease promoter, to PrtT proteins and their uses. The invention further relates to two distinct types of filamentous fungal cells. Filamentous fungal cells are transformed to over-express these PrtT proteins: this type of filamentous fungus will be highly suited as protease producer. Alternatively, the endogenous prtT genes of filamentous fungal cells are inactivated: this type of filamentious fungus is highly suited for the production of any polypeptide native or not which is highly sensitive for protease degradation. The PrtT proteins of the invention provide means for identification of functional homologues in other species.

15 Claims, 19 Drawing Sheets

```
A.oryzae1: 1    MRRTTVEPIKYEAPSWEHKSVSVSDE RIIPNVGDATPFGRIERSMTACNTCRKLKT  60
                MRRTTVEPIKYEAPSWEHKSVSVSDE RIIPNVGDATPFGRIERSMTACNTCRKLKT
A.oryzae2: 1    MRRTTVEPIKYEAPSWEHKSVSVSDE RIIPNVGDATPFGRIERSSTACNTCRKLKT  60

A.oryzae1:61    PCDLPPGHACRPCLSLPIDCQLPETSRPQDSTPMWSDATTAIPSIERLTSLERSMPS  120
                PCDLPPGHACRPCLSLPIDCQLPETSRPQDSTPMWSDATTAIPSIERLTSLERSMPS
A.oryzae2:61    PCDLAPPHACRPCLSKPIDCQLPETSRRPQDSIPMWSDATTAIPSIERLISLERSNPS  120

A.oryzae1:121   STGMLRQILNQSPSVSNISVPPLARSVRTEETASIEDNSFGSFLPRPVRLIQDLQSEFPG  180
                STGMLRQILNQSPSVSNISVPPLARSVRTEETASIEDNSFGSFLPRPVRLIQDLQSEFPG
A.oryzae2:121   STGMLRQILNQSPSVSNISVPPLARSVRTEETASIEDNSFGSFLPRPVRLIQDLQSEFPG  180

A.oryzae1:181   STNRIPVSSPPLGNSPEKGILDSKLSLRLVQLFVDNPGPLVSINQSDPHNRMRNTDSLL  240
                STNRIPVSSPPLGNSPEKGILDSKLSLRLVQLFVDNPGPLVGINQSDPHNEMPNTDSLL
A.oryzae2:181   STNRIPVSSPPLGDSPEKGILDGSKLGLKLVQLFVDFGPDVSINQSOFHNEMPNTDSLL  240

A.oryzae1:241   YSTACLLASRYVPGLPPPIVETMNLQVRSKAVDLLWSSPPLKYESLQALALLCLWPAACQ  300
                YSTACLLASRYVPGLPPPIVETMNLQVRSKAVDLLWSSPPLKYESLQALALLCLWPAACQ
A.oryzae2:241   YSTACLLASRYVPGLPPPIVETMNLQVRSKAVDLLWSSPPLKYESLQALALLCLWPAACQ  300

A.oryzae1:301   KEFPIDGWLLSGTAINHALVSPDPLNRVPSELLDNDIAAQLRLWNAPCLTQLSFAVGNA  360
                KEFPIDGWLLSGTAINHALVSPDFLNHVPSELLDNDIAAQLRLWNAPCLTQLSFAVGNA
A.oryzae2:301   KEFPIDGWLLSGTAINHALVSPDFLNHVPSDLLDNDIAAQLRLWNAPCLTQLSFAVGNA  360

A.oryzae1:361   RPFRLPQRYLDYCPRLLESPAATVEDGKVYAEIQLYLITLRLQANEQRMPFASVEYEEIE  420
                RPFRLPQRYLDYCPRLLEHPAATVEDGKVYAEIQLYLITLRLQANEQRMPFASVEYEEIE
A.oryzae2:361   RPFRLPQSYLDYCPRLLEHPAATVEDGKVYAEIQLYLITLRLQANEQRMPFASVEYEEIE  420

A.oryzae1:421   PWKVEMAHLLAG                                                  480
                PWKVEMAHLLAG
A.oryzae2:421   PWKVEMAHLLAG  431

A.oryzae1:481                                                                 540

A.oryzae1:541                                                                 600

A.oryzae1:601                                         624
```

```
A.niger SEQ ID NO 02        ....P----------------SG-ES...     12aa
A.oryzae                    ....L-----------------AGDEN...    13aa
A.fumigatus                 ....L-----------------TGEQH...    13aa
P.chrysogenum               ....L-----------------TTNGD...    13aa
A.niger   WO 00/20596       ....PCKKPVLVSKGLPLIEATAG-ES...    29aa
A.oryzae WO 01/68864        ....L-----------------AG           8aa
```

Figure 18

FUNGAL TRANSCRIPTIONAL ACTIVATORS USEFUL IN METHODS FOR PRODUCING A POLYPEPTIDE

This application is a divisional of U.S. application No. 11/664,291, filed May 10, 2007 now U.S. Pat. No. 7,794,974, which is the U.S. national phase of International Application No. PCT/EP2005/055145, filed Oct. 11, 2005, which designated the U.S. and claims priority from European Application No. 04105001.4, filed Oct. 12, 2004, the entire contents of which applications are incorporated herein by reference.

FIELD OF THE INVENTION

The present invention relates to polypeptides having transcriptional activation activity on a protease promoter, to the nucleic acid sequences encoding these polypeptides and to several uses of these nucleic acid sequences.

BACKGROUND OF THE INVENTION

Fungal transcriptional activators named PrtT have been recently described in WO 00/20596 and WO 01/68864. These transcriptional activators were isolated from *Aspergillus niger* (*A. niger*) and *Aspergillus oryzae* (*A. oryzae*). These transcriptional activators of protease genes can be either used to improve a method for producing proteases in a fungal cell or to improve a method for producing a polypeptide in a fungal cell, wherein the polypeptide is sensitive for protease degradation.

The present invention provides novel PrtT fungal transcriptional activators, which have improved properties compared to the ones described in both earlier applications.

DESCRIPTION OF THE FIGURES

FIG. 4 Alignment of the PrtT sequence of the invention (SEQ ID NO 3 is '*A. niger* 1') and the PrtT sequence ('*A. niger* 2') from WO 00/20596 and WO 01/68864. The differences between these amino acid sequences are marked in grey. The underlined sequences depict the position of the zinc binuclear cluster Zn(II)2-Cys6 DNA binding domain (47-89) and Leucine zipper (438-461, as counted based on the *A. niger* 1 sequence), respectively.

FIG. 5 Alignment of the PrtT sequence of the invention (SEQ ID NO 3 is '*A. niger*') and the *A. oryzae* PrtT sequence from WO 01/68864 ('*A. oryzae*'). The differences between these amino acids sequences are marked in grey.

FIG. 14 Alignment of the PrtT sequence of *A. niger* WT1 ('*A. niger*') as determined from the sequenced cDNA's (SEQ ID NO 3) and the *A. oryzae* PrtT sequence identified by TBlastn search against the Patent database ('*A. oryzae*'). The differences between these two amino acids sequences are marked in grey.

FIG. 15 Alignment of the PrtT sequence of *A. oryzae* ('*A. oryzae*1') as identified by the TBlastn search against the Patent database (SEQ ID NO 15) and the *A. oryzae* PrtT sequence from WO 01/68864 ('*A. oryzae*2'). The differences between these two amino acids sequences are marked in grey.

Figure 16:
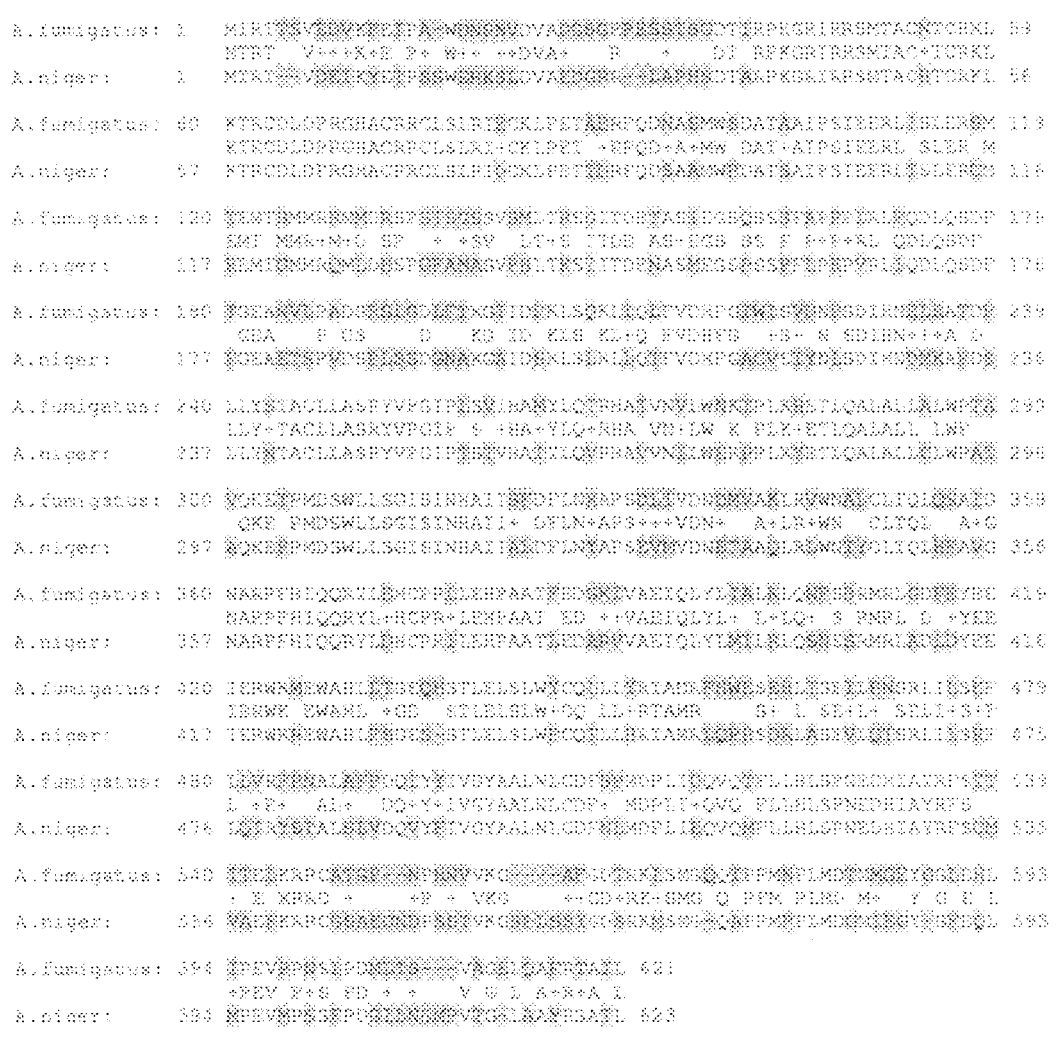

FIG. 16 Alignment of the *A. fumigatus* PrtT sequence identified by TBlastn search against nucleotide databases ('*A. fumigatus*') and the PrtT sequence of *A. niger* WT1 ('*A. niger*') as determined from the sequenced cDNA's (SEQ ID NO 3). The differences between these two amino acids sequences are marked in grey.

FIG. 17 CLUSTAL W multiple alignment of four fungal PrtT polypeptides of this invention. The marked boxes depict the position of the zinc binuclear cluster Zn(II)2-Cys6 DNA binding domain (grey) and Leucine zipper (in bold), respectively. The conserved Leu residues in the Leucine zipper box are in italics.

under the alignment signifies the presence of an identical amino acid, means that the type of amino acids is conserved in all three sequences, and means that at least in two sequences a similar type of amino acid is present.

The underlined sequence shows where the peptide SEQ ID NO 22 is localized.

FIG. 18 The comparison of the peptide SEQ ID NO 22 from *A. niger* WT1 and the corresponding peptide sequences in the other PrtT fungal polypeptides of the invention and those from the patent applications WO 00/20596 and WO 01/68864.

Figure 19:
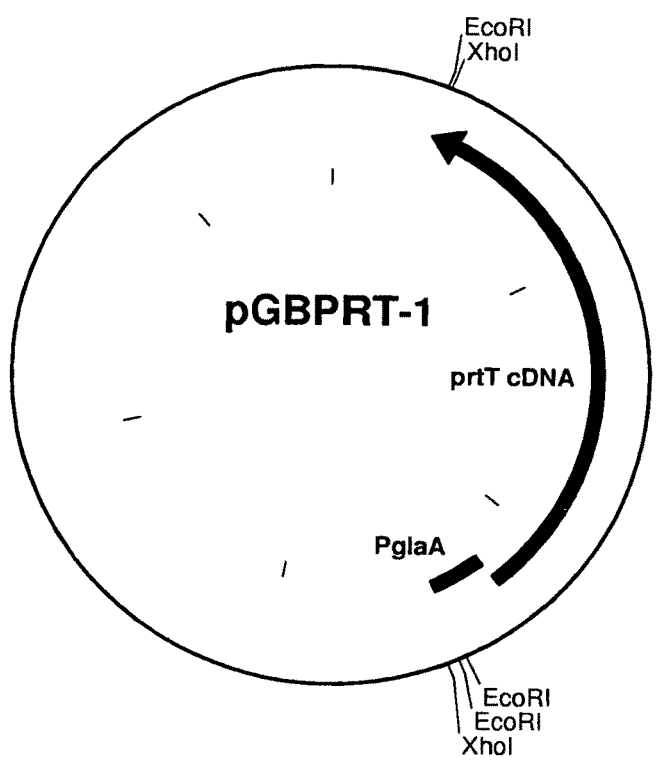

FIG. 19 Plasmid map of pGBFINPRT-1 Indicated are a 200 bp 3'-fragment of the pg/aA promoter fused to the full-length prtT cDNA sequence according to SEQ ID NO: 2. The PCR generated fusion fragment was cloned in pCR-BluntII-TOPO vector from Invitrogen. The fusion fragment can be isolated by restriction enzyme digestion with EcoRI and XhoI. Subsequently the fragment can be ligated into EcoRI and XhoI sites of expression vector pGBFIN-23.

DETAILED DESCRIPTION OF THE INVENTION

Polypeptides having Transcriptional Activation Activity on a Protease Promoter

According to a first aspect, the present invention relates to a polypeptide having transcriptional activity on a protease promoter, wherein said polypeptide is selected from the group consisting of:

(a) a polypeptide having an amino acid sequence which has at least 50% match percentage, i.e. identity, with the amino acid sequence of SEQ ID NO: 3 or SEQ ID NO: 15 or SEQ ID NO: 18 or SEQ ID NO: 21 or a polypeptide comprising a peptide fragment, said peptide fragment having at least 50% match percentage with SEQ ID NO:22 or SEQ ID NO: 4 or SEQ ID NO:25 or SEQ ID NO:26 or SEQ ID NO:27; or (b) a polypeptide comprising peptide fragments, said peptide fragments having at least 50% match percentage with both SEQ ID NO:22 and SEQ ID NO: 4, or with both SEQ ID NO:22 and SEQ ID NO:25, or with both SEQ ID NO:22 and SEQ ID NO:26, or with both SEQ ID NO:22 and SEQ ID NO:27; or (c) a polypeptide having an amino acid sequence according to (a) and (b) or (a) and (c); or (d) a polypeptide having an amino acid sequence which has at least 50% match percentage, i.e. identity, with the amino acid sequence of SEQ ID NO: 3 or SEQ ID NO: 15 or SEQ ID NO: 18 or SEQ ID NO: 21 and comprising a peptide fragment, said peptide fragment having the amino acid sequence: EWAHL(X)$_{5\text{-}20}$ST, wherein "X" represents any amino acid and the range 5-20 represents the number of "X" found or, (e) a variant of (a) or (b) or (c) or (d) or (e).

A polypeptide having transcriptional activity on a protease promoter is a transcriptional activator of a protease promoter. The term "transcriptional activator" as used herein refers to a polypeptide which has the capability to activate transcription from a specific protease promoter or a set of protease promoters, said activator being necessary for the initiation of transcription of the protease(s) encoding sequence to which the protease promoter(s) is (are) operably linked to.

The biological activity of the transcriptional activator is preferably determined through measurement of protease activities as described in the example section herein for determination of the acidic endo-protease activity using Bovine Serum Albumin (BSA) as substrate. A detailed description of this method is also described by van den Hombergh et al., Current Genetics 28: 299-308 (1995). Alternative methods for protease measurements can be found in WO 02/068623. Alternatively, one or more specific protease reporter genes such as the pepstatin sensitive extracellular aspartic protease encoding pepA gene can be used for measuring the activity of the transcriptional activator.

Additionally, the use of a reporter gene under the control of a protease promoter can be considered such that the enzymatic activity of the reporter protein, which is in operative association with the protease promoter is measured. An example of measuring the activity of a lacZ and GFP reporter gene have already been described (Luo, Gene,(1995),163: 127-131 and in Santerre Henriksen A L et al, Microbiology, (1999),145:729-34).

Alternatively, the biological activity of the transcriptional activator activity can be determined by measuring the mRNA levels of the protease transcripts. The mRNA levels can, for example, be measured through a Northern blot (J. Sambrook, E. F. Fritsch, and T. Maniatis, 1989, Molecular Cloning, A Laboratory Manual, 2d edition, Cold Spring Harbor, N.Y.).

According to a preferred embodiment, the polypeptide of the present invention does not have the amino acid sequence SEQ ID NO:2 or SEQ ID NO:49 as disclosed in WO 01/68864.

For purposes of the present invention, the degree of identity, i.e. the match percentage, between two polypeptides, respectively two nucleic acid sequences is preferably determined using the optimal global alignment method CDA (Huang, 1994, A Context Dependent Method for Comparing Sequences, Proceedings of the 5th Symposium on Combinatorial Pattern Matching, Lecture Notes in Computer Science 807, Springer-Verlag, 54-63) with the parameters set as follows: (i) for (poly)peptide alignments: Mismatch:-2 GapOpen:11 GapExtend:1 ContextLength:10 MatchBonus:1, and (ii) for nucleotide sequence alignments Mismatch:-15 GapOpen:5 GapExtend:2 ContextLength:10 Match Bonus:1.

The terms "degree of identity", "identity" and "match percentage" are used interchangeably to indicate the degree of identity between two polypeptides or nucleic acid sequences as calculated by the optimal global alignment method indicated above. Examples of alternative programs used for alignments and determination of homology are Clustal method (Higgins, 1989, CABIOS 5 : 151-153), the Wilbur-Lipman method (Wilbur and Lipman, 1983, Proceedings of the National Academy of Science USA 80: 726-730) using the LASERGENE™ MEGALIGN™ software (DNASTAR, Inc., Madison, Wis.), BLAST (NCBI), GAP (Huang) for the optimal global alignments, MAP (Huang), MultiBLAST (NCBI), ClustalW, Cap Assembler and Smith Waterman for multiple alignments.

References

| Pairwise alignment: (1) BLAST, (2) GAP, (3) MAP, (4) Smith Waterman, and (5) Cap Assembler | |
|---|---|
| (1) Tatusova TA and Madden TL (1999) | BLAST 2 sequences, a new tool for comparing protein and nucleotide sequences. *FEMS Microbiol Lett* 174: 247-50 |
| (2) (3) Huang X (1994) | On global sequence alignment. *Comput Appl Biosci* 10: 227-35 |
| (4) Smith TF and Waterman MS (1981) | Identification of common molecular subsequences. *J Mol Biol* 147: 195-197 |
| (5) Huang X (1992) | A contig assembly program based on sensitive detection of fragment overlaps. *Genomics* 14: 18-25 |

-continued

| Pairwise alignment: (1) BLAST, (2) GAP, (3) MAP, (4) Smith Waterman, and (5) Cap Assembler | |
|---|---|
| (5) Huang X (1996) | An improved sequence assembly program. *Genomics* 33: 21-31 |
| (6) Thompson JD, Higgins DG, and Gibson TJ (1994) | CLUSTAL W: improving the sensitivity of progressive multiple sequence alignment through sequence weighting, positions-specific gap penalties and weight matrix choice. *Nucleic Acids Research* 22: 4673-4680 |

Figure 3:
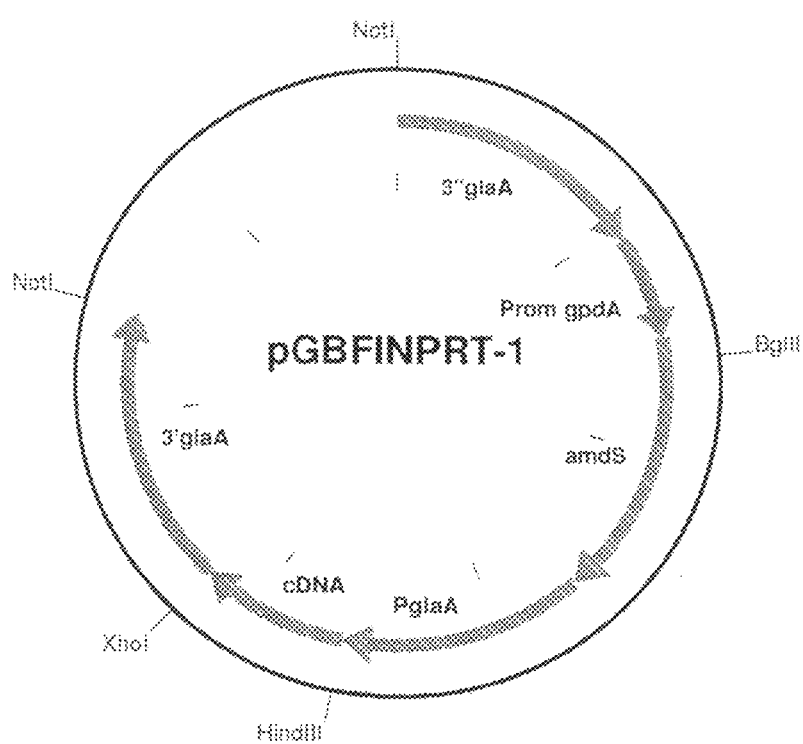
FIG. 3 Plasmid map of expression vector pGBFINPRT-1. Indicated are the glaA flanking regions relative to the glaA promoter and the cDNA insert encoding the PrtT transcriptional regulator of the invention in the HindIII-XhoI cloning site. The *E. coli* DNA can be removed by digestion with restriction enzyme NotI, prior to transformation of the *A. niger* strains.

In a most preferred embodiment, the polypeptide has the amino acid sequence of SEQ ID NO: 3 or SEQ ID NO: 15 or SEQ ID NO: 18 or SEQ ID NO: 21 or a polypeptide obtainable by expression of the prtT cDNA contained in pGBFIN-PRT-1 shown in FIG. 3, deposited under accession number CBS118680 or a polypeptide obtainable by expression of the prtT cDNA contained in pGBPRT-1 shown in FIG. 19, deposited under accession number CBS118681.

According to a more preferred embodiment, the polypeptide has an amino acid sequence which has at least 50% match percentage, i.e. identity, with the amino acid sequence of SEQ ID NO: 3 or SEQ ID NO: 15 or SEQ ID NO: 18 or SEQ ID NO: 21 and comprises a peptide fragment, said peptide fragment having at least 50% match percentage, i.e. identity, with SEQ ID NO: 22 or SEQ ID NO: 4 or SEQ ID NO: 25 or SEQ ID NO:26 or SEQ ID NO:27.

According to another more preferred embodiment, the polypeptide has an amino acid sequence which has at least 50% match percentage, i.e. identity, with the amino acid sequence of SEQ ID NO: 3 or SEQ ID NO: 15 or SEQ ID NO: 18 or SEQ ID NO: 21 and comprises peptide fragments, said peptide fragments having at least 50% match percentage with both SEQ ID NO:22 and SEQ ID NO: 4, or with both SEQ ID NO:22 and SEQ ID NO:25, or with both SEQ ID NO:22 and SEQ ID NO:26, or with both SEQ ID NO:22 and SEQ ID NO:27.

According to another preferred embodiment, the polypeptide has an amino acid sequence which has at least 50% match percentage, i.e. identity, with the amino acid sequence of SEQ ID NO: 3 or SEQ ID NO: 15 or SEQ ID NO: 18 or SEQ ID NO: 21 and comprises a peptide fragment, said peptide fragment having the amino acid sequence: EWAHL(X)$_{5-20}$ST, wherein "X" represents any amino acid and the number represents the number of "X" found. An example of such a peptide fragment is represented by the SEQ ID NO: 22.

Preferably, the match percentage, i.e. identity, is at least about 60%, preferably at least about 70%, more preferably at least about 80%, even more preferably at least about 90%, even more preferably at least about 93%, even more preferably at least about 95%, even more preferably at least about 96%, even more preferably at least about 97%, even more preferably at least about 98%, most preferably at least about 99%.

According to another preferred embodiment, the polypeptide is a variant of any one of the polypeptide sequences defined before. Modification of the polypeptide of the present invention may be necessary for the synthesis of variant polypeptides. The term variant preferably refers to non-naturally occurring forms of the polypeptide. These polypeptide variants may differ in some engineered way from the polypeptide isolated from its native source. For example, it may be of interest to synthesize variants of the polypeptide where the variants differ in specific activity, binding specificity and/or affinity, or the like by, e.g., site-directed mutagenesis. The variant sequence may be constructed on the basis of the amino acid sequence of SEQ ID NOs: 3, 15, 18 or SEQ ID NO: 21 or on the basis of the nucleic acid sequence presented as the polypeptide encoding part of SEQ ID NOs: 2, 14, 17 or SEQ ID NO: 20.

A variant of SEQ ID NOs: 3, 15, 18 or SEQ ID NO: 21 is preferably a polypeptide having:
  one or more amino acids deleted preferably from the amino and/or carboxy terminus of this amino acid sequence and/or
  one or more amino acid residues inserted and/or
  one or more amino acid residues replaced by one or more different amino acid residues
  combinations of the variations mentioned above.

According to another preferred embodiment, a variant of SEQ ID NOs: 3,15, 18 or SEQ ID NO: 21 contains at least the polypeptide sequence shown in SEQ ID NOs: 3, 15, 18 or SEQ ID NO: 21.

In a preferred embodiment, the polypeptides have an amino acid sequence which differs by five amino acids, preferably by four amino acids, more preferably by three amino acids, even more preferably by two amino acids, and most preferably by one amino acid from the amino acid sequence set forth in SEQ ID NOs: 3, 15, 18 or SEQ ID NO: 21 or SEQ ID NO: 22.

According to another preferred embodiment, a polypeptide variant is a transcriptional activator isolated from other organisms and/or another family member of the transcriptional activator initially isolated and present in the same organism.

According to a preferred embodiment, the polypeptide variant contains mutations that do not alter the biological function of the encoded polypeptide. Such polypeptides differ in amino acid sequence from SEQ ID NOs 3, 15, 18 or SEQ ID NO: 21, yet retain at least one of their biological activities and preferably, these proteins are not the ones having SEQ ID NO: 2 or 49 as disclosed in WO 01/68864. Guidance concerning how to make phenotypically silent amino acid substitutions is provided in Bowie, J. U. et al., Science 247:1306-1310 (1990).

According to a preferred embodiment, the polypeptide variant exhibits a particular function of the transcriptional activator of a protease promoter. This transcriptional activator variant exhibits at least the function of transcriptional activator on at least one protease promoter. This variant may contain only conservative substitutions of one or more amino acids of sequences having SEQ ID NOs 3, 15, 18 or SEQ ID NO: 21, or substitutions, insertions or deletions of non-essential amino acids. Accordingly, a non-essential amino acid is a residue that can be altered in one of these sequences without substantially altering the biological function. For example, amino acid residues that are conserved among the transcriptional activator of the present invention are predicted to be particularly unamenable to alteration. The term "conservative substitution" is intended to mean that a substitution in which the amino acid residue is replaced with an amino acid residue having a similar side chain. These families are known in the art and include amino acids with basic side chains (e.g. lysine, arginine and hystidine), acidic side chains (e.g. aspartic acid, glutamic acid), uncharged polar side chains (e.g., glycine, asparagines, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine tryptophan, histidine). Such mutations may be introduced by standard techniques, such as site-directed mutagenesis and PCR-mediated mutagenesis. Example of mutagenesis procedures are the QuickChange™ site-directed mutagenesis kit (Stratagene Cloning Systems, La Jolla, Calif.), the The Altered Sites® II in vitro Mutagenesis Systems' (Promega Corporation) or by overlap extension using PCR as described in Gene. 1989 Apr. 15; 77(1):51-9. (Ho S N, Hunt H D, Horton R M, Pullen J K, Pease L R "Site-directed mutagenesis by overlap extension using the polymerase chain reaction") or using PCR as described in *Molecular Biology: Current Innovations and Future Trends*. (Eds. A. M. Griffin and H. G. Griffin. ISBN 1-898486-01-8 ;1995 Horizon Scientific Press, PO Box 1, Wymondham, Norfolk, U.K.).

The transcriptional activator of a protease promoter of the invention may be obtained from any filamentous fungus.

"Filamentous fungi" include all filamentous forms of the subdivision Eumycota and Oomycota (as defined by Hawksworth et al., 1995, supra). The filamentous fungi are characterized by a mycelia wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, and *Trichoderma*.

In a more preferred embodiment, the transcriptional activator of a protease promoter of the present invention is obtained from a strain of *Aspergillus*, such as *A. awamori, A. nidulans, A. niger, A. oryzae, A. sojae* or *A. fumigatus*. Preferably, the transcriptional activator is obtained from a strain of *A. niger* or *A. oryzae* or *A. fumigatus*. Even more preferably, the transcriptional activator is obtained from an isolate of a strain of *A. fumigatus*; e.g., the polypeptide sequence set forth in SEQ ID NO: 18. Even more preferably, the transcriptional activator is obtained from an isolate of a strain of *A. oryzae*; e.g., the polypeptide sequence set forth in SEQ ID NO: 15. Even more preferably, the transcriptional activator is obtained from an isolate of a strain of *A. niger*, e.g., the polypeptide sequence set forth in SEQ ID NO: 3.

In another preferred embodiment, the transcriptional activator is obtained from an isolate of a strain of *Penicillium*, such as *Penicillium chrysogenum*; e. g., the polypeptide sequence set forth in SEQ ID NO: 21.

According to another preferred embodiment, the transcriptional activator of the invention is an orthologue of the *A. niger, A. oryzae, A. fumigatus*, or *P. chrysogenum* transcriptional activator. Orthologues of these polypeptides are polypeptides that can be isolated from other strains or species and possess a similar or identical biological activity. Such orthologues can readily be identified as comprising an amino acid sequence that is substantially homologous to SEQ ID NOs:3, 15, 18 or SEQ ID NO:21.

The term "substantially homologous" refers to a first polypeptide or nucleotide sequence which contains a sufficient or minimum number of identical or equivalent (e.g., with similar side chain) amino acids or nucleotides to a second polypeptide or nucleotide sequence such that the first and the second polypeptide or nucleotide sequences have a common peptide or nucleic acid fragment. For example, polypeptide or nucleotide sequences which contain a common peptide or nucleic acid fragment having about 90%, preferably about 92%, preferably about 93%, preferably about 95%, more preferably about 97%, even more preferably about 99%, identity or more are defined herein as sufficiently identical. An example of such a common domain is the one depicted in SEQ ID NOs: 4, 22, 25, 26 or SEQ ID NO: 27.

In a preferred embodiment, the transcriptional activator of protease promoters has an amino acid sequence according to SEQ ID NOs 3, 15, 18 or SEQ ID NO: 21. In another embodiment, the polypeptide or a peptide derived thereof is substantially homologous to the amino acid sequence according to SEQ ID NOs 3, 15, 18 or SEQ ID NOs: 21, 4, 22, 25, 26, 27 and retains at least one biological activity of a polypeptide according to SEQ ID NOs 3, 15, 18 or SEQ ID NO: 21, yet differs in amino acid sequence due to natural variation or mutagenesis as described above. Preferably, the transcriptional activator of protease promoters of the invention are not the ones depicted in WO 01/68864 and having SEQ ID NO: 2 or 49.

In another preferred embodiment, the transcriptional activator of the present invention is obtained from a strain of *Fusarium*, such as *F. oxysporum*. Preferably, the strain is a strain of *F. venenatum*.

It will be understood that for the aforementioned species, the invention encompasses both the perfect and imperfect states, and other taxonomic equivalents, e. g., anamorphs, regardless of the species name by which they are known. Those skilled in the art will readily recognize the identity of appropriate equivalents. For example, the polypeptides may be obtained from micro-organisms, which are taxonomic equivalents of *Aspergillus* as defined by Raper, K. D. and Fennel, D. I.(1965. The Genus *Aspergillus*, The Wilkins Company, Baltimore Md.) regardless of the species name by which they are known.

*Aspergilli* are mitosporic fungi characterized by an aspergillum comprised of a conidiospore stipe with no known teleomorphic states terminating in a vesicle, which in turn bears one or two layers of synchronously formed specialized cells, variously referred to as sterigmata or phialides, and asexually formed spores referred to as conidia. Known teleomorphs of *Aspergillus* include *Eurotium, Neosartorya*, and *Emericella*.

Strains of *Aspergillus* and teleomorphs thereof are readily accessible to the public in a number of culture collections. According to a preferred embodiment, the strains of filamentous fungus used to isolate the transcriptional activator is *Aspergillus niger* CBS 513.88, *Aspergillus oryzae* ATCC 20423, IFO 4177, ATCC 1011, ATCC 9576, ATCC14488-14491, ATCC 11601, ATCC12892, *Aspergillus fumigatus* AF293 (CBS101355), *P. chrysogenum* CBS 455.95, *Penicillium citrinum* ATCC 38065, *Penicillium chrysogenum* P2, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* ATCC44006 and derivatives thereof.

Furthermore, such transcriptional activators of protease promoters may be identified and obtained from other sources including micro-organisms isolated from nature (e. g., soil, composts, water, etc.) using the above-mentioned probes. Techniques for isolating micro-organisms from natural habitats are well known in the art. The nucleic acid sequence may then be derived by similarly screening a genomic or cDNA library of another micro-organism. Once a nucleic acid sequence encoding a transcriptional activator of protease promoter has been detected with the probe (s), the sequence may be isolated or cloned by utilizing techniques which are known to those of ordinary skill in the art (see, e.g., J. Sambrook,et al. 1989,).

Deteriorated Transcriptional Activator of a Protease Promoter

In another preferred embodiment of the invention, variants of transcriptional activator of a protease promoter are deteriorated transcriptional activators of a protease promoter.

Deteriorated transcriptional activators of a protease promoters are polypeptides, wherein at least one of their biological activities is decreased compared to the biological activity of their wild type counterpart measured in a given filamentous fungal host using a given assay or an in vitro assay as defined earlier in the description. For example, such polypeptide may have less transcriptional activity than its wild type counterpart on at least one protease promoter as measured in a given filamentous fungal host using one of the given assays. Alternatively, the deteriorated polypeptide may have lost its transcriptional activity as compared to the activity of its wild type counterpart on at least one specific protease promoter and retained the activity of its wild type counterpart on at least another protease promoter as measured in a given filamentous fungal host using one of the given assays. According to a preferred embodiment, the deteriorated transcriptional activator does not have any detectable transcriptional activating activity on any protease promoter tested by comparison with the activity of its wild type counterpart as measured in a given filamentous fungal host using one of the given assays. A preferred assay for measuring the transcriptional activity of a deteriorated transcriptional activator is by measuring the acidic endo-protease activity using Bovine Serum Albumin (BSA) as substrate as described herein. Preferably, the filamentous fungal host used to perform the protease assay is one of the deposited strains as described earlier on in the description. All these deteriorated transcriptional activators may be used to replace their wild type counterpart in a given filamentous fungal host cell. Such a cell is highly suited for producing any polypeptide subject to protease degradation (see section host cell). Such a cell, especially *Aspergillus fumigatus* may also have a reduced pathogenicity.

Such polypeptide may be obtained by randomly introducing mutations along all or part of their coding sequence (using SEQ ID NOs:2, 14, 17 or SEQ ID NO: 20,), such as by saturation mutagenesis, and the resulting mutants can be expressed recombinantly and screened for biological activity using one of the assays mentioned in the previous paragraphs. For instance, the art provides standard assays for measuring the transcriptional activity and thus transcriptional activator with deteriorated transcriptional activity may easily be selected.

Transcriptional Activator of a Protease Promoter with Enhanced Activity

According to another preferred embodiment of the invention, variants of transcriptional activators of a protease promoter are transcriptional activators of a protease promoter with enhanced activity. Transcriptional activators of a protease promoter with enhanced activity are polypeptides, wherein at least one of their biological activities is increased compared to the biological activity of their wild type counterpart measured in a given filamentous fungal host using a given assay or an in vitro assay. For example, such polypeptide may have at least more transcriptional activity than its wild type counterpart on at least one protease promoter as-measured in a given filamentous fungal host using one of the assays mentioned in the previous paragraphs. Alternatively, the enhanced polypeptide may have more transcriptional activity on protease promoter than its wild type counterpart on at least one specific protease promoter and retained the activity of its wild type counterpart on at least one other protease promoter as measured in a given filamentous fungus using one of the given assays. According to a preferred embodiment, the enhanced transcriptional activator has an enhanced transcriptional activating activity on any protease promoter tested by comparison to the activity of its wild type counterpart as measured in a given filamentous fungus host using one of the assays described earlier. A preferred assay for measuring the transcriptional activity of a deteriorated transcriptional activator is by measuring the acidic endo-protease activity using Bovine Serum Albumin (BSA) as substrate as described herein. Preferably, the filamentous fungal host used to perform the protease assay is one of the deposited strains as described earlier on in the description. All these enhanced transcriptional activator may be used to replace their wild type counterpart in a given filamentous fungal host cell. Such a cell is highly suited for producing any polypeptide subject to transcription regulation by such a transcriptional activator (see section host cell). Such enhanced transcriptional activator may be obtained using the same strategy as the one described for obtaining deteriorated transcriptional activator.

Nucleic Acid Sequence Encoding a Transcriptional Activator of a Protease Promoter According to a further aspect, the invention provides a nucleic acid sequence coding for the polypeptide as defined in the former sections.

In a preferred embodiment, the nucleic acid sequence is selected from the group consisting of:
(a) a nucleic acid sequence having at least 50% match percentage, i.e. identity with the nucleic acid sequence of SEQ ID NO: 2 or SEQ ID NO: 14 or SEQ ID NO: 17, or SEQ ID NO: 20 ; or
(b) a nucleic acid sequence comprising a fragment, said fragment having at least 45% match percentage, i.e. identity with the fragment consisting of base pair number 1267 till base pair number 1302 of nucleic acid sequence of SEQ ID NO:2; or
(c) a nucleic acid sequence having at least 50% match percentage, i.e. identity with the nucleic acid sequence of SEQ ID NO: 2 or SEQ ID NO: 14 or SEQ ID NO: 17, or SEQ ID NO: 20 ; and comprising a fragment, said fragment having at least 45% match percentage, i.e. identity with the fragment consisting of base pair number 1267 till base pair number 1302 of nucleic acid sequence of SEQ ID NO:2; or
(d) a variant of (a), (b), or (c); or
(e) a subsequence of (a), (b), (c) or (d).

Preferably the match percentage, i.e. identity is of at least about 60%, more preferably at least about 70%, even more preferably at least about 80%, most preferably at least about 90%, even most preferably at least about 93%, even most preferably at least about 95%, even most preferably at least about 96%, even most preferably at least about 97%, even most preferably at least about 98%, even most preferably at least about 99% identity.

In an even more preferred embodiment, the nucleic acid sequence encoding a transcriptional activator of a protease promoter has a nucleic acid sequence as set forth in SEQ ID NO: 2, or, SEQ ID NO: 14, or SEQ ID NO: 17 or SEQ ID NO: 20, or the XhoI/HindIII fragment of plasmid pGBFINPRT-1 depicted in FIG. 3, deposited under accession number CBS118680 or the prtT cDNA contained in plasmid pGB-PRT-1 depicted in FIG. 19, deposited under accession number CBS118681.

According to another preferred embodiment, the nucleic acid sequence of the invention is not the nucleic acid sequence SEQ ID NO: 1 or SEQ ID NO: 48 as disclosed in WO 01/68864.

According to another preferred embodiment, the nucleic acid sequence of the invention is a variant of any of the nucleic acid sequences as defined before. Modification of the nucleic acid sequence of the present invention may be necessary for the synthesis of variant polypeptides (as defined earlier in the description). The nucleic acid sequence variant may be constructed on the basis of the nucleic acid sequence SEQ ID NOs: 2, 14, 17 or SEQ ID NO: 20 or the XhoI/HindIII fragment of plasmid pGBFINPRT-1 depicted in FIG. 3, deposited under accession number CBS118680 or the prtT cDNA contained in plasmid pGBPRT-1 depicted in FIG. 19, deposited under accession number CBS118681.

A nucleic acid sequence variant may be a fragment of the native nucleic acid sequence cited in the former paragraph. A preferred nucleic acid sequence variant is a nucleic acid sequence, which contains silent mutations. Alternatively or in combination, a nucleic acid sequence variant may also be obtained by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, Protein Expression and Purification 2: 95-107.

Preferably, the nucleic acid variant is such that starting from any one of the nucleic acid sequences cited in the former paragraph, one or more nucleotides from the 5' and/or 3' end have been deleted. More preferably, the variant encodes a polypeptide fragment, which has transcriptional activation activity on a protease promoter.

Alternatively or in combination, a nucleic acid sequence variant is preferably a nucleic acid sequence encoding a transcriptional activator isolated from other organisms and/or another family member of the transcriptional activator initially isolated and present in the same organism. All these variants can be obtained in a typical approach, using cDNA or genomic DNA libraries constructed from organisms, e.g. filamentous fungi, in particular from the species *Aspergillus* by screening them by hybridisation (standard Southern blotting procedures) under low to medium to high stringency conditions with one of the following nucleic acid sequences which can be used to design probes:

SEQ ID NO: 2,
SEQ ID NO: 14,
SEQ ID NO: 17,
SEQ ID NO: 20,
the XhoI/HindIII fragment of plasmid pGBFINPRT-1 depicted in FIG. 3, deposited under accession number CBS118680,
the the prtT cDNA contained in plasmid pGBPRT-1 depicted in FIG. 19, deposited under accession number CBS118681.
or a fragment of any one of these sequences, preferably the fragment consisting of base pair number 1267 till base pair number 1302 of nucleic acid sequence of SEQ ID NO:2,
their complementary strand.

Low to medium to high stringency conditions means prehybridization and hybridization at 42° C. in 5× SSPE, 0.3% SDS, 200 µg/ml sheared and denatured salmon sperm DNA, and either 25%, 35% or 50% formamide for low to medium to high stringencies, respectively. Subsequently, the hybridization reaction is washed three times for 30 minutes each using 2×SSC, 0.2% SDS and either 55° C., 65° C. or 75° C. for low to medium to high stringencies.

The designed probes can be considerably shorter than the entire sequence, but should be at least 15, preferably at least 25, and more preferably at least 40 nucleotides in length. Additionally, such probes can be used to amplify DNA probes through PCR. Both DNA, RNA and Peptide Nucleid Acid (PNA) probes can be used for hybridisation. Such probes are encompassed by the present invention. The probes are typically labeled for detecting the corresponding gene (for example, with 32P, 33P, 3H, 35S, biotin, avidin or a fluorescent marker). For example, molecules to which a 32P, 33P, 3H- or 35S-labelled oligonucleotide probe hybridizes may be detected by use of X-ray film or Phospho-Image analysis.

A variant of the nucleic acid sequence may also be a paralogous of the transcriptional activator of a protease promoter. In the context of the invention, paralogous means nucleic acid sequence homologous of SEQ ID NO: 2, the nucleic acid sequence consisting of base pair number 1267 till base pair number 1302 of nucleic acid sequence of SEQ ID NOs:2, 14, 17 or SEQ ID NO: 20 and derived from *A. niger* or *A. oryzae* or *A. fumigatus* or *P. chrysogenum*.

For example, *Aspergillus* strains can be screened for homologous nucleic acid sequences coding for the transcriptional activator of a protease promoter by Northern blot analysis. Upon detection of transcripts homologous to nucleic acid sequences according to the invention, cDNA libraries can be constructed from RNA isolated from the appropriate strain, utilizing standard techniques well known to those of skill in the art. Alternatively, a total genomic DNA library can be screened using a probe that hybridises to a nucleic acid sequence according to the invention.

The template for the reaction can be cDNA obtained by reverse transcription of mRNA prepared from strains known or suspected to express a nucleic acid sequence according to the invention. The PCR product can be subcloned and sequenced to ensure that the amplified sequences represent the nucleic acid sequences of a new transcriptional activator of a protease promoter, or a functional equivalent thereof. The PCR fragment can then be used to isolate a full-length cDNA clone by a variety of known methods. PCR technology also can be used to isolate full-length cDNA sequences from other organisms. For example, RNA can be isolated, following standard procedures, from an appropriate cellular or tissue source. The resulting RNA/DNA hybrid can then be "tailed" (e.g., with guanines) using a standard terminal transferase reaction, the hybrid can be digested with RNase H, and second strand synthesis can then be primed (e.g., with a poly-C primer). For a review of useful cloning strategies, see e.g. Sambrook et al., 1989; and Ausubel et al., Current Protocols in Molecular Biology, Wiley Interscience Publishers, 1995.

According to another preferred embodiment, a nucleic acid variant is an allelic variant. An allelic variant denotes any of two or more alternative forms of a gene occupying the same chomosomal locus. Allelic variation arises naturally through mutation, and may result in phenotypic polymorphism within populations. Gene mutations can be silent (i. e., no change in the encoded polypeptide) or may encode polypeptides having altered amino acid sequences. In a preferred embodiment, the nucleic acid sequence encoding a transcriptional activator of protease promoter of the present invention is an allelic variant of one of the nucleic acid sequences defined earlier in the description.

Nucleic acid variant may also be nucleic acid sequences, which differ from:
SEQ ID NO:2,
SEQ ID NO: 14,
SEQ ID NO: 17 or
SEQ ID NO: 20,
the XhoI/HindIII fragment of plasmid pGBFINPRT-1 (depicted in FIG. 3), deposited under accession number CBS118680,
the prtT cDNA contained in plasmid pGBPRT-1 depicted in FIG. 19, deposited under accession number CBS118681
by virtue of the degeneracy of the genetic code.

Nucleic acid variant may also be nucleic acid sequences, which comprises a variant of the fragment consisting of base pair number 1267 till base pair number 1302 of nucleic acid sequence of SEQ ID NO:2. Variant is given the same meaning as earlier on in this section.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using methods based on polymerase chain reaction (PCR) or antibody screening of expression libraries to detect cloned DNA fragments with shared structural features (See, e.g., Innis et al., 1990, PCR: A Guide to Methods and Application, Academic Press, New York.). Other nucleic acid amplification procedures such as ligase chain reaction (LCR), ligated activated transcription (LAT) and nucleic acid sequence-based amplification (NASBA) may be used.

In another preferred embodiment, the nucleic acid sequence encodes a polypeptide comprising the amino acid sequence of SEQ ID NO: 3, or SEQ ID NO: 15, or SEQ ID NO: 18 or SEQ ID NO: 21 or a fragment thereof, which has transcriptional activation activity on a protease promoter. In another preferred embodiment, the nucleic acid sequence encodes a polypeptide comprising the amino acid sequence of SEQ ID NO: 4, or SEQ ID NO: 25, or SEQ ID NO:26, or SEQ ID NO: 27 and/or SEQ ID NO: 22.

According to another preferred embodiment, the invention relates to nucleic acid sequences having SEQ ID NO: 16 and SEQ ID NO: 19. These nucleic acid sequences are genomic nucleic acid sequences from *A. fumigatus* and *P. chrysogenum* respectively.

Sequence Errors

The sequence information as provided herein should not be so narrowly construed as to require inclusion of erroneously identified bases. The specific sequences disclosed herein can be readily used to isolate the complete gene from filamentous fungi, in particular *A. niger* which in turn can easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a nucleic acid sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

It is to be understood that the present invention does not comprise the prtT nucleic acid sequences and the PrtT polypeptide sequences as disclosed in WO 01/68864 and having respectively SEQ ID NO: 1, or 48 and 2, or 49.

Nucleic Acid Constructs

Another aspect of the present invention relates to nucleic acid constructs comprising a nucleic acid sequence encoding a transcriptional activator of a protease promoter of the invention as isolated or with either deteriorated or enhanced transcriptional activity on a protease promoter, said nucleic acid sequence being operably linked to one or more control sequences, which direct the production of the transcriptional activator of a protease promoter in a suitable expression host. In a preferred embodiment, the nucleic acid sequence is SEQ ID NOs: 2, 14, 17 or SEQ ID NO: 20, encoding the polypeptide shown in SEQ ID NOs: 3, 15, 18 or SEQ ID NO: 21, respectively.

Expression will be understood to include any step involved in the production of the polypeptide including, but not limited to transcription, post-transcriptional modification, translation, post-translational modification, and secretion.

Manipulation of the nucleic acid sequence encoding a polypeptide prior to its insertion into a vector may be desirable or necessary depending on the expression vector. The techniques for modifying nucleic acid sequences utilizing cloning methods are well known in the art.

"Nucleic acid construct" is defined herein as a nucleic acid molecule, either single-or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence. The term "coding sequence" as defined herein is a sequence, which is transcribed into mRNA and translated into a transcriptional activator of a protease promoter of the invention. The boundaries of the coding sequence are generally determined by the ATG start codon at the 5'end of the mRNA and a translation stop codon sequence terminating the open reading frame at the 3'end of the mRNA. A coding sequence can include, but is not limited to, DNA, cDNA, and recombinant nucleic acid sequences.

The term "control sequences" is defined herein to include all components, which are necessary or advantageous for the expression of a polypeptide. Each control sequence may be native or foreign to the nucleic acid sequence encoding the polypeptide. Such control sequences include, but are not limited to, a leader, optimal translation initiation sequences (as described in Kozak, 1991, J. Biol. Chem. 266:19867-19870), a polyadenylation sequence, a pro-peptide sequence, a pre-pro-peptide sequence, a promoter, a signal sequence, and a transcription terminator. At a minimum, the control sequences include a promoter, and transcriptional and translational stop signals.

The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the production of a polypeptide.

The control sequence may be an appropriate promoter sequence, a nucleic acid sequence, which is recognized by a host cell for expression of the nucleic acid sequence. The promoter sequence contains transcriptional control sequences, which mediate the expression of the polypeptide. The promoter may be any nucleic acid sequence, which shows transcriptional activity in the cell including mutant, truncated, and hybrid promoters, and may be obtained from genes encoding extracellular or intracellular polypeptides either homologous or heterologous to the cell.

The control sequence may also be a suitable transcription terminator sequence, a sequence recognized by a filamentous fungal cell to terminate transcription. The terminator sequence is operably linked to the 3' terminus of the nucleic acid sequence encoding the polypeptide. Any terminator, which is functional in the cell, may be used in the present invention.

Preferred terminators for filamentous fungal cells are obtained from the genes encoding *A. oryzae* TAKA amylase, *A. niger* glucoamylase (glaA), *A. nidulans* anthranilate synthase, *A. niger* alpha-glucosidase, trpC gene and *Fusarium oxysporum* trypsin-like protease.

The control sequence may also be a suitable leader sequence, a non-translated region of a mRNA which is important for translation by the filamentous fungal cell. The leader sequence is operably linked to the 5' terminus of the nucleic acid sequence encoding the polypeptide. Any leader sequence, which is functional in the cell, may be used in the present invention.

Preferred leaders for filamentous fungal cells are obtained from the genes encoding *A. oryzae* TAKA amylase and *A. nidulans* triose phosphate isomerase and *A. niger* glaA.

Other control sequences may be isolated from the *Penicillium* IPNS gene, or pcbC gene, the beta tubulin gene. All the control sequences cited in WO 01/21779 are herewith incorporated by reference.

The control sequence may also be a polyadenylation sequence, a sequence which is operably linked to the 3' terminus of the nucleic acid sequence and which, when transcribed, is recognized by the filamentous fungal cell as a signal to add polyadenosine residues to transcribed mRNA. Any polyadenylation sequence, which is functional in the cell, may be used in the present invention.

Preferred polyadenylation sequences for filamentous fungal cells are obtained from the genes encoding *A. oryzae* TAKA amylase, *A. niger* glucoamylase, *A. nidulans* anthranilate synthase, *Fusarium oxysporum* trypsin-like protease and *A. niger* alpha-glucosidase.

Expression Vectors

The present invention also relates to recombinant expression vectors comprising a nucleic acid sequence of the invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites.

Alternatively, the nucleic acid sequence encoding the polypeptide may be expressed by inserting the sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus), which can be conveniently subjected to recombinant DNA procedures and can bring about the expression of the nucleic acid sequence encoding the polypeptide. The choice of the vector will typically depend on the compatibility of the vector with the filamentous fungal cell into which the vector is to be introduced. The vectors may be linear or closed circular plasmids. The vector may be an autonomously replicating vector, i. e., a vector, which exists as an extrachromosomal entity, the replication of which is independent of chromosomal replication, e.g., a plasmid, an extrachromosomal element, a minichromosome, or an artificial chromosome. An autonomously maintained cloning vector may comprise the AMA1-sequence (see e.g. Aleksenko and Clutterbuck (1997), Fungal Genet. Biol. 21: 373-397).

Alternatively, the vector may be one which, when introduced into the filamentous fungal cell, is integrated into the genome and replicated together with the chromosome (s) into which it has been integrated. The integrative cloning vector may integrate at random or at a predetermined target locus in the chromosomes of the filamentous fungal host cell. In a preferred embodiment of the invention, the integrative cloning vector comprises a DNA fragment, which is homologous to a DNA sequence in a predetermined target locus in the genome of the filamentous fungal host cell for targeting the integration of the cloning vector to this predetermined locus. In order to promote targeted integration, the cloning vector is preferably linearized prior to transformation of the host cell. Linearization is preferably performed such that at least one but preferably either end of the cloning vector is flanked by sequences homologous to the target locus. The length of the homologous sequences flanking the target locus is preferably at least 30 bp, preferably at least 50 bp, preferably at least 0.1 kb, even preferably at least 0.2 kb, more preferably at least 0.5 kb, even more preferably at least 1 kb, most preferably at least 2 kb. Preferably, the DNA sequence in the cloning vector, which is homologous to the target locus is derived from a highly expressed locus meaning that it is derived from a gene, which is capable of high expression level in the filamentous fungal host cell. A gene capable of high expression level, i.e. a highly expressed gene, is herein defined as a gene whose mRNA can make up at least 0.5% (w/w) of the total cellular mRNA, e.g. under induced conditions, or alternatively, a gene whose gene product can make up at least 1% (w/w) of the total cellular protein, or, in case of a secreted gene product, can be secreted to a level of at least 0.1 g/l (as described in EP 357 127 B1). A number of preferred highly expressed genes are given by way of example: the amylase, glucoamylase, alcohol dehydrogenase, xylanase, glyceraldehyde-phosphate dehydrogenase or cellobiohydrolase (cbh) genes from *Aspergilli* or *Trichoderma*. Most preferred highly expressed genes for these purposes are a glucoamylase gene, preferably an *A. niger* glucoamylase gene, an *A. onyzae* TAKA-amylase gene, an *A. nidulans* gpdA gene, a *Trichoderma reesei* cbh gene, preferably cbh1. According to another preferred embodiment, the highly expressed genes are the loci of SEQ ID NOs 1, 13, 16 or SEQ ID NO: 19. More than one copy of a nucleic acid sequence encoding a polypeptide may be inserted into the host cell to increase production of the gene product. This can be done, preferably by integrating into its genome copies of the DNA sequence, more preferably by targeting the integration of the DNA sequence at one of the highly expressed locus defined in the former paragraph. Alternatively, this can be done by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent. To increase even more the number of copies of the DNA sequence to be over expressed the technique of gene conversion as described in WO98/46772 may be used.

The vector system may be a single vector or plasmid or two or more vectors or plasmids, which together contain the total DNA to be introduced into the genome of the filamentous fungal cell, or a transposon.

The vectors preferably contain one or more selectable markers, which permit easy selection of transformed cells. A selectable marker is a gene the product of which provides for biocide or viral resistance, resistance to heavy metals, prototrophy to auxotrophs, and the like. A selectable marker for use in a filamentous fungal cell may be selected from the group including, but not limited to, amdS (acetamidase), argB (ornithine carbamoyltransferase), bar (phosphinothricinacetyltransferase), bleA (phleomycin binding), hygB (hygromycinphosphotransferase), niaD (nitrate reductase), pyrG (orotidine-5'-phosphate decarboxylase), sC (sulfate adenyltransferase), and trpC (anthranilate synthase), as well as equivalents from other species. Preferred for use in an *Aspergillus* and *Penicillium* cell are the amdS (EP 635574 B1, WO 97/06261) and pyrG genes of *A. nidulans* or *A. oryzae* and the bar gene of *Streptomyces hygroscopicus*. More preferably an amdS gene is used, even more preferably an amdS gene from *A. nidulans* or *A. niger*. A most preferred selection marker gene is the *A. nidulans* amdS coding sequence fused to the *A. nidulans* gpdA promoter (see EP 635574 B1). AmdS genes from other filamentous fungi may also be used (WO 97/06261).

The procedures used to ligate the elements described above to construct the recombinant expression vectors of the present invention are well known to one skilled in the art (see, e.g., Sambrook et al., 1989, supra).

Host Cells

All the transcriptional activators of the invention are preferably used for designing two types of host cells:

first type of host cell would be highly suited for producing a desired polypeptide, said desired polypeptide being sensitive to protease degradation, and second type of host cell would be highly suited for producing a polypeptide, said polypeptide being under the control of the transcriptional activator of the invention.

Optionally, both types of host cells additionally comprise an expression construct or a nucleic acid construct comprising a nucleic acid sequence coding for a polypeptide to be produced: polypeptide sensitive to protease degradation or polypeptide being under the control of the transcriptional activator or the transcriptional activator itself.

Optionally, the host cell comprises an elevated unfolded protein response (UPR) to enhance production abilities of a polypeptide of interest. UPR may be increased by techniques described in US2004/0186070A1 and/or US2001/0034045A1 and/or WO01/72783A2. More specifically, the protein level of HAC1 and/or IRE1 and/or PTC2 has been modulated in order to obtain a host cell having an elevated UPR.

The choice of a host cell in the invention will to a large extent depend upon the source of the nucleic acid sequence encoding the desired polypeptide to be produced. Preferably, the host cell is a filamentous fungus as defined earlier in section nucleic acid sequences encoding transcriptional activators of a protease promoter or in WO 01/68864 or WO 00/20596.

The introduction of an expression vector or a nucleic acid construct into a filamentous fungal cell may involve a process consisting of protoplast formation, transformation of the protoplasts, and regeneration of the cell wall in a manner known per se. Suitable procedures for transformation of *Aspergillus* cells are described in EP 238 023 and Yelton etal., 1984, Proceedings of the National Academy of Sciences USA 81 : 1470-1474. A suitable method of transforming. *Fusarium* species is described by Malardier et. al., 1989, Gene 78 : 147156 or in WO 96/00787. The expression vector or nucleic acid construct that can be used were already described under the corresponding sections.

In a more preferred embodiment, a transcriptional activator of a protease promoter of the invention is obtained from an *A. niger* strain, more preferably from *Aspergillus niger* AB4. 1 (van Hartingsveldt, W., et al., 1987. Mol. Gen. Genet. 206 : 71-75), and most preferably from *A. niger* CBS 513.88 or a mutant strain thereof, harbouring, e.g., the polypeptide with the amino acid sequence of SEQ ID NO: 3.

According to another preferred embodiment, a transcriptional activator of a protease promoter of the invention is obtained from one of the following deposited strains: *A. oryzae* ATCC 20423, IFO 4177, ATCC 1011, ATCC 9576, ATCC14488-14491, ATCC 11601, ATCC12892, *A. fumigatus* Af 293 (CBS 101355), or *P. chrysogenum* CBS 455.95 harbouring, e.g., the polypeptide with the amino acid sequence of SEQ ID NOs: 15, 18 and SEQ ID NO: 21, respectively.

Host Cell Suited for Production of a Polypeptide Sensitive to Protease Degradation According to a preferred embodiment, the invention relates to a filamentous fungal host cell which is a mutant of a parent filamentous fungal cell useful for the production of a polypeptide sensitive to protease degradation, in which the parent cell comprises one or more nucleic acid (DNA) sequences encoding a protease, the transcription of which is activated by a transcriptional activator of the invention, and the mutant cell produces less of the transcriptional activator and/or the protease(s) than the parent cell when cultured under the same conditions as preferably measured by a protease activity assay as described in the description earlier on or as follows.

A preferred method for measurement of protease activity in a host cell is described in the example section herein for determination of the acidic endo-protease activity using Bovine Serum Albumin (BSA) as substrate. A detailed description of this method is also described by van den Hombergh et al., Current Genetics 28: 299-308 (1995). Measurement of protease(s) also may be assayed using other known methods. In one such method, an aliquot of a 48 hour culture media is incubated with 3H-labelled sperm whale myoglobin at pH 4. 0 and the radioactivity in the TCA-soluble fraction is measured (van Noort, J. M., etal., 1991. Anal. Biochem 198 : 385-390). Other methods have been described for identifying, e. g., aspartic proteinase A. of *A. niger* (Takahashi, K., 1991. Meth. in Enzymol. 248 : 146-155), endopeptidases (Morihara, K., 1995. Meth. in Enzymol. 248 : 242-253), carboxypeptidases (Reminton, J., and Breddam, K., 1994. Meth. in Enzymol. 244 : 231-248), dipeptidyl peptidase (Ikehara, Y., etal., 244 : 215-227), and aminopeptidases (Little, G., et al., 1976. Meth. in Enzymol. 45 : 495-503). Alternatively other protease assays may be used such as the one described in WO 02/068623. Alternatively, the assay used may be a northern blotting (in Molecular Cloning: A Laboratory Manual, Sambrook et a/1989), the use of a reporter gene under the control of a protease promoter, or a western blotting or a DNA array analysis (Eisen, M. B. and Brown, P. O. DNA arrays for analysis of gene expression. Methods Enzymol. 1999:303:179-205) as also decribed herein.

According to a preferred embodiment, the mutant cell has a modified or an inactivated endogenous transcriptional activator of a protease promoter or an endogenous transcriptional activator, which has been replaced with a deteriorated transcriptional activator. According to another preferred embodiment, the mutant expresses a transcriptional activator of a protease promoter, which transcriptional activity can be modulated.

According to another preferred embodiment, the mutant cell *A. niger* produces less of the transcriptional activator and/or less protease(s) than the deposited cell CBS 513.88 as measured by any one of the given assays. According to another preferred embodiment, the mutant cell *Aspergillus oryzae* produces less of the transcriptional activator and/or less protease(s) than the deposited *A. oryzae* cited earlier. According to another preferred embodiment, the mutant cell *Penicillium chrysogenum* produces less of the transcriptional activator and/or less protease(s) than CBS 455.95. According to another preferred embodiment, the mutant cell *Aspergillus fumigatus* produces less of the transcriptional activator and/or less protease(s) than *Aspergillus fumigatus* AF293 (CBS101355).

Such a mutant cell may be obtained by genetic manipulation by one of the following techniques or by a combination thereof:
a. using recombinant genetic manipulation techniques,
b. submitting the filamentous fungus to mutagenesis.

Alternatively or in combination with above-mentioned techniques and according to another preferred embodiment, the mutant may be obtained by submitting the filamentous fungus to an inhibiting compound/composition.

The filamentous fungus obtained may be subsequently selected by monitoring the expression level of the nucleic acid sequence of the invention and/or the nucleic acid sequence of any protease known to be under control of the transcriptional activator of the invention. Optionally, the filamentous fungus is subsequently selected by measuring the expression level of a given gene of interest to be expressed in the host cell. More preferably, the mutant is made with recombinant genetic manipulation techniques such as defined in step a. to obtain a recombinant filamentous fungus. Most preferably step a. comprises deleting the DNA sequence encoding the transcriptional activator, even most preferably the deleted DNA sequence is replaced by a non-functional variant thereof, and even most preferably the deletion and replacement are made by gene replacement preferably as described in EP 357127 B.

In a preferred embodiment the mutant cell is obtained by modification or inactivation of a nucleic acid sequence present in the cell and necessary for expression of the transcriptional activator.

In another preferred embodiment the reduced expression of the transcriptional activator and/or protease in the mutant cell is obtained by modification or inactivation of a control sequence required for the expression of the transcriptional activator. The term "control sequence" is defined, supra, in the section entitled "Nucleic Acid Constructs". In a more preferred embodiment the control sequence in the mutant cell is a promoter sequence or a functional part thereof, i. e., a part, which is sufficient for affecting expression of the nucleic acid sequence. Other control sequences for possible modification include, but are not limited to, a leader, a polyadenylation sequence, a regulatory sequence and a transcription terminator.

In yet another preferred embodiment the reduced expression of the transcriptional activator and/or protease in the mutant cell is obtained by modification of the initiation codon (ATG) into a sub-optimal initiation codon.

Modification or inactivation of the nucleic acid sequence encoding the transcriptional activator of the invention may be performed by subjecting the parent cell to mutagenesis and selecting for mutant cells in which the capability to produce a transcriptional activator has been reduced by comparison to the parental cell. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet(W) irradiation, hydroxylamine,N-methyl-N'-nitro-N-nitrosoguanidine (MNNG), 0-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and selecting for mutant cells exhibiting reduced expression of the gene.

Alternatively, modification or inactivation of the gene may be performed by established anti-sense techniques using a nucleotide sequence complementary to the nucleic acid sequence of the gene. More specifically, expression of the gene by a filamentous fungal cell may be reduced or eliminated by introducing a nucleotide sequence complementary to the nucleic acid sequence, which may be transcribed in the cell and is capable of hybridizing to the mRNA produced in the cell. Under conditions allowing the complementary antisense nucleotide sequence to hybridize to the mRNA, the amount of protein translated is thus reduced or eliminated. An example of expressing an antisense-RNA is shown in Appl Environ Microbiol. 2000 February; 66(2):775-82. (Characterization of a foldase, protein disulfide isomerase A, in the protein secretory pathway of *Aspergillus niger*. Ngiam C, Jeenes D J, Punt P J, Van Den Hondel C A, Archer D B) or (Zrenner R, Willmitzer L, Sonnewald U. Analysis of the expression of potato uridinediphosphate-glucose pyrophosphorylase and its inhibition by antisense RNA. Planta. (1993);190(2):247-52.).

Furthermore, modification, downregulation or inactivation of the gene may be obtained via the RNA interference (RNAi) technique (FEMS Microb. Lett. 237 (2004): 317-324). In this method identical sense and antisense parts of the nucleotide sequence, which expression is to be affected, are cloned behind each other with a nucleotide spacer in between, and inserted into an expression vector. After such a molecule is transcribed, formation of small (21-23) nucleotide fragments will lead to a targeted degradation of the mRNA, which is to be affected. The elimination of the specific mRNA can be to various extends. The RNA interference techniques described in WO2005/05672A1 and/or WO2005/026356A1 may be used for downregulation, modification or inactivation of the gene.

In another preferred embodiment, the filamentous fungus mutant cell harbours a nucleic acid sequence, which has been modified or inactivated by any of the methods described above and produces less of a protease or a combination of proteases than the filamentous fungus parent cell when cultured under identical conditions as measured using the same assays as defined before. The mutant cell produces preferably at least about 25% less, more preferably at least about 50% less, even more preferably at least about 75% less, and even more preferably at least about 95% less of a protease or a combination of proteases than the parent cell when cultured under identical conditions using the same assays as defined before. According to a preferred embodiment, the filamentous fungus *Aspergillus niger* or *Aspergillus oryzae* or *Aspergillus fumigatus* or *Penicillium chrysogenum* mutant cell produces less of a protease or a combination of protease than the corresponding deposited filamentous fungus cell cited earlier when cultured under identical conditions using the same assays as defined before.

In an even more preferred embodiment, the filamentous fungus mutant cell produces essentially undetectable amounts of a protease or combination of proteases than the parent cell when cultured under identical conditions using the same assays as defined before.

In a most preferred embodiment, the filamentous fungus mutant cell produces less or essentially undetectable amounts of a protease or combination of proteases than the parent cell when cultured under identical conditions as described above using the assay for determination of the acidic endo-protease activity using Bovine Serum Albumin (BSA) as substrate as defined and referenced before herein.

In another preferred embodiment, the filamentous fungus mutant cell harbours at least one copy of a nucleic acid sequence encoding a polypeptide of interest (see section producing a polypeptide).

Host Cell Suited for Protease Production

According to another preferred embodiment, the invention relates to a host cell highly suited for the production of a polypeptide wherein the host cell is a mutant of a parent cell in which the mutant (a) produces more of the transcriptional activator of the present invention as compared to the parent cell when cultured under the same conditions and using the same assay as defined in the former section; and (b) comprises a DNA sequence encoding the polypeptide, the transcription of which is activated by the transcriptional activator.

According to another preferred embodiment, the mutant cell *A. niger* produces more of the transcriptional activator and/or more protease(s) than the deposited cell CBS 513.88 when cultured under identical conditions and as measured by one of the given assays defined in the former section. A preferred method for measurement of protease activity in a host cell is described in the example section herein for determination of the acidic endo-protease activity using Bovine Serum Albumin (BSA) as substrate. According to another preferred embodiment, the mutant cell *Aspergillus oryzae* produces more of the transcriptional activator and/or more protease(s) than the deposited *A. oryzae* cited earlier when cultured under identical conditions and as measured by one of the given assays defined in the former section. According to another preferred embodiment, the mutant cell *Penicillium chrysogenum* produces more of the transcriptional activator and/or more protease(s) than CBS 455.95 when cultured under identical conditions and as measured by one of the given assays defined in the former section. According to another preferred embodiment, the mutant cell *Aspergillus fumigatus* produces more of the transcriptional activator and/or more protease(s) than the deposited *A. fumigatus* cited earlier when cultured under identical conditions and as measured by one of the given assays defined in the former section.

In a preferred embodiment, the filamentous fungal host cell produces more of the transcriptional activator than the parent cell and/or more than any cited deposited parent cell when cultured under the same conditions by introducing into the parent cell one or more copies of (i) a nucleic acid sequence encoding a transcriptional activator of a protease promoter as isolated or having enhanced transcriptional activity on a protease promoter, (ii) a nucleic acid construct comprising a nucleic acid sequence encoding a transcriptional activator of a protease promoter, (iii) an expression vector as defined above in the section "Expression Vectors".

In a more preferred embodiment, the nucleic acid sequence encoding the transcriptional activator is operably linked to a promoter, or a functional part thereof, which is stronger than the corresponding promoter of the filamentous fungal parent cell. In an even more preferred embodiment, the promoter, or a functional part thereof, mediates the expression of a gene encoding an extracellular protease, such as the *A. oryzae* alkaline protease, *A. oryzae* neutral metalloprotease, *A. niger* aspergillopepsin protease, *Fusarium oxysporum* trypsin-like protease or *F. venenatum* trypsin.

The present invention also relates to a filamentous fungal host cell useful for the production of a polypeptide wherein the filamentous fungal host cell is a mutant of a parent filamentous fungal cell in which the mutant comprises a) a modification or inactivation of a transcriptional activator of the present invention, or a regulatory sequence thereof, and
b) (i) an inducible promoter operably linked to a nucleic acid sequence encoding a transcriptional activator of the present invention, and (ii) a promoter sequence to which the transcriptional activator can bind, operably linked to a nucleic acid sequence encoding the polypeptide, wherein (i) and (ii) can be introduced simultaneously or sequentially.

The inactive form of the transcriptional activator in (a) above can be obtained as described in the former section.

The inducible promoter sequence in (b) above may be any promoter sequence, or a functional part thereof, wherein the transcription initiation activity of the promoter can be induced according to the fermentation conditions. Preferably, the induction is mediated by a carbon or nitrogen catabolite. In a preferred embodiment, the promoter is the amdS promoter of *A. nidulans* or *A. oryzae*, the niaD promoter of *A. nidulans* or *A. niger, A. oryzae* or *A. niger*, the niiA promoter of *Aspergillus* species, the alkaline phosphatase promoter of *Aspergillus* sp., the acid phosphatase promoter of *Aspergillus* sp., or the alcA promoter of *A. niger, A. tubingensis* xylanase (xlnA) promoter.

In another preferred embodiment, the filamentous fungal host cell further comprises a promoter sequence, wherein the promoter sequence can be activated by the transcriptional activator and is operably linked to the nucleic acid sequence encoding the polypeptide.

The promoter sequence activated by the transcriptional activator of the present invention may be any promoter sequence, or a functional part thereof. Preferably, the promoter is from a protease gene. More preferably, the promoter is selected from the group, which includes but is not limited to promoters obtained from the genes encoding *A. oryzae* TAKA amylase, *Rhizomucor miehei* aspartic proteinase, *A. niger* neutral alpha-amylase, *A. niger* acid stable alpha-amylase, *A. niger* or *A. awamori* glucoamylase (glaA), *R. miehei* lipase, *A. oryzae* alkaline protease, *A. oryzae* triose phosphate isomerase, *A. nidulans* acetamidase, the NA2-tpi promoter (a hybrid of the promoters from the genes encoding *A. niger* neutral alpha-amylase and *A. oryzae* triose phosphate isomerase), and mutant, truncated, and hybrid promoters thereof. Particularly preferred promoters for use in filamentous fungal cells are a promoter, or a functional part thereof, from a protease gene; e. g., from the *F. oxysporum* trypsin-like protease gene (U.S. Pat. No. 4,288,627), *A. oryzae* alkaline protease gene(a/p), *A. niger* pacA gene, *A. oryzae* alkaline protease gene, *A. oryzae* neutral metalloprotease gene, *A. niger* aspergillopepsin protease pepA gene, or *F. venenatum* trypsin gene. *A. niger* aspartic protease pepB gene.

In another preferred embodiment, the filamentous fungal host cell harbours at least one copy of a nucleic acid sequence encoding a polypeptide.

The nucleic acid constructs described herein may be introduced into a parent fungal cell according to any of the methods as described supra in the section, "Host Cells" to obtain a host cell useful for the production of a polypeptide.

It will be understood that the methods of the present invention are not limited to a particular order for obtaining the mutant filamentous fungal cell. The modification of the second nucleic acid sequence may be introduced into the parent cell at any step in the construction of the cell for the production of a polypeptide.

Producing a Polypeptide

Another aspect of the present invention relates to methods of producing a polypeptide in a filamentous fungal host cell of the present invention, comprising:
(a) cultivating the filamentous fungal host cell which harbours a gene encoding the polypeptide in a nutrient medium suitable for production of the polypeptide and optionally;
(b) recovering the polypeptide from the nutrient medium of the filamentous fungal host cell.

According to a first preferred embodiment, the polypeptide produced is the transcriptional activator of the invention.

According to a second preferred embodiment, the polypeptide produced is a polypeptide sensitive to protease degradation. In this case, the first type of host cell (as described in "Host cell suited for production of a polypeptide sensitive to protease degradation") will be used.

According to a third preferred embodiment, the polypeptide to be produced is a polypeptide, whose expression is activated by the transcriptional activator of the invention. In this case, the second type (as described in "Host cell suited for protease production") of host cell will be used.

The filamentous fungal host cells of the present invention are cultivated in a nutrient medium suitable for production of the polypeptide of interest using methods known in the art. For example, the cells may be cultivated by shake flask cultivation, small-scale or large-scale fermentation (including continuous, batch, fedbatch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art (see, e. g., Bennett, J. W. and LaSure, L., eds., More Gene Manipulations in Fungi, Academic Press, CA, 1991). Suitable media are available from commercial suppliers or may be prepared using published compositions (e. g., in catalogues of the American Type Culture Collection). If the polypeptide is secreted into the nutrient medium, the polypeptide can be recovered directly from the medium. If the polypeptide is not secreted, it is recovered from cell lysates.

The resulting polypeptide may be isolated by methods known in the art. For example, the polypeptide may be isolated from the nutrient medium by conventional procedures including, but not limited to, centrifugation, filtration, extraction, spray drying, evaporation, or precipitation. The isolated polypeptide may then be further purified by a variety of procedures known in the art including, but not limited to, chromatography (e. g., ion exchange, affinity, hydrophobic, chromatofocusing, and size exclusion), electrophoretic procedures (e.g., preparative isoelectric focusing, differential solubility (e.g., ammonium sulfate precipitation), or extraction (see, e.g., Protein Purification, J.-C. Janson and Lars Ryden, editors, VCH Publishers, New York, 1989).

The polypeptide may be detected using methods known in the art that are specific for the polypeptide. These detection methods may include use of specific antibodies, formation of an enzyme product, disappearance of an enzyme substrate, or SDS PAGE. For example, an enzyme assay may be used to determine the activity of the polypeptide. Procedures for determining enzyme activity are known in the art for many enzymes.

In the methods of the present invention, the filamentous fungal host cell produces at least about 20% more, preferably at least about 50% more, more preferably at least about 100% more, even more preferably at least about 200% more, and most preferably at least about 300% more of the polypeptide than a corresponding parent cell when cultivated under the same conditions using one of the given assays. More preferably, the parent cell is one of the deposited strains cited earlier.

The polypeptide may be any polypeptide whether native or heterologous to the filamentous fungal cell. The term "heterologous polypeptide" is defined herein as a polypeptide, which is not produced by a wild-type filamentous fungal cell. The term "polypeptide" is not meant herein to refer to a specific length of the encoded produce and therefore encompasses peptides, oligopeptides and proteins. The polypeptide may also be a recombinant polypeptide, which is a polypeptide native to a cell, which is encoded by a nucleic acid sequence, which comprises one or more control sequences, foreign to the nucleic acid sequence, which is involved in the production of the polypeptide. The polypeptide may be a wild-type polypeptide or a variant thereof. The polypeptide may also be a hybrid polypeptide, which contains a combination of partial or complete polypeptide sequences obtained from at least two different polypeptides where one or more of the polypeptides may be heterologous to the cell. Polypeptides further include naturally occurring allelic and engineered variations of the above-mentioned polypeptides.

In a preferred embodiment, the polypeptide is an antibody or portions thereof, an antigen, a clotting factor, an enzyme, a hormone or a hormone variant, a receptor or portions thereof, a regulatory protein, a structural protein, a reporter, or a transport protein, intracellular protein, protein involved in secretion process, protein involved in folding process, chaperone, peptide amino acid transporter, glycosylation factor, transcription factor. In a preferred embodiment, the polypeptide is secreted extracellularly.

In a more preferred embodiment, the enzyme is an oxidoreductase, transferase, hydrolase, lyase, isomerase, ligase, catalase, cellulase, chitinase, cutinase, deoxyribonuclease, dextranase, esterase.

In an even more preferred embodiment, the polypeptide is a carbohrase, e.g. cellulases such as endoglucanases, β-glucanases, cellobiohydrolases or β-glucosidases, hemicellulases or pectinolytic enzymes such as xylanases, xylosidases, mannanases, galactanases, galactosidases, pectin methyl esterases, pectin lyases, pectate lyases, endo polygalacturonases, exopolygalacturonases rhamnogalacturonases, arabanases, arabinofuranosidases, arabinoxylan hydrolases, galacturonases, lyases, or amylolytic enzymes; hydrolase, isomerase, or ligase, phosphatases such as phytases, esterases such as lipases, proteolytic enzymes, oxidoreductases such as oxidases, transferases, or isomerases. More preferably, the desired gene encodes a phytase. In an even more preferred embodiment, the polypeptide is an aminopeptidase, amylase, carbohydrase, carboxypeptidase, endo-protease, metalloprotease, serine-protease catalase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, proteolytic enzyme, invertase, laccase, lipase, mannosidase, mutanase, oxidase, pectinolytic enzyme, peroxidase, phospholipase, polyphenoloxidase, ribonuclease, transglutaminase, or glucose oxidase, hexose oxidase, monooxygenase.

In another even more preferred embodiment, the polypeptide is human insulin or an analog thereof, human growth hormone, erythropoietin, tissue plasminogen activator (tPA) or insulinotropin.

The nucleic acid sequence encoding a heterologous polypeptide may be obtained from any prokaryotic, eukaryotic, or other source.

Alternatively the polypeptide may be an intracellular protein or enzyme such as for example a chaperone, protease or transcription factor. An example of this is described in Appl Microbiol Biotechnol. 1998 October; 50(4):447-54 ("Analysis of the role of the gene bipA, encoding the major endoplasmic reticulum chaperone protein in the secretion of homologous and heterologous proteins in black Aspergilli. Punt P J, van Gemeren I A, Drint-Kuijvenhoven J, Hessing J G, van Muijlwijk-Harteveld G M, Beijersbergen A, Verrips C T, van den Hondel C A). This can be used for example to improve the efficiency of a host cell as protein producer if this polypeptide, such as a chaperone, protease or transcription factor, was known to be a limiting factor in protein production.

For purposes of the present invention, the term "obtained from "as used herein in connection with a given source shall mean that the polypeptide is produced by the source or by a cell in which a gene from the source has been inserted.

In the methods of the present invention, the filamentous fungal cells may also be used for the recombinant production of polypeptides, which are native to the cell. The native polypeptides may be recombinantly produced by, e.g., placing a gene encoding the polypeptide under the control of a different promoter to enhance expression of the polypeptide, to expedite export of a native polypeptide of interest outside the cell by use of a signal sequence, and to increase the copy number of a gene encoding the polypeptide normally produced by the cell. The present invention also encompasses, within the scope of the term "heterologous polypeptide", such recombinant production of polypeptides native to the cell, to the extent that such expression involves the use of genetic elements not native to the cell, or use of native elements which have been manipulated to function in a manner that do not normally occur in the filamentous fungal cell. The techniques used to isolate or clone a nucleic acid sequence encoding a heterologous polypeptide are known in the art and include isolation from genomic DNA, preparation from cDNA, or a combination thereof.

In the methods of the present invention, heterologous polypeptides may also include a fused or hybrid polypeptide in which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide.

Techniques for producing fusion polypeptides are known in the art, and include, ligating the coding sequences encoding the polypeptides so that they are in frame and expression of the fused polypeptide is under control of the same promoter (s) and terminator. The hybrid polypeptides may comprise a combination of partial or complete polypeptide sequences obtained from at least two different polypeptides wherein one or more may be heterologous to the mutant fungal cell. An isolated nucleic acid sequence encoding a heterologous polypeptide of interest may be manipulated in a variety of ways to provide for expression of the polypeptide. Expression will be understood to include any step involved in the production of the polypeptide including, but not limited to, transcription, posttranscriptional modification, translation, post-translational modification, and secretion. Manipulation of the nucleic acid sequence encoding a polypeptide prior to its insertion into a vector may be desirable or necessary depending on the expression vector. The techniques for modifying nucleic acid sequences utilizing cloning methods are well known in the art.

The present invention is further described by the following examples, which should not be construed as limiting the scope of the invention.

EXAMPLES

Experimental Information
Strains
WT 1: This *A. niger* strain is used as a wild-type strain. This strain is deposited at the CBS Institute under the deposit number CBS 513.88.

WT 2: This *A. niger* strain is a WT 1 strain comprising a deletion of the gene encoding glucoamylase (glaA). WT 2 was constructed by using the "MARKER-GENE FREE" approach as described in EP 0 635 574 B1. In this patent it is extensively described how to delete glaA specific DNA sequences in the genome of CBS 513.88. The procedure resulted in a MARKER-GENE FREE ?glaA recombinant *A. niger* CBS 513.88 strain, possessing finally no foreign DNA sequences at all.

WT 3: This *Penicillium chrysogenum* strain is used as a wild-type strain. This strain is deposited at the CBS Institute under the deposit number CBS 455.95.

Plasmids
pGBFINPRT-1: This prtT expression construct (depicted in FIG. 3) was deposited at the CBS Institute under the accession number CBS118680.

pGBPRT-1: This prtT cDNA vector (depicted in FIG. 19) was deposited at the CBS Institute under accession number CBS118681.

*A. niger* Shake Flask Fermentations

*A. niger* strains were precultured in 20 ml preculture medium as described in the Examples: "*Aspergillus niger* shake flask fermentations" section of WO99/32617. After overnight growth, 10 ml of this culture was transferred to fermentation medium 1 (FM1) with 7% glucose as described in WO99/32617. This FM1 contains per liter: 25 g Caseinhydrolysate, 12.5 g Yeast extract, 1 g KH2PO4, 2 g K2SO4, 0.5 g MgSO4.7H2O, 0.03 g ZnCl2, 0.02 g CaCl2, 0.01 g MnSO4.4H2O, 0.3 g FeSO4.7H2O, 10 ml Pen-Strep. (5000 IU/ml Pen-5 mg/ml Strep), adjusted to pH 5.6 with 4 N H2SO4. Fermentation is performed in 500 ml flasks with baffle with 100 ml fermentation broth at 34° C. and 170 rpm for the number of days indicated.

For protease induction, mycelia were harvested after culturing for 16-24 h in FM1, washed at room temperature with Induction Medium (IM) and transferred to IM with C-source as indicated.

Induction Medium (IM) Contains Per Liter:
6 g NaNO3, 0.5 g KCl, 1.5 g KH2PO4, 1.13 ml 4M KOH, 0.5 g MgSO4.7H2O, 0.01% (w/v) casamino acids, 0.1% (w/v) yeast extract, 1 ml of stock trace elements (stock trace elements per liter: 22 g ZnSO4.7H2O, 11 g H3BO3, 5 g FeSO4.7H2O, 1.7 g CoCl2.6H2O, 1.6 g CuSO4.5H2O, 5 g MnCl2.4H20, 1.5 g Na2Mo04.2H2O, 50 g EDTA, adjust the pH to 6.5 with 4M KOH, filter sterilize and store in the dark at 4° C.), 10 ml of stock vitamins (stock vitamins per liter: 200 mg riboflavin, 200 mg thiamine.HCl, 200 mg nicotinamide, 100 mg pyridoxine.HCl, 20 mg panthotenic acid, 0.4 mg biotin, adjust to pH 6 with 4M NaOH, filter sterilize and store in the dark at 4° C.), and adjusted to pH 5.6. Fermentation medium 2 (FM2) is used for PLA2 fermentations and contains per liter: 82.5 g Giucose.1 H2O, 25 g Maldex 15 (Boom Meppel, Netherlands), 2 g Citric acid, 4.5 g NaH2PO4.1H2O, 9 g KH2PO4, 15 g (NH4)2SO4, 0.02 g ZnCl2, 0.1 g MnSO4.1H2O, 0.015 g CuSO4.5H2O, 0.015 g CoCl2.6H2O, 1 g MgSO4.7H2O, 0.1 g CaCl2.2H2O, 0.3 g FeSO4.7H2O, 30 g MES (2-[N-Morpholinojethanesulfonic acid), pH=6.

Oligonucleotide Sequences

All primers used in the experiments are described in the sequence listing under the SEQ ID numbers 5-12 and 23-24.

Protease Activity Assays

Total acidic endo-protease activities in culture supernatants were determined as the amount of degraded BSA. 450 µl 1% (w/v) BSA in 0.1 M NaAc pH 4.0 was incubated with 50 µl culture supernatant at 37 degrees Celsius for different time intervals. At the end of the incubation period, the remainder of the BSA was precipitated with 500 µl 10% (w/v) trichloracetic acid (TCA) and followed by incubation on ice for 10 min. The precipitate was centrifuged for 10 min at 13000 rpm in an Eppendorf centrifuge. The absorbance of the supernatant was measured at 280 nm. One unit of protease activity was defined as the change in absorbance units at 280 nm per hour (Anson assay). A more detailed description and references for this method is also described by van den Hombergh et al., Current Genetics 28: 299-308 (1995).

Exo-protease activities in culture supernatants were determined using specific peptides attached to a colour group (p-nitroanilide (pNA) or 3-(2-furyl)acryloyl (FA)). Exo-protease activity releases the pNA or FA from the peptide, which causes a change in absorbance. 450 µl of the 0.2 mM substrate solution in water was incubated with 50 µl culture supernatant at room temperature. pNA-substrates were measured at 405 nm (pH 6-7); FA-substrates were measured at 332 nm (~pH 5). The absorbance of pNA-substrates increases upon release of the pNA-group; the absorbance of FA-substrates decreases upon release of the FA-group. The protease activity in units is calculated as the change in absorbance per hour.

Assaying proteolytic activity and the different protease activities in general is described in WO 02/068623.

Protease Plate Assay

To screen for enhanced or decreased proteases expression, minimal medium plates containing dialyzed skim milk were used as described by Mattern et al. (Mol. Gen. Genet. 1992, 234:332-336). The *A. niger* WT 1 and WT 2 are producing a clear halo on this medium after 4 days incubation at 30° C.

PLA2 Phospholipase Activity

To determine phospholipase PLA2 activity (PLA2) in *Aspergillus niger* culture broth spectrophotometrically, an artificial substrate is used: 1,2-dithiodioctanoyl phophatidylcholine (diC8, substrate). PLA2 hydrolyses the sulphide bond at the A2 position, dissociating thio-octanoïc acid. Thio-octanoïc acid reacts with 4,4 dithiopyridine (color reagent, 4-DTDP), forming 4-thiopyridone. 4-Thiopyridone is in tautomeric equilibrium with 4-mercaptopyridine, which absorbs radiation having a wavelength of 334 nm. The extinction change at that wavelength is measured. One unit is the amount of enzyme that liberates of 1 nmol thio-octanoic acid from 1,2-dithiodioctanoyl phosphatidylcholine per minute at 37° C. and pH 4.0.

The substrate solution is prepared by dissolving 1 g diC8 crystals per 66 ml ethanol and add 264 ml acetate buffer. The acetate buffer comprises 0.1 M Acetate buffer pH 3.85 containing 0.2% Triton-X100. The colour reagent is a 11 mM 4,4-dithiodipyridine solution. It was prepared by weighting 5.0 mg 4,4-dithiodipyridine in a 2 ml eppendorf sample cup and dissolving in 1.00 ml ethanol. 1.00 ml of milli-Q water was added.

Example 1

Construction of an *A. niger* cDNA Expression Library and Isolation of a prtT cDNA Clone This example describes the construction of an expression library in an expression vector. The pool of mRNA's is isolated from mycelium grown under inducing conditions for protease activity. After construction, the expression library is used for isolation of a prtT cDNA clone.

1.1 Construction of a cDNA Library Induced for Protease Activity

In the following example, the induction of the proteolytic system in *A. niger* is determined by measuring a number of proteolytic activities in the culture broth.

Figure 1:
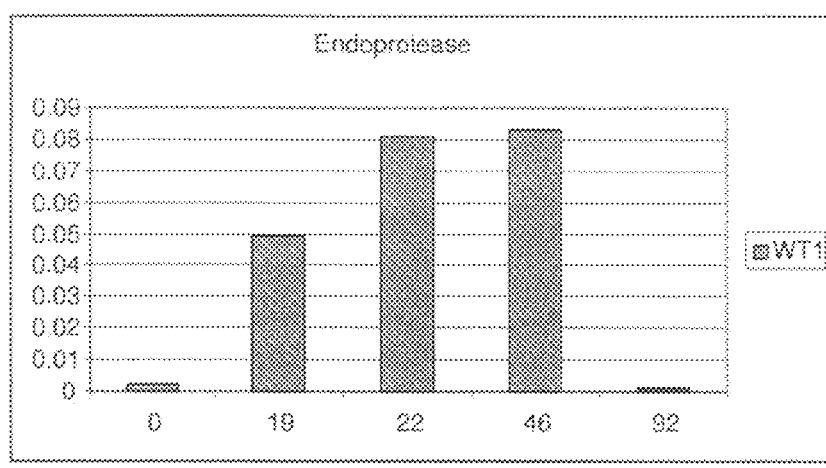
FIG. 1 Endoprotease activity in supernatant of the WT1 strain grown in IM supplemented with 2% defatted soy flour. Activity on the Y-axis is the endoprotease activity determined in U/50 µl supernatant per h. The X-axis indicates culture time in h after transfer to IM.

*A. niger* strain WT 1 was used to perform shake flask experiments in 100 ml of the medium as described herein at 34° C. and 170 rpm in an incubator shaker using a 500 ml baffled shake flask. *A. niger* WT 1 was pre-cultured overnight and subsequently the mycelium was transferred to Fermentation Medium 1 (FM1). After 20 h of growth the mycelium was shifted to Induction Medium (IM), containing 1% (w/v) collagen or 2% (w/v) defatted soy flour (see Experimental Information). The growth was continued for 4 days. Samples were collected to determine protease activities, as described above. In FIG. 1, endoprotease activities for the soy flour culture are given. A clear induction of endoproteases is shown upon growth on soy flour. A similar profile was found for the collagen culture (data not shown).

Additionally, exo-protease activities were measured for different time-points for the two C-sources. For both collagen and soy flour a clear induction of exo-proteases was found after 2 days of growth (data not shown).

Figure 2:
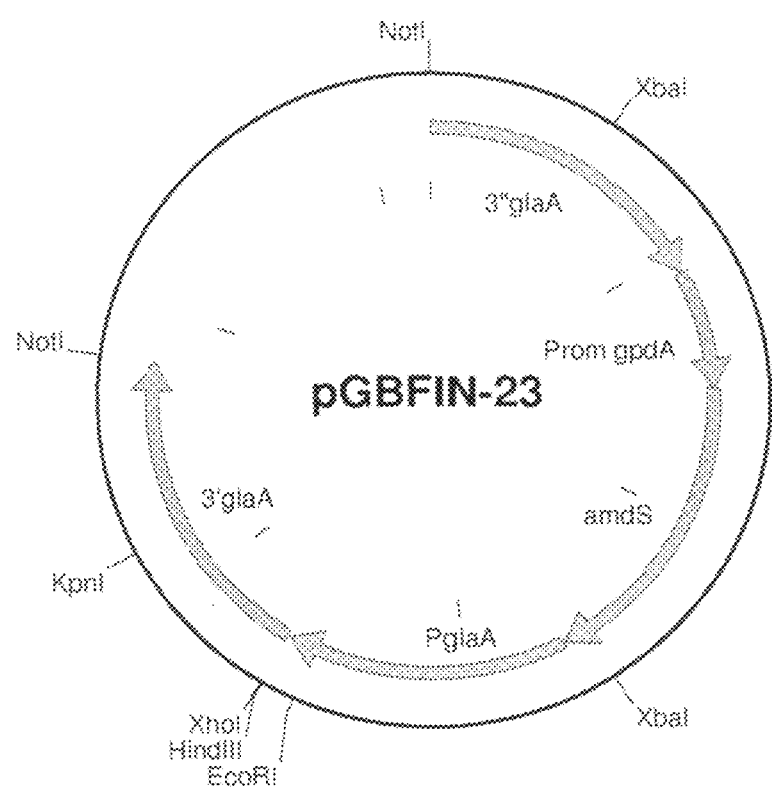
FIG. 2 Plasmid map of expression vector pGBFIN-23. Indicated are the glaA flanking regions relative to the glaA promoter and HindIII-XhoI cloning site. The *E. coli* DNA can be removed by digestion with restriction enzyme NotI, prior to transformation of the *A. niger* strains.

Mycelia harvested 18, 28 and 48 h after the shift to IM containing 1% (w/v) collagen or 2% (w/v) defatted soy flour were used for RNA extractions. The RNA extractions and mRNA isolations were performed as described in detail in WO99/32617. The construction of a cDNA expression library comprising a.o. the cDNA synthesis, the ligation of linkers and *E. coli* transformation is described as well in WO99/32617. Linkers used for the cDNA reactions consisted of a Hind III and XhoI restriction sites. The resulting cDNA pools were ligated in the HindIII-XhoI digested pGBFIN-23 vector, which construction and use is described in WO99/32617. A physical map of pGBFIN-23 can be found in FIG. 2. The ligation mixtures were used to transform DH10B electrocompetent cells (invitrogen) resulting in the generation of over $10^5$ colonies per cDNA library obtained from both the soy flour and the collagen induced mycelium. Random sequencing of 96 clones of each of the two libraries indicated a low percentage of vectors without insert. The insert sizes for the clones sequenced were between 0.5-4.7 kb with an average of 1.7 kb. To enable an efficient screening format, the library was constructed in pools of $10^3$ clones. For each of these pools, glycerol stocks were made and stored for later use.

1.2 Transformation of *A. niger* WT 2 with an Expression Library

For 20 pools of the cDNA library (10 originating from the soy flour and 10 from the collagen induced library), plasmid DNA was isolated according to known principles and routine plasmid isolation techniques (Sambrook, J. et al., 1989). For each of the pools, 5 µg of total plasmid DNA was digested for 4 hours at 37° C. with NotI (20 U), to remove E. coli derived plasmid sequences.

For each of the 20 pools, an A. niger WT 2 transformation was performed using the E. coli-free linear fragments containing A. niger cDNA clones. Per pool, 1000 colonies were purified on selective medium containing acetamide and transferred to individual wells in a 96 well microtiter dish, all as described in WO99/32617

1.3 Analysis of the A. niger Expression Library

All individual transformants were tested using the protease plate assay as described above. Conidiospores of individual transformants were transferred to the minimal medium plates containing dialyzed skim milk. After 2-3 days of incubation at 30° C., halo formation could be observed for 29 colonies, indicating increased protein degradation. For all other transformants a halo started to appear after 4-6 days. At day 5, the halo for the 29 colonies was also larger in size when compared to WT 2.

The 29 positively identified transformants originated from 14 different pools of the library. To be able to analyse independent transformants, conidiospores for 14 positive transformants originating from different pools of the expression library were isolated and used to inoculate PDA plates.

For strain WT 2 and the 14 selected transformants, shake flask experiments were performed as described in more detail in EP 635 574 B1. Essentially, mycelium was grown in 100 ml medium at 34° C. and 170 rpm in an incubator shaker using a 500 ml baffled shake flask. After 2 and 4 days of fermentation, samples were taken to determine protease activities as described in Experimental Information. For all selected transformants, the total acid extracellular protease activity was increased compared to WT 2 in both time points examined (data not shown).

For the 14 selected transformants, genomic DNA was isolated from single colonies.

1.4 Isolation of a cDNA Expression Clone Containing a Protease Transcriptional Activator PrtT In essence, the pGBFIN-23 based expression vector used in the construction of the expression library (FIG. 2) comprises the glucoamylase promoter, a variable cDNA coding sequence operably linked to the promoter and the glucoamylase terminator region, flanked by the 3' and 3" glaA targeting sites, and the amdS selection marker in an E. coli vector. Therefore, specific, but unknown, cDNA sequences in a WT 2 transformant, which carries a deletion of the endogenous glucoamylase region, can be identified using PCR and two glucoamylase-specific primers. One based on the standard glucoamylase promoter and another on the glucoamylase terminator region. Using 100 ng of the genomic DNA, PCR was performed with the 14 selected A. niger transformants using the glucoamylase-specific oligonucleotides identified as SEQ ID NO 23 and SEQ ID NO 24. For 11 of the transformants, a band could be amplified using PCR. These bands were cloned in pCR2.1-TOPO (Invitrogen) and sequenced. Six of the cDNA clones contained an identical cDNA sequence. The ORF of this cDNA sequence is shown in the sequence listings under the SEQ ID NO 2. To the polypeptide sequence encoded by SEQ ID NO 2, the SEQ ID NO 3 has been assigned.

Using 10 ng of plasmid DNA of six positive pools and cDNA-specific oligonucleotides identified as SEQ ID NO 5 and SEQ ID NO 6, all pools tested were found positive showing the presence of a band of about 500 bp using PCR. Subsequently, the glycerol stocks for a number of positive pools were used to plate colonies. These colonies were screened by colony hybridization and the 500 bp probe and the clones containing a hybridizing insert, named prtT, were isolated according standard techniques as described in Sambrook et al.,1989 (see above). In FIG. 3, a physical map for a representative isolated clone, which is named pGBFINPRT-1, is presented. Sequences of several prtT clones obtained by sequencing of pGBFINPRT plasmids were aligned (data not shown). The alignment showed that all the sequenced plasmids contained the cDNA insert (identified as SEQ ID NO 2) encoding the identical protein PrtT (identified as SEQ ID NO 3).

Example 2

Identification of prtT Genes

Genomic DNAs of the A. niger WT 1 and the P. chrysogenum WT 3 strains were sequenced and analyzed. Using the SEQ ID NO 2 in a search against these genomes, the genomic sequences of the A. niger prtT and P. chrysogenum prtT genes were determined. The SEQ ID NO 1 was assigned to the A. niger prtT genomic sequence and the SEQ ID NO 19 was assigned to the P. chrysogenum prtT genomic sequence. The genomic sequence of the A. niger prtT locus comprises the ORF and approximately 3000 bp of the 5' untranslated region (UTR) and 1700 bp of the 3' UTR and the P. chrysogenum genomic sequence contains the ORF and 574 bp of the 5'UTR and 238 by of the 3'UTR. The nucleotide sequence encoding the PrtT protein of P. chrysogenum is shown in the sequence listings under the SEQ ID NO 20. The translated sequence of the SEQ ID NO 20 is assigned as the SEQ ID NO 21 and it represents the amino acid sequence of the transcriptional activator PrtT of P. chrysogenum WT 3.

Example 3

Alignment of Novel cDNA Sequences and the Encoded Proteins

Example 3.1

Alignment of Polypeptide Sequences with the PrtT Polypeptide of SEQ ID NO 3

A search was performed against a nucleotide sequence patent database with the SEQ ID NO 2. Two publications (WO 00/20596 and WO 01/68864) were identified, which deal with PrtT. In order to examine the extent of the sequence identity among the PrtT proteins, the PrtT polypeptide sequences of A. niger and A. oryzae described in above mentioned publications were aligned with the PrtT sequence SEQ ID NO 3 of this invention (see FIG. 4 and FIG. 5). Surprisingly, it became clear from these alignments that the SEQ ID NO 3 of PrtT of A. niger WT 1 is different from both polypeptide sequences published earlier. The alignment presented in FIG. 4 identified 45 amino acid differences between the A. niger WT 1 PrtT sequence and the A. niger polypeptide sequence published in WO 00/20596 and WO 01/68864. These differences were caused by one amino acid substitution in the N-terminal part and by differences in the identified ORFs, i.e. the A. niger WT 1 prtT sequence comprises an additional intron in the 3' of the coding sequence, and the A. niger WT1 prtT sequence is missing the last exon identified in the A. niger prtT sequence of WO 00/20596 and WO 01/68864. More substantial differences were found between PrtT of A. niger WT 1 and A. oryzae PrtT sequence published in WO 01/68864 (see FIG. 5). The polypeptide sequences in FIG. 4 have 93% match percentage, i.e. identity, as identified using the CDA method (Huang, 1994) with settings as described in the text and the sequences in the FIG. 5 have 49% match percentage, i.e. identity. See FIG. 5 for more detail.

Example 3.2

In Silico Analysis of the *A. niger* PrtT Polypeptide

In order to obtain a prediction of functional domains of the PrtT transcriptional activator of *A. niger* WT 1, the SEQ ID NO 3 was analyzed using several web domain databases: Two Regions were Predicted:
  (i) using Pfam (Sonnhamer EL et al, (1997), Pfam: a comprehensive database of protein families based on seed alignments. Proteins. 28:405-420), a motif having similarity to a Zn(II)2-Cys6 binuclear cluster DNA binding motif was found, and
  (ii) using Prosite (Bairoch A, et al, (1996), The PROSITE database, its status in 1995. Nucleic Acids Res., 24:189-196) a Leucine zipper motif was found (see FIG. 4).
  The later motif is known to be a functional domain responsible for dimerization that is found in several transcription factor families (Bauer-Bornberg, E., Rivals, E., and Vingron, M. (1998) Nucl. Acid Res. 26 (11): 2740-2746). The SEQ ID NO 4 is assigned to the predicted Zn(II)2-Cys6 binuclear cluster DNA binding domain of the PrtT transcriptional activator of *A. niger* WT 1.

Example 4

Overexpression of the prtT Gene in *A. niger* by Transformation with the pGBFINPRT-1 Construct In the following example, an expression construct is introduced in a fungal host cell by transformation.

Figure 6:
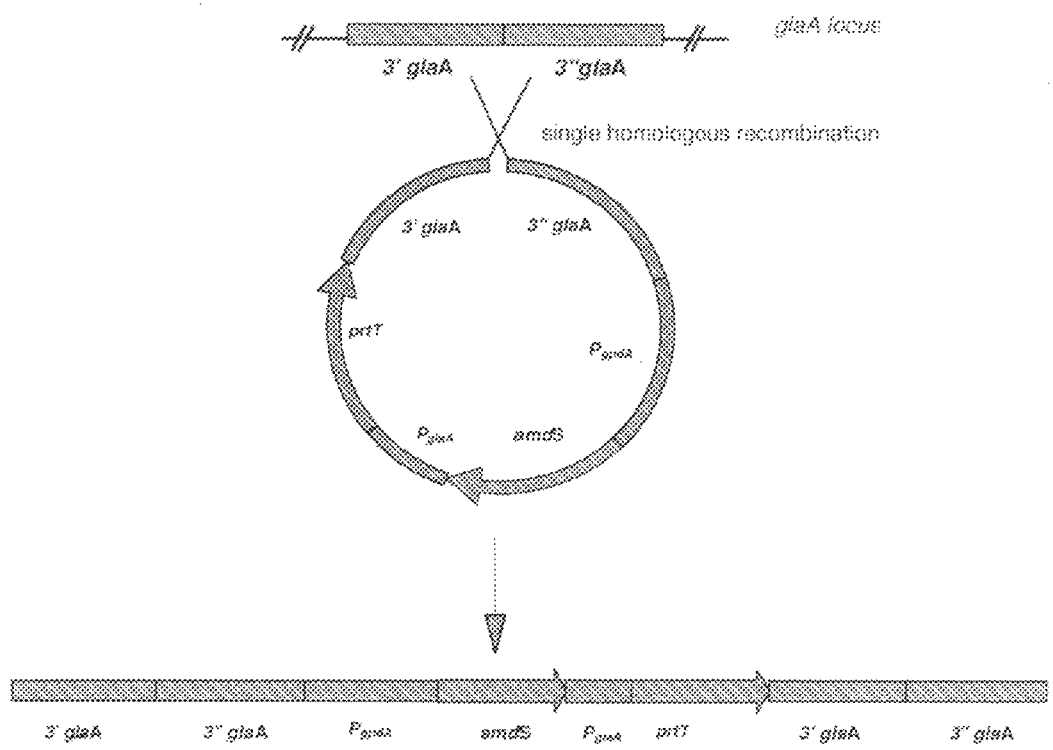
FIG. 6 Schematic presentation of integration through single homologous recombination. The expression vector comprises the selectable amdS marker, a glaA promoter connected to a prtT sequence of the protease transcriptional activator of the invention. These features are flanked by homologous regions of the glaA locus (3' glaA and 3" glaA, respectively) to direct integration at the genomic locus.

In order to introduce the pGBFINPRT-1 vector (FIG. 3) in *A. niger* WT 2, a transformation and subsequent selection of transformants was carried out as described in WO98/46772 and WO99/32617. In principle, linear DNA of vector pGBFINPRT-1 was isolated and used to transform *A. niger*. Transformants were selected on acetamide media and colony purified according standard procedures. Growing colonies were diagnosed for integration at the glaA locus and for the copy number. An example of this is shown in FIG. 6. Transformants of pGBFINPRT-1 with similar estimated copy number were selected and named PRTT.

Additionally, the selectable marker gene and the gene of the invention could have been on two constructs. The vector with the gene of the invention would have been co-transformed with an amdS selectable marker-gene containing vector, which is designated pGBAAS-1' (constructed as described in EP 635574B1). Both vectors comprise two DNA domains homologous to the g/aA locus of *A. niger* host strain to direct targeting to the truncated glaA locus in WT 2. In the case of co-transformation, spores of transformants are plated on fluoro-acetamide media to select strains, which lost the amdS marker.

Example 5

Enhanced Protease Expression in MT Transformants Compared to WT Strains

In the following example, the effect of the overexpression of a representative cDNA prtT clone (pGBFINPRT-1) comprising the sequence as identified in the SEQ ID NO 2 on the activity of the protease spectrum is determined.

Protease activities for a number of selected PRTT transformants (generated in example 4) are determined in the culture broth and compared to WT strains.

In a first step, the prtT overexpression was confirmed by Northern blot analysis of a number of PRTT transformants of *A. niger* WT 2 and the prtT mRNA levels were compared to *A. niger* WT 1 and WT 2. The RNA samples were obtained from the mycelium grown in 100 ml of the medium at 34° C. and 170 rpm in an incubator shaker using a 500 ml baffled shake flask as described above and in more detail in EP 635 574 B1. After 2 and 4 days of fermentation mycelium was collected and used for isolation of RNA (protocol see Example 1) and Northern blot analysis following the standard procedures of Northern blot analysis (Sambrook et al., 1989). For a number of PRTT transformants, increased prtT expression was seen after visualization of the Northern blot (data not shown).

Figure 7:
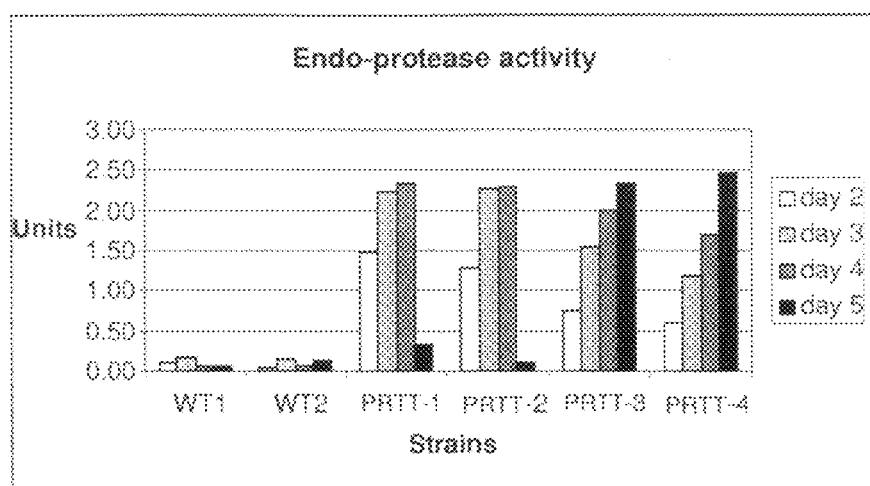
FIG. 7 Extra-cellular acidic protease activity of PRTT strains during several days of the fermentation. Protease activity measured using BSA as substrate. One Unit=$\Delta OD_{280}$/hour of 50 µl supernatant.

The PRTT transformants of WT 2 with increased prtT expression and both strains WT 1, and WT 2 were used to perform shake flask experiments as described above. After 2, 3, 4 and 5 days of fermentation, samples were taken to determine protease activities as described in Experimental Information. Results are shown in FIG. 7. The total acid extracellular protease activity in the selected PRTT transformants of WT 2 was increased compared to WT 1 and WT 2 in almost all time points examined. Additionally the samples obtained by the incubation of BSA with the culture supernatant were analyzed on SDS-PAGE gels (data not shown). These data clearly demonstrated an enhanced degradation of BSA in the samples of PRTT transformants leading amongst others to formation of low molecular weight peptides.

This data prove that the cDNA prtT clone of pGBFIN-PRT-1 encodes a functional protease transcriptional activator. Therefore, the nucleotide sequence provided in SEQ ID NO 2 is encoding a functional transcriptional activator protein PrtT.

Example 6

Inactivation of the prtT Gene in *Aspergillus niger*

Figure 8:
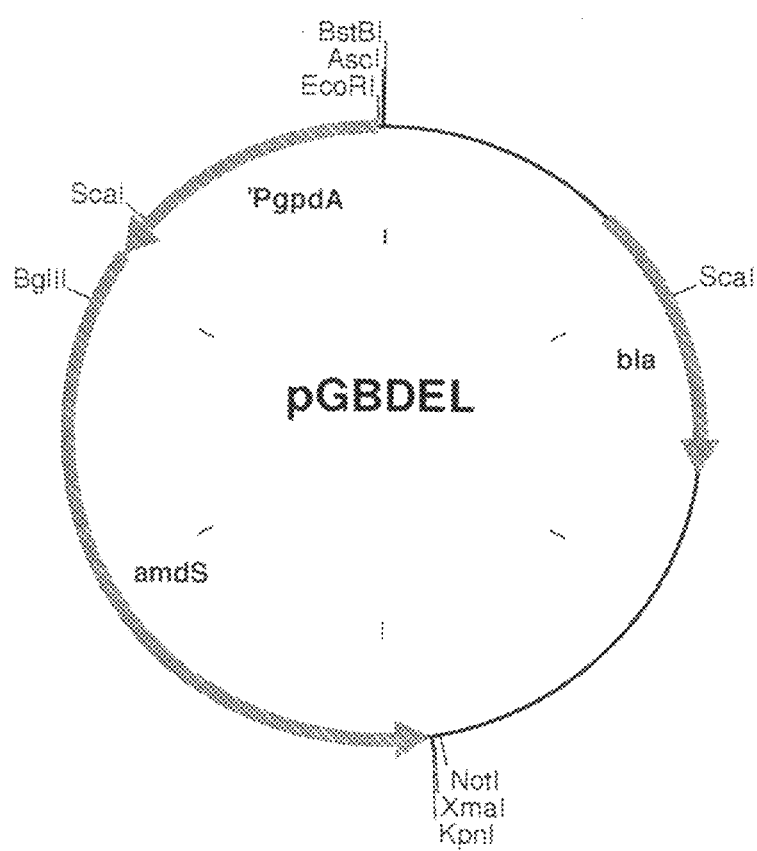
FIG. 8 Plasmid map of replacement vector pGBDEL. Indicated are the multiple cloning sites for cloning the flanking regions relative to the amdS marker.

A gene replacement vector for the prtT gene encoding the protease regulator of the invention was designed according to known principles and constructed according to routine cloning procedures (Sambrook et al. (1989)). In essence, these vectors comprise approximately 1000-3000 bp flanking regions of an prtT ORF for homologous recombination at the predestined genomic locus. In addition, it contains a bi-directional amdS selection marker, in-between direct repeats. The general design of these deletion vectors was previously described in EP635574 B and WO 98/46772. Genomic DNA of *A. niger* WT 1 was sequenced and analyzed as described above. Using the oligonucleotides identified as SEQ ID NO 11 and identified as SEQ ID NO 12 and genomic DNA of *A. niger* WT 2 as a template, PCR was used to amplify a 1.5 kb prtT downstream flanking region and introduce KpnI and XmaI restriction sites at the ends, to allow cloning in pGB-DEL (FIG. 8). This 1.5 kb prtT downstream flanking fragment was digested with KpnI and XmaI and introduced in a KpnI and XmaI digested vector pGBDEL, generating pGB-DEL-PRT1.

Using the oligonucleotides identified as SEQ ID NO 7 and identified as SEQ ID NO 8 and genomic DNA of *A. niger* WT 2 as a template, a 3 kb prtT upstream flanking region, identified as a fragment A, was amplified by PCR. Additionally, a BstBI restriction site was attached to the 5'-end and an overlapping sequence of the prtT downstream region at the 3'-end of the fragment A. Using oligonucleotides identified as SEQ ID NO 9 and as SEQ ID NO 10 and genomic DNA of *A. niger*

Figure 9:
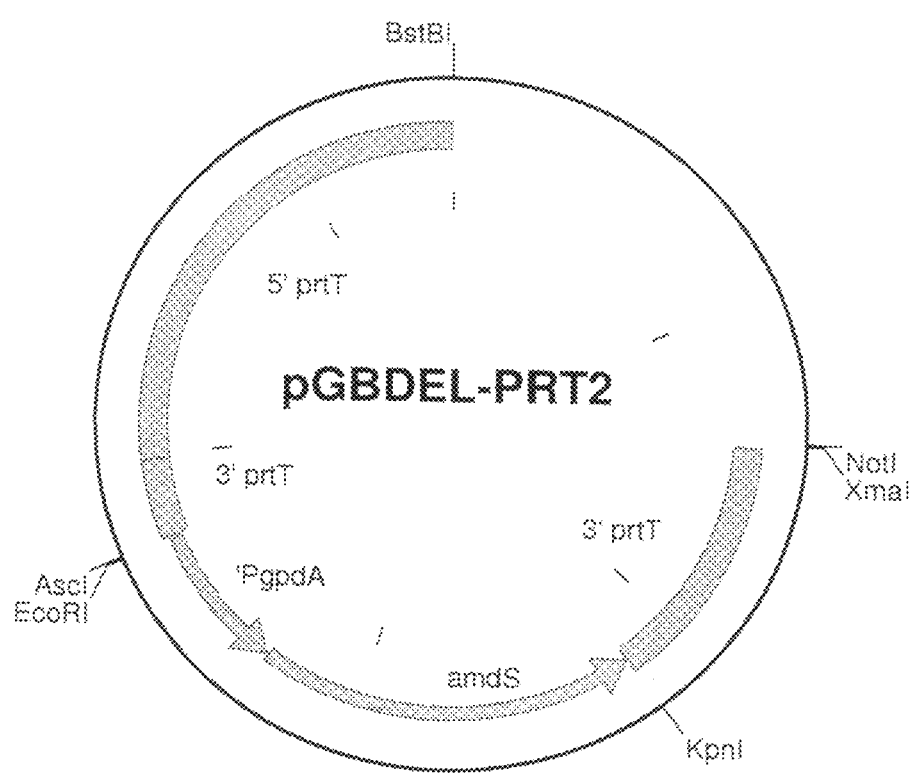
FIG. 9 Plasmid map of replacement vector pGBDEL-PRT2. Indicated are the 5' prtT flanking region, the 3' prtT flanking regions relative to the amdS marker. The sequence of the prtT 3' sequences overlap at least a few hundred bp. The *E. coli* DNA was removed by digestion with restriction enzyme BstBI and XmaI, prior to transformation of the *A. niger* strains.

WT 2 as a template, a 500 bp prtT downstream flanking region, identified as a fragment B, was amplified by PCR. Both resulting fragments, A and B, were fused by sequence overlap extension (SOE-PCR, as described in Gene. 1989 Apr. 15; 77(1):51-9. Ho S N, Hunt H D, Horton R M, Pullen J K, Pease L R "Site-directed mutagenesis by overlap extension using the polymerase chain reaction") using PCR, oligonucleotides identified as SEQ ID NO 7 and SEQ ID NO 10 and fragments A and B; generating a 3.5 kb fragment C. This fragment C was digested with BstBI and AscI and introduced in a BstBI and AscI digested vector pGBDEL-PRT1, generating pGBDEL-PRT2 (FIG. 9). The sequence of the introduced PCR fragments comprising the upstream and downstream regions of the prtT gene were confirmed by sequence analysis.

Figure 10:
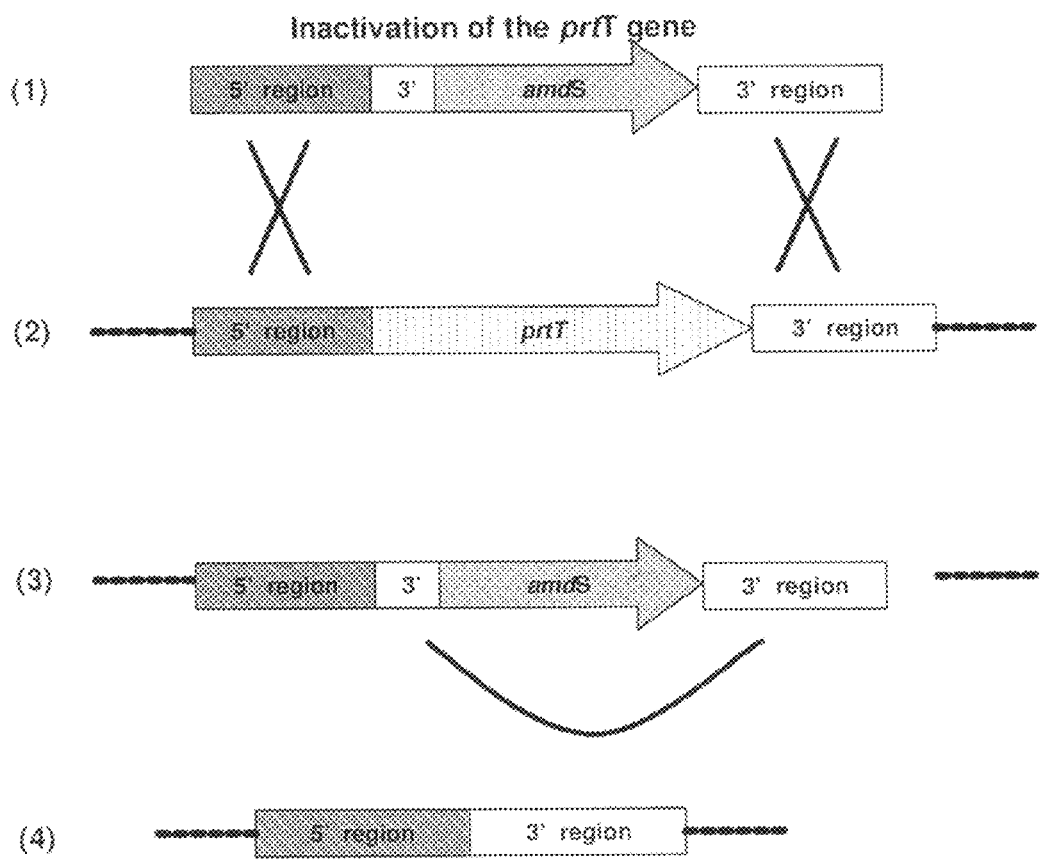
FIG. 10 Schematic presentation of the prtT deletion. A linear DNA construct of pGBDEL-PRT2, comprising the amdS selection marker flanked by homologous regions (5' and 3') of the prtT gene (1), integrates through double homologous recombination (X) at the genomic prtT locus (2) and replaces the genomic prtT gene copy (3). Subsequently, recombination over the direct repeats (U) removes the amdS marker, resulting in precise excision of the prtT gene (4).

Linear DNA of BstBI/XmaI-digested deletion vector pGBDEL-PRT2 was isolated and used to transform *A. niger* WT 2. This linear DNA can integrate into the genome at the prtT locus, thus substituting the prtT coding sequence with the construct containing amdS (see FIG. 10). Transformants were selected on acetamide media and colony purified according to standard procedures. Growing colonies were diagnosed by PCR for integration at the prtT locus. Deletion of the prtT gene was detectable by amplification of a band, with a size specific for the pGBDEL-PRT2 insert and loss of a band specific for the wild-type prtT locus. Spores were plated on fluoro-acetamide media to select strains, which lost the amdS marker. Candidate strains were tested using Southern analysis for proper deletion of the prtT gene. Strains dPRTT were selected as representative strains with the prtT gene inactivated (see FIG. 10).

Example 7

Comparison of the Protease Production in WT 2 and dPRTT *A. niger* Strains

Figure 11:
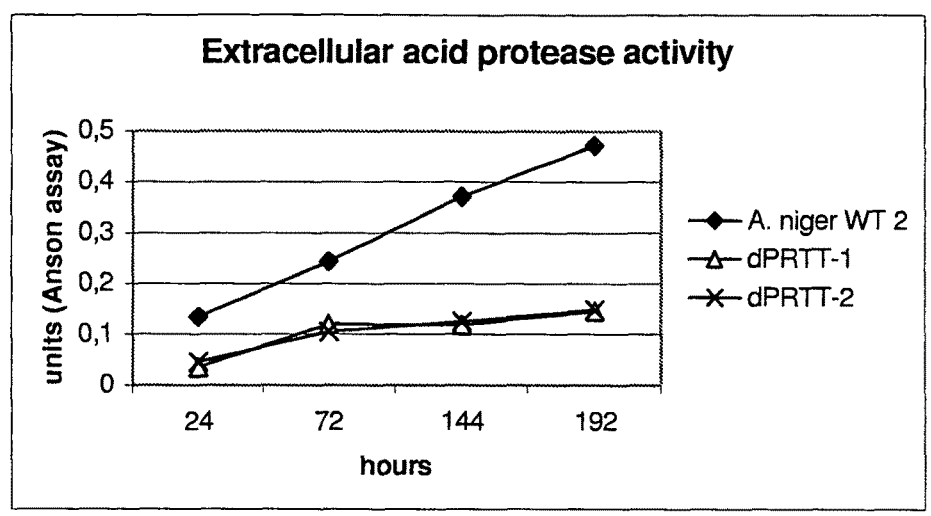
FIG. 11 Endoprotease activity in supernatant of the *A. niger* WT2 strain and dPRTT strains. Activity on the Y-axis is the endoprotease activity determined in U/50 µl per hour. The X-axis indicates culture time (hours) when the supernatant was collected.

The selected dPRTT strains (proper pGBDEL-PRT2 transformants of WT 2, isolated in example 6) and the strain *A. niger* WT 2 were used to perform shake flask experiments in 100 ml of the medium as described in EP 635 574 B1 at 34° C. and 170 rpm in an incubator shaker using a 500 ml baffled shake flask. After 1, 3, 6 and 8 days of fermentation, samples were taken to determine the endoprotease activity. In FIG. 11, endoprotease activity of WT 2 and dPRTT strains is shown. The endoprotease activity in the selected dPRTT transformants of WT 2 was clearly decreased compared to the one of *A. niger* WT 2 at all time points measured. We concluded that inactivation of the protease regulator PrtT was successful and resulted in the decrease of expression of extracellular proteases.

Example 8

Increased Production of a Protease Sensitive Protein in the dPRTT *A. niger* Strain Proteolytic degradation is a well-known problem when over-expressing a (heterologous) protein in *A. niger*. This example demonstrates how increased yields of a protein of interest can be obtained by manipulating the protease spectrum of *A. niger* through the disruption of prtT.

Figure 12:
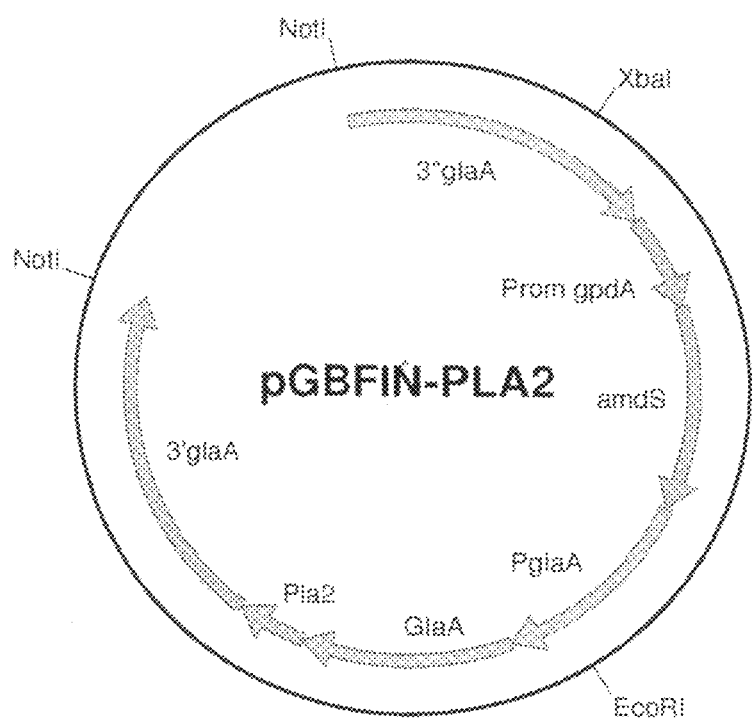
FIG. 12 Plasmid map of the PLA2 expression vector pGB-FIN-PLA2. Indicated are the glaA flanking regions relative to the glaA promoter, the truncated glaA gene and the pla2 coding sequence. The *E. coli* DNA was removed by digestion with restriction enzyme NotI, prior to transformation of the *A. niger* strains.
Figure 13:
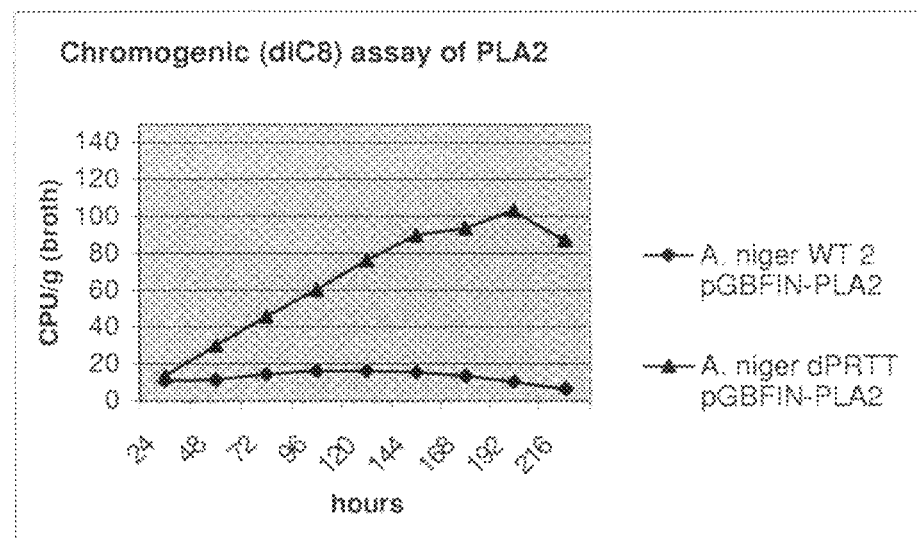
FIG. 13 Phospoholipase A2 activity measured in the broth of *A. niger* pGBFIN-PLA2 transformants of WT 2 and dPRTT strains. Phospholipase A2 activities were measured as indicated in Experimental information.

Porcine phospholipase A2 (PLA2) protein was selected as a model protein. It has been shown earlier that this protein is susceptible to protease degradation (Roberts I. N., Jeenes D. J., MacKenzie D. A., Wilkinson A. P., Sumner I. G. and Archer D. B. (1992). Heterologous gene expression in *Aspergillus niger* a glucoamylase-porcine pancreatic phospholipase $A_2$ fusion protein is secreted and processed to yield mature enzyme. Gene 122: 155-161 . . . ). The fragment for overexpression of PLA2 was made as a fusion of proPLA2 with a native glucoamylase A gene of *A. niger* and was prepared in principle as described by Roberts et al. (1992). This glaA-pla2 fusion gene was cloned into pGBFIN23 using the same technique as described in example 2.1, resulting in pGBFIN-PLA2 (FIG. 12). In order to introduce the pGBFIN-PLA2 vector in *A. niger* WT 2 and *A. niger* dPRTT strains (as constructed in Example 6), a transformation and subsequent selection of transformants was carried out as described in WO98/46772 and WO99/32617. In principle, linear DNA of vector pGBFIN-PLA2 was isolated and used to transform *A. niger*. Transformants were selected on acetamide media and colony purified according standard procedures. Growing colonies were diagnosed for integration at the glaA locus and for the copy number. An example of this is shown in FIG. 6. Several *A. niger* WT 2 and dPRTT transformants having one copy of the pGBFIN-PLA2 plasmid integrated in the glaA locus were selected to perform shake flask experiments in 100 ml of the Fermentation Medium 2 (FM2) as described in experimental procedures at 34° C. and 170 rpm in an incubator shaker using a 500 ml baffled shake flask. The culture broth was collected during 9 days of the cultivation and the PLA2 activity was measured as described above. FIG. 13, shows the PLA2 activity as measured in an *A. niger* dPRTT pGBFIN-PLA2 transformant and in an *A. niger* WT 2 pGBFIN-PLA2 transformant. It is clear that in the strain with the deleted prtT gene, a clear increase of the PLA2 activity is seen, whereas in the strain having the intact copy of prtT almost no PLA2 activity could be measured.

Example 9

Isolation of Nucleotide Sequences Encoding Proteins with Similarity to *A. niger* PrtT by Performing TBlastn Search in Nucleotide Sequence Databases In this example, we show how the *A. niger* PrtT protein sequence (SEQ ID NO 3) can be used to identify functional homologues in other organisms. We present data of two searches—(i) a search in a nucleotide sequence patent database, such as GENESEQ™ (*Aspergillus oryzae* case), and (ii) in nucleotide sequence databases accessible for instance via National Centrum for Biotechnology Information (NCBI) (*Aspergillus fumigatus* case).

ad (i) The PrtT sequence of SEQ ID NO 3 was used to perform a TBlastn (protein query vs. translated database) search against the nucleotide sequence patent databases. A protein sequence of 624 amino acids was identified, which has 71% match percentage, i.e. identity, with the *A. niger* PrtT sequence SEQ ID NO 3 (see FIG. 14). To the corresponding cDNA sequence, the SEQ ID NO 14 was assigned, which describes the nucleotide sequence encoding the *A. oryzae* PrtT protease transcriptional activator. The deduced protein sequence is described in SEQ ID NO 15 and the genomic sequence under the SEQ ID NO 13. Surprisingly, the protein under the SEQ ID NO 15, which was identified using the functional *A. niger* WT 1 PrtT protein differs from the *A. oryzae* protein described by the authors of WO 01/68864 in the C-terminal part and by one amino acid substitution in the N-terminal part of the protein (see FIG. 15). We have previously demonstrated the functionality of SEQ ID NO 3 (Example 5), therefore the *A. oryzae* PrtT protein sequence as described under the SEQ ID NO 15 should represent the functional homolog of *A. niger* PrtT in *A. oryzae*.

ad (ii) We have performed a similar search as described above against eukaryotic nucleotide sequence databases. A polypeptide sequence (621 amino acids) with a high match percentage, i.e. identity, to PrtT of *A. niger* has been identified in *A. fumigatus* (see FIG. 16). The PrtT sequence of *A. fumigatus* has 66% of match percentage, i.e. identity, with the *A. niger* PrtT SEQ ID NO 3. The *A. fumigatus* sequence of the *A. niger* PrtT homolog has SEQ ID NO 18, the cDNA encoding this polypeptide SEQ ID NO 17, and the prtT genomic sequence of *A. fumigatus* is under the SEQ ID NO 16.

Figures 17A, 17B:
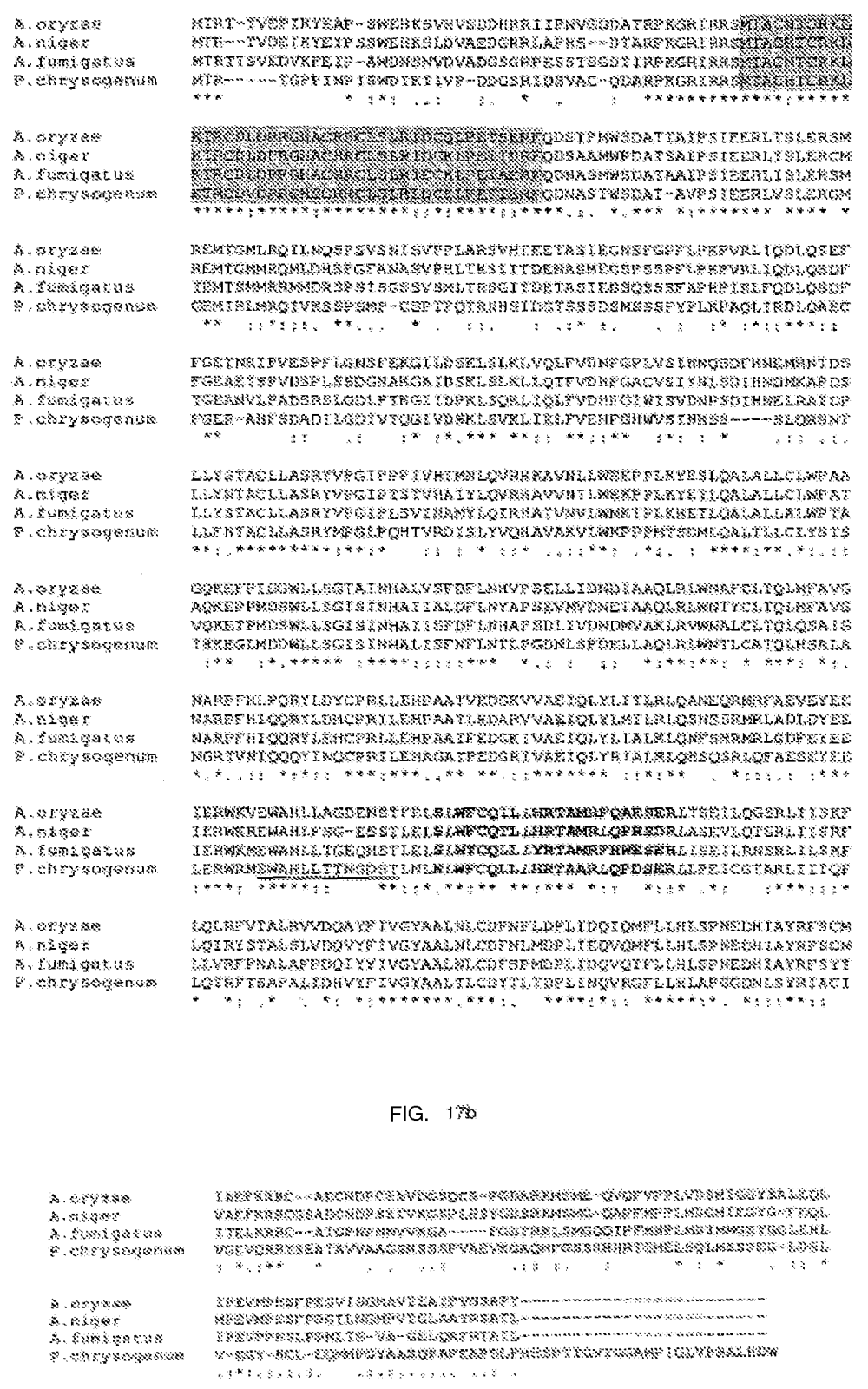

Four fungal PrtT polypeptide sequences of this invention were aligned using CLUSTAL W (reference see above in the text). Through out the alignment all the sequences show a high degree of amino acid identity (see the conserved boxes of amino acid sequences in FIG. 17). This example strengthens further the fact that the isolated PrtT polypeptides as described in SEQ ID NO: 15, SEQ ID NO: 18 and SEQ ID NO: 21 indeed encode functional homologues of the *A. niger* PrtT, the protease transcriptional regulator. To the zinc binuclear cluster Zn(II)2-Cys6 DNA binding domain of the PrtT polypeptides of *A. oryzae, A. fumigatus* and *P. chrysogenum* the SEQ ID NO: 25, SEQ ID NO: 26 and SEQ ID NO: 27 were assigned, respectively.

FIG. 18 depicts the differences found between several PrtT polypeptide sequences in their C-terminal part: an alignment was performed along 12 amino acids derived from the functional *A. niger* PrtT polypeptide of the invention and having the SEQ ID NO: 22. Alignment of the following PrtT was made: the *A. niger* and *A. oryzae* PrtT sequences of applications WO 00/20596 and WO 01/68864 and the PrtT polypeptides of the invention. It was found that the *A. oryzae* PrtT sequence of the application WO 01/68864 terminates preliminary. As underlined in FIG. 17, this preliminary termination of this PrtT polypeptide is close to the Leu-zipper domain and therefore it might affect its functionality. The *A. oryzae* PrtT sequence of the application WO 01/68864 completely misses the Leu zipper domain. Furthermore, the *A. niger* PrtT sequence of WO 00/20596 and WO 01/68864 applications comprise 17 additional amino acids in this region, caused by an unrecognised intron sequence as mentioned above in Example 3.1. This insertion can affect the topology of the protein domains (e.g. the subsequent Leu zipper domain as depicted in FIG. 4) and therefore the functionality of the PrtT protein.

The invention described and claimed herein is not to be limited in scope by the specific embodiments herein enclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In case of conflict, the present disclosure including definitions will control.

The invention claimed is:

1. A method of producing a polypeptide, comprising:
(a) cultivating a fungal host cell useful for the production of a polypeptide, in a nutrient medium suitable for production of the polypeptide and optionally;
(b) recovering the polypeptide from the nutrient medium of the mutant cell;
wherein the host cell is a mutant of a parent cell, in which the mutant:
produces more of a transcriptional activator than the parent cell when cultured under the same conditions wherein the transcriptional activator is encoded by an isolated nucleic acid sequence coding for an isolated polypeptide having transcriptional activity on a protease promoter, wherein said polypeptide is selected from the group consisting of:
(a) a polypeptide having transcriptional activity on a protease promoter comprising the amino acid sequence of SEQ ID NO: 3;
(b) a polypeptide having transcriptional activity on a protease promoter comprising a peptide fragment, said peptide fragment having at least 80% sequence identity with SEQ ID NO:22;
(c) a polypeptide having transcriptional activity on a protease promoter comprising peptide fragments, said peptide fragments having at least 80% sequence identity with both SEQ ID NO:22 and SEQ ID NO: 4; and
(d) a polypeptide having transcriptional activity on a protease promoter comprising (i) an amino acid sequence which has at least 90% sequence identity with the amino acid sequence of SEQ ID NO: 3 and comprising (ii) a peptide fragment, said peptide fragment comprising the amino acid sequence: EWAHL(X)$_{5-20}$ST, wherein "X" represents any amino acid and the range 5-20 represents the number of "X" found; and
comprises a DNA sequence encoding the polypeptide, the transcription of which is activated by the transcriptional activator.

2. The method of claim 1, wherein the polypeptide is native to the parent cell.

3. The method of claim 1, wherein the polypeptide is heterologous to the parent cell.

4. The method of claim 1, wherein the polypeptide having transcriptional activity on a protease promoter comprises (i) an amino acid sequence which has at least 95% sequence identity with the amino acid sequence of SEQ ID NO: 3 and (ii) a peptide fragment, said peptide fragment comprising the amino acid sequence: EWAHL(X)$_{5-20}$ST.

5. The method of claim 1, wherein the polypeptide having transcriptional activity on a protease promoter comprises the amino acid sequence of SEQ ID NO: 3 or is a polypeptide obtainable by expression of the prtT cDNA contained in pGBFINPRT-1, deposited under accession number CBS118680 or is a polypeptide obtainable by expression of the prtT cDNA contained in pGBPRT-1, deposited under accession number CBS118681.

6. The method according to claim 1 wherein the polypeptide having transcriptional activity on a protease promoter is obtained from a filamentous fungal strain.

7. The method according to claim 6 wherein the filamentous fungal strain is an *Aspergillus* strain.

8. The method according to claim 7 wherein the *Aspergillus* strain is a strain of *Aspergillus niger* or *Aspergillus oryzae* or *Aspergillus sojae* or *Aspergillus fumigatus*, or a respective synonym or teleomorph thereof.

9. The method according to claim 1 wherein the host cell produces more of the transcriptional activator than the parent cell when cultured under the same conditions by introducing into the parent cell one or more copies of:
(i) said nucleic acid sequence,
(ii) a nucleic acid construct comprising said nucleotide sequence operably linked to one or more control sequences, or
(iii) an expression vector comprising said nucleic acid construct, a promoter, and a transcriptional and translational stop signals.

10. The method according to claim 1 wherein the nucleic acid sequence encoding the transcriptional activator is operably linked to a promoter, which is stronger than the corresponding promoter of the parent cell.

11. The method according to claim 1 wherein the polypeptide is extracellular protease.

12. The method according to claim 11 wherein the extracellular protease is *Aspergillus oryzae* alkaline protease, *A. oryzae* neutral metalloprotease, or *A. niger* aspergillopepsin protease.

13. The method according to claim 1 wherein the host cell further comprises a promoter sequence, wherein the promoter sequence can be activated by the transcriptional activator and is operably linked to the nucleic acid sequence encoding the polypeptide.

14. The method according to claim 13 wherein the promoter sequence or a functional part thereof, is from a protease gene.

15. The method according to claim 14 wherein the protease gene is *Fusarium oxysporum* trypsin-like protease gene, *Aspergillus oryzae* alkaline protease gene, *Aspergillus niger* pacA gene, *A. oryzae* neutral metalloprotease gene, *A. niger* aspergillopepsin protease gene, or *F. venenatum* trypsin gene.

\* \* \* \* \*

```
                        SEQUENCE LISTING

<160> NUMBER OF SEQ ID NOS: 27

<210> SEQ ID NO 1
<211> LENGTH: 6837
<212> TYPE: DNA
<213> ORGANISM: Aspergillus niger
<220> FEATURE:
<221> NAME/KEY: exon
<222> LOCATION: (2998)..(3224)
<220> FEATURE:
<221> NAME/KEY: Intron
<222> LOCATION: (3225)..(3336)
<220> FEATURE:
<221> NAME/KEY: exon
<222> LOCATION: (3337)..(3738)
<220> FEATURE:
<221> NAME/KEY: Intron
<222> LOCATION: (3739)..(3796)
<220> FEATURE:
<221> NAME/KEY: exon
<222> LOCATION: (3797)..(4222)
<220> FEATURE:
<221> NAME/KEY: Intron
<222> LOCATION: (4223)..(4272)
<220> FEATURE:
<221> NAME/KEY: exon
<222> LOCATION: (4273)..(4502)
<220> FEATURE:
<221> NAME/KEY: Intron
<222> LOCATION: (4503)..(4553)
<220> FEATURE:
<221> NAME/KEY: exon
<222> LOCATION: (4554)..(5140)

<400> SEQUENCE: 1
tggctaggtg tcgattttga gtacctaatt gctaggcatg ttatggagca cttggaaggg      60 gccagggga accgtagcat tgacatataa agtggacacc atctgctgtt gttggtggaa     120
gtgaagcttc aattaagaaa gagcagaaac gactttggtt gaaggaaaat acagaagaaa     180
```

```
gttgatcgac tgcaaaacga cgccatcaga ttccggcaac gaacaaaaca gacaaaacag    240
acaaactgcg cataaggcgt gaccggcgat catgtgtcta caaagaactt gctggatcgt    300
cgcggcctca ttattctcca gctccctccc ctcctttact tcctcggtat actcatgaac    360
acatgcctac gattgtcaat tcccagcctg tcgctatcat gttctcgcag ggatcatggt    420
ctggccgttg aactccsctg attatcctgc ctgagagcct acgtcttccg atgacgacgt    480
gtccggtggc cgaaccgcca tccgatatta acctgcagcc gggaatagcc atggacagac    540
aaacctagga ggctagctaa aagttagtgt atgaggtgag caaggatata ctcggcgttc    600
cctcttgggc tttccgaaat ccataaggga gtccgccaaa cagttcatta tgatcttatt    660
aagccgagtt aatttagctg caggtacggc ttcgataagg atgggatacg gactcctacg    720
acctggcatt tcggagatat ccgaccatca cacgtcttcc aacaaagagt aatatgagca    780
atgaagtggc ccgcagtacg gagaagttgc ctctatcgtt ggcttctcgt gtcgagcgcg    840
ctcatggcta ataacgttaa aacattgaca catcaattca tgataactaa caagtgagac    900
atttgccact cattcccgaa tgcaaccact ctatcaggcc agtggggaac gcacggctag    960
cctcgtcgac ctccgatggt tggtttctct gatctgagtt tcctactggg ccatctcagg   1020
aaggtggaaa aagcaatggc accatttacc gatacaaagc gcagtgttgg ctgccaattt   1080 ttactttttcc accctcacc cgctcttctt gcctactggc gcctggaagt gaaatcctgg   1140
agcaggagaa aggaacggta attggcaagc gctaaccaac ttgcgccttg tactttggag   1200
ccggcgctgc gagccgacgc gccccattcc caaaatggcc taacggccgt gaagccgagg   1260
ttcagggtgt ccctacttgc aatgcttaac aatggacgga ataatattca acagccccag   1320
cgtcgcgctg gtcaaaaatc tagaagcagc aaatttgggc ctgaagccta gatggcgatg   1380
ccaatcaatc ctttctgtga aatgatttag ttactaatga gggggtgctg attcgctgtg   1440
gtatatgtga tgtctgtgtc gaaggcccca ggcagctcgt ccactccccc cgagaacaag   1500
ccttgctcag acaatccagg ctccaccgcg tgctgggtcc accactgctg ctgaccttaa   1560
cgcgggtgcc tgtcgattat gggtcgacca gccaatattg gaccgatatg cctcctccgt   1620
cccggattgt gaacatatga taaggaatga tgtgataagg aggaaaaaga cggtatgatc   1680
taaaagcatt gtacggacat aacaacaggg atgaagtggg ccagtaggag ctccgccatg   1740
atcctggtgg ctcgaatcag tcctgaggat cccccacggg ctgctgttgt ggaagacacc   1800
tgggcacact ggcaccacaa acgctggacc tgcatagaat atgctttgct ggcttcgggt   1860
ctagacatgg attgggataa tatcaatgtg catccttgct ataatccaac aatatttccg   1920
ttgatagccg acagggcagg cattcaatgt cgcattgcag catgcgccgt caagtgtaga   1980
gactagagag tgagacaaga gagaaaattt ttctctcctt ggtgctggaa agcccatttg   2040
agggatctta taaggtaatt gcctatgttc agtcgcctat ggtcttgtcg agagaaactc   2100
tttctcgtta agatctacat gatcgctttt gattttctct gggttcacgc ggttactttc   2160
tccccgtcaa tccccaaccg ctgttgtgcc tgaccatcaa tgtggaacgg ataaggggac   2220
aagagaaatt gaaggagcga tcataaaaag ctaattttgg tttattattt tttttttttc   2280
ttataaaact caaaaagaa acgaaaacg aaaaggaaa aagaaaagg taaaatggaa   2340 aaagaaaggc ggtcatcact tccaataacc atcagccaaa gatacagacg agttactgac   2400
cttcttatcc tggacttccg cccgatccat atcttcatga taagcaggga accgaacaaa   2460
tcaacgccaa cttcagcggc agttcctcac taatttccca cttcccaccg gcgtcatttt   2520
ggtcccaacc cctccctgg aagcagcggg atttagttac gatccggttt acatcggaga   2580
```

```
ctcggaaaat accatagcgc atgccaatca aaacccctcc cagggtgact ggccagtatc     2640
acgacccatt gtttctatct ttctagaaga cctgcaggga catggattgg ctggccgccg     2700
tgctgccgtc cattagcgtc tacccccaggt caagaacgga ctggacggac ccataaccaa    2760
tctaaccaaa gccaatttcg tcaattccca gctggcgagc acaatcccat tcccagggtt    2820
ggccgccaac tgttaaaagg cactatgtgt ctctccacct gcccgccccc ctcgatggcc    2880
tgcgcgtaat aactattcta ctgcttttg cctcttactt gcctcattat tagtatttta    2940
ctctactctc cagattgcct gccagcaatt ggtccaaagt ggactttgtt tgatgac       2997
```

| | | | | | | | | | | | | | | | | |
|---|---|---|---|---|---|---|---|---|---|---|---|---|---|---|---|---|
| atg | act | cga | acc | gtg | gac | gag | atc | aaa | tac | gaa | acg | cct | tct | tca | tgg | 3045 |
| Met | Thr | Arg | Thr | Val | Asp | Glu | Ile | Lys | Tyr | Glu | Thr | Pro | Ser | Ser | Trp | |
| 1 | | | | 5 | | | | | 10 | | | | | 15 | | |

```
gag cac aag agc ttg gac gtt gcc gag gat ggc agg cga cta gct ccc      3093
Glu His Lys Ser Leu Asp Val Ala Glu Asp Gly Arg Arg Leu Ala Pro
         20                  25                  30 cat tcc gac act gct cgt ccg aaa ggc cgc ata cga cga tcg atg act      3141
His Ser Asp Thr Ala Arg Pro Lys Gly Arg Ile Arg Arg Ser Met Thr
         35                  40                  45 gcc tgt cac aca tgt cgg aag ctt aaa act aga tgt gat cta gat ccg      3189
Ala Cys His Thr Cys Arg Lys Leu Lys Thr Arg Cys Asp Leu Asp Pro
     50                  55                  60 cgc ggt cat gcg tgc cgt cgc tgt cta tct cta ag  gtcagaggca           3234
Arg Gly His Ala Cys Arg Arg Cys Leu Ser Leu Arg
65                  70                  75 ctacctacct gccagttgaa gctttgtcct tctgaacgcg acatgatact agtcgtggaa    3294
tataactgtc ccaactttgc tgacagtcca caatatcttt ag a atc gat tgt aag     3349
                                               Ile Asp Cys Lys
                                                            80 ctg cct gaa acg acc gac cgc ttc caa gac agt gct gcg atg tgg cca      3397
Leu Pro Glu Thr Thr Asp Arg Phe Gln Asp Ser Ala Ala Met Trp Pro
         85                  90                  95 gac gcc acc tcg gca att ccc tcc atc gag gag cgc ctc acc tcc cta      3445
Asp Ala Thr Ser Ala Ile Pro Ser Ile Glu Glu Arg Leu Thr Ser Leu
        100                 105                 110 gaa aga tgc atg agg gag atg acg ggc atg atg cga cag atg cta gat     3493
Glu Arg Cys Met Arg Glu Met Thr Gly Met Met Arg Gln Met Leu Asp
        115                 120                 125 cac tcc cca ggt ttc gca aat gcc tcg gtt ccg cat ttg acc aaa agc     3541
His Ser Pro Gly Phe Ala Asn Ala Ser Val Pro His Leu Thr Lys Ser
    130                 135                 140 atc atc acg gat gaa aac gcc tcg atg gag gga agc ccg tcg tcc ccc     3589
Ile Ile Thr Asp Glu Asn Ala Ser Met Glu Gly Ser Pro Ser Ser Pro
145                 150                 155                 160 ttc ctg cct aag ccc gtt cgc ctc att cag gac ctc cag tcc gac ttc     3637
Phe Leu Pro Lys Pro Val Arg Leu Ile Gln Asp Leu Gln Ser Asp Phe
            165                 170                 175 ttc gga gaa gca gag act tcc ccc gtt gac tcc cct ctc tcc agc gat     3685
Phe Gly Glu Ala Glu Thr Ser Pro Val Asp Ser Pro Leu Ser Ser Asp
        180                 185                 190 ggt aac gcc aag ggc gct atc gac tct aag cta tcc ctc aaa ttg ttg     3733
Gly Asn Ala Lys Gly Ala Ile Asp Ser Lys Leu Ser Leu Lys Leu Leu
        195                 200                 205 caa ac  gtatgggtat acctgattga caattaccaa aaagctgcta atccttggcg      3788
Gln Thr caaatcag g ttt gtc gat cac ttt ggc gct tgc gtt tcc att tac aat      3836
           Phe Val Asp His Phe Gly Ala Cys Val Ser Ile Tyr Asn
                                 215                 220
```

| | | |
|---|---|---|
| ctc tcc gac atc cac aac gac atg aaa gcc ccc gac tct tta ctg tat<br>Leu Ser Asp Ile His Asn Asp Met Lys Ala Pro Asp Ser Leu Leu Tyr<br>225 230 235 | | 3884 |
| aat act gca tgc ctt cta gct tca cgc tat gta ccg ggg ata ccg aca<br>Asn Thr Ala Cys Leu Leu Ala Ser Arg Tyr Val Pro Gly Ile Pro Thr<br>240 245 250 255 | | 3932 |
| tct acc gtg cat gct ata tac ctt caa gtg cga cat gca gtc gtc aat<br>Ser Thr Val His Ala Ile Tyr Leu Gln Val Arg His Ala Val Val Asn<br>260 265 270 | | 3980 |
| att ttg tgg gaa aaa cca ccc ctg aag tat gag acc ctc caa gca ctt<br>Ile Leu Trp Glu Lys Pro Pro Leu Lys Tyr Glu Thr Leu Gln Ala Leu<br>275 280 285 | | 4028 |
| gca ctt ctc tgt ctc tgg cca gca acc gcc cag aaa gag cca ccc atg<br>Ala Leu Leu Cys Leu Trp Pro Ala Thr Ala Gln Lys Glu Pro Pro Met<br>290 295 300 | | 4076 |
| gac agc tgg ctg ctg agt ggt atc tca att aac cat gca att atc gcg<br>Asp Ser Trp Leu Leu Ser Gly Ile Ser Ile Asn His Ala Ile Ile Ala<br>305 310 315 | | 4124 |
| ctc gat ttc cta aac tat gcg ccc tcg gaa gtc atg gtg gac aat gaa<br>Leu Asp Phe Leu Asn Tyr Ala Pro Ser Glu Val Met Val Asp Asn Glu<br>320 325 330 335 | | 4172 |
| acg gct gcg cag ctg cgg cta tgg aat aca tat tgc ttg aca cag cta<br>Thr Ala Ala Gln Leu Arg Leu Trp Asn Thr Tyr Cys Leu Thr Gln Leu<br>340 345 350 | | 4220 |
| ca gtgggtttca tctaagatct cccgtccaga agatagctaa caagctttag t ttt<br>His Phe | | 4276 |
| gcg gtc ggg aat gcg cgt cct ttc cat atc cag caa aga tac ctt gac<br>Ala Val Gly Asn Ala Arg Pro Phe His Ile Gln Gln Arg Tyr Leu Asp<br>355 360 365 | | 4324 |
| cac tgc cca cgg ata ctg gag cac cca gca gca act ctg gag gac gca<br>His Cys Pro Arg Ile Leu Glu His Pro Ala Ala Thr Leu Glu Asp Ala<br>370 375 380 385 | | 4372 |
| agg gtt gta gca gaa ata cag ttg tat ttg atg aca ttg cgg ctc cag<br>Arg Val Val Ala Glu Ile Gln Leu Tyr Leu Met Thr Leu Arg Leu Gln<br>390 395 400 | | 4420 |
| agc aat agc agt cga atg cgg ttg gcg gac ctt gac tat gag gaa ata<br>Ser Asn Ser Ser Arg Met Arg Leu Ala Asp Leu Asp Tyr Glu Glu Ile<br>405 410 415 | | 4468 |
| gag cga tgg aag agg gag tgg gct cac ctt ttc t gtaagaagcc<br>Glu Arg Trp Lys Arg Glu Trp Ala His Leu Phe<br>420 425 | | 4512 |
| tgttcttgtt tccggggac taccactgac gagagcaaca g ct ggg gaa agt tcc<br>Ser Gly Glu Ser Ser<br>430 | | 4567 |
| aca ttg gag ctg agc ctt tgg ttc tgc cag aca ctc ctt cac cgc aca<br>Thr Leu Glu Leu Ser Leu Trp Phe Cys Gln Thr Leu Leu His Arg Thr<br>435 440 445 | | 4615 |
| gca atg agg ctt cag ccc aga tcc gac agg ctc gca tct gag gtt ctg<br>Ala Met Arg Leu Gln Pro Arg Ser Asp Arg Leu Ala Ser Glu Val Leu<br>450 455 460 465 | | 4663 |
| caa acc tca cgt ctg ata ata tcg cgg ttc ctc cag atc cgg tac tct<br>Gln Thr Ser Arg Leu Ile Ile Ser Arg Phe Leu Gln Ile Arg Tyr Ser<br>470 475 480 | | 4711 |
| acc gca tta agc ctt gtc gac caa gtc tat ttc att gtc ggc tac gct<br>Thr Ala Leu Ser Leu Val Asp Gln Val Tyr Phe Ile Val Gly Tyr Ala<br>485 490 495 | | 4759 |
| gca ctg aat ctg tgc gat ttc aat ctt atg gac ccg ctt atc gag caa<br>Ala Leu Asn Leu Cys Asp Phe Asn Leu Met Asp Pro Leu Ile Glu Gln<br>500 505 510 | | 4807 |
| gtg cag atg ttc ctg ctg cat ctc tcc ccg aac gaa gac cac atc gcc | | 4855 |

-continued

| | | | | | | | | | | | | | | |
|---|---|---|---|---|---|---|---|---|---|---|---|---|---|---|
| Val | Gln | Met | Phe | Leu | Leu | His | Leu | Ser | Pro | Asn | Glu | Asp | His | Ile | Ala |
| | 515 | | | | 520 | | | | | 525 | | | | |

```
tac cgg ttt tcg tgc atg gtc gcc gag ttc aag cgg cga tgt ggc agt      4903
Tyr Arg Phe Ser Cys Met Val Ala Glu Phe Lys Arg Arg Cys Gly Ser
530             535             540             545 gcg gaa tgc aat gac cca tca tcc act gtc aag ggg tct ccg tta tca      4951
Ala Glu Cys Asn Asp Pro Ser Ser Thr Val Lys Gly Ser Pro Leu Ser
            550             555             560 tcc tac ggc gac agt cgt aag atg agc atg ggg caa gca ccg ttc atg      4999
Ser Tyr Gly Asp Ser Arg Lys Met Ser Met Gly Gln Ala Pro Phe Met
        565             570             575 cca ccg ctc atg gat ggc atg atc gag ggg tac ggc ttc gag caa ctg      5047
Pro Pro Leu Met Asp Gly Met Ile Glu Gly Tyr Gly Phe Glu Gln Leu
            580             585             590 atg cca gaa gtc atg ccg agt tcc ttt ccg gat ggg ata ctc aac gga      5095
Met Pro Glu Val Met Pro Ser Ser Phe Pro Asp Gly Ile Leu Asn Gly
    595             600             605 atg cct gtg act ggg cta gca gcg tat cgg tca gcg acg ctg taa          5140
Met Pro Val Thr Gly Leu Ala Ala Tyr Arg Ser Ala Thr Leu
610             615             620 gtaatcgaga tcgggttgga aaggacatga gtggggtgg tggtggtagt agcagtaaca      5200
ccagggatga taacctgcag cggtggttta gttcctgccc atgggctgaa ctaaaacccc     5260
gaacctagca tgatgacgtg caacgaaagg atcataacca aggccaagta aatactaaaa     5320
taaaataata taattccaca cgatccacta ccaccaccac caccggatcc atcaggttgc     5380
cttcctgcac aggcctattt agttagaggg cccgtgccac gaaacatcac gtaattgagc     5440
gcttttgctt ccttgcaact taaacaaccc catagacact ctcacattca catgccaaac     5500
tactaactcc tactgaccac cagctgcagg aagccagcca gccaccattt cctaatcgga     5560
tatatctccg aaacgtacgc tttcctcctt tgttcggacc gttccgtgcc tccgcggaga     5620
gttgaacgag tcagaacaca ttcttttcgt ttctatcgtt tcttttccaa ggcagcagag     5680
agacgaacaa gtcagtgctt gctaactaac ttacccctca gcattttagt aaactactat     5740
ttaggaaaga gtaatcattc atcgaagaca agatgtttat ttctccgatc gaccaaacaa     5800
aaacgttcag gtagactaag tagtagtagt agtatgtctt tgacccttt actccactat      5860 ccgttgactg cacatagtag taagtaacta tctaaccagt tgccgaggag aggaaagtga     5920
gtgggtggga gccggaggat gccgccgaga attattaagt cgatcattgc tagttagtta     5980
tcttttcatg atgaggagag gaaggagagg ggggacggga ttagagaaat aaacttttct     6040
ctccaattaa ttatctggat taattaaaac ttggagagga gggtagggga gttgggtatt     6100
gttatgttgc tgtgaatgta ggtgtaactt ttggaaggaa attgacggga tgatgctact     6160
atgctgcagg cagtaggagg tgttgttcat ctcgcttgcc ccgcccgtag atggttgggt     6220
tcggatgtag atacttgatg gagataagta ggggttttttg tttctttttct ttccttttct    6280 ttttttatga tgaagtatat ttctctagta tgtttgtatg atgcagaggt tgaggttgaa     6340
tttactattg gtctgctgtt gttggtattg gctgggtgtc aatagaaata agtttactcc    6400
gtcgtttcgt gaggttgtag tgactgtggc tttgagacac taaggactag gtacaactac    6460
tacgtcggtg gtagtgattt tatccatact tactttgcag gcaaatgaat actgtggata    6520
ctaataatat aaaatgatct tgaagaatcc attacacata gaatcatcac gtcacctaat    6580
aatatatact gtcatctgag acatcctaat cacgtcatta tagcaataag cacctgagcg    6640
aaaattctac aaattgaagt cagcatctgg atcacgatca caggggtcat cgtcagtgg     6700 ccatgatatg atctgataca cttacacagt gtagctaaag aacaacacgc ctcctcctgc    6760
```

```
atccttgaaa acagtgatcg cagagcctgt gcgaatgtat cagttgatca atccataaag   6820
aatcaatgcg atggacg                                                  6837

<210> SEQ ID NO 2
<211> LENGTH: 1872
<212> TYPE: DNA
<213> ORGANISM: Aspergillus niger
<220> FEATURE:
<221> NAME/KEY: exon
<222> LOCATION: (1)..(227)
<220> FEATURE:
<221> NAME/KEY: exon
<222> LOCATION: (228)..(629)
<220> FEATURE:
<221> NAME/KEY: exon
<222> LOCATION: (630)..(1055)
<220> FEATURE:
<221> NAME/KEY: exon
<222> LOCATION: (1056)..(1285)
<220> FEATURE:
<221> NAME/KEY: exon
<222> LOCATION: (1286)..(1872)

<400> SEQUENCE: 2 atg act cga acc gtg gac gag atc aaa tac gaa acg cct tct tca tgg    48
Met Thr Arg Thr Val Asp Glu Ile Lys Tyr Glu Thr Pro Ser Ser Trp
1               5                   10                  15 gag cac aag agc ttg gac gtt gcc gag gat ggc agg cga cta gct ccc    96
Glu His Lys Ser Leu Asp Val Ala Glu Asp Gly Arg Arg Leu Ala Pro
            20                  25                  30 cat tcc gac act gct cgt ccg aaa ggc gcc ata cga cga tcg atg act   144
His Ser Asp Thr Ala Arg Pro Lys Gly Arg Ile Arg Arg Ser Met Thr
        35                  40                  45 gcc tgt cac aca tgt cgg aag ctt aaa act aga tgt gat cta gat ccg   192
Ala Cys His Thr Cys Arg Lys Leu Lys Thr Arg Cys Asp Leu Asp Pro
    50                  55                  60 cgc ggt cat gcg tgc cgt cgc tgt cta tct cta ag  a atc gat tgt aag 240
Arg Gly His Ala Cys Arg Arg Cys Leu Ser Leu Arg    Ile Asp Cys Lys
65                  70                  75                  80 ctg cct gaa acg acc gac cgc ttc caa gac agt gct gcg atg tgg cca   288
Leu Pro Glu Thr Thr Asp Arg Phe Gln Asp Ser Ala Ala Met Trp Pro
                85                  90                  95 gac gcc acc tcg gca att ccc tcc atc gag gag cgc ctc acc tcc cta   336
Asp Ala Thr Ser Ala Ile Pro Ser Ile Glu Glu Arg Leu Thr Ser Leu
            100                 105                 110 gaa aga tgc atg agg gag atg acg ggc atg atg cga cag atg cta gat   384
Glu Arg Cys Met Arg Glu Met Thr Gly Met Met Arg Gln Met Leu Asp
        115                 120                 125 cac tcc cca ggt ttc gca aat gcc tcg gtt ccg cat ttg acc aaa agc   432
His Ser Pro Gly Phe Ala Asn Ala Ser Val Pro His Leu Thr Lys Ser
    130                 135                 140 atc atc acg gat gaa aac gcc tcg atg gag gga agc ccg tcg tcc ccc   480
Ile Ile Thr Asp Glu Asn Ala Ser Met Glu Gly Ser Pro Ser Ser Pro
145                 150                 155                 160 ttc ctg cct aag ccc gtt cgc ctc att cag gac ctc cag tcc gac ttc   528
Phe Leu Pro Lys Pro Val Arg Leu Ile Gln Asp Leu Gln Ser Asp Phe
                165                 170                 175 ttc gga gaa gca gag act tcc ccc gtt gac tcc cct ctc tcc agc gat   576
Phe Gly Glu Ala Glu Thr Ser Pro Val Asp Ser Pro Leu Ser Ser Asp
            180                 185                 190 ggt aac gcc aag ggc gct atc gac tct aag cta tcc ctc aaa ttg ttg   624
Gly Asn Ala Lys Gly Ala Ile Asp Ser Lys Leu Ser Leu Lys Leu Leu
        195                 200                 205
```

```
caa ac  g  tttgtcgatcactttggcgcttgcgtttccatttacaatctc      672
Gln Thr    PheValAspHisPheGlyAlaCysValSerIleTyrAsnLeu
                       215                 220 tccgacatccacaacgacatgaaagccccggactctttactgtataat         720
SerAspIleHisAsnAspMetLysAlaProAspSerLeuLeuTyrAsn
225                  230                 235                 240 actgcatgcctrctagcttcacgctatgtaccggggataccgacatct         768
ThrAlaCysLeuLeuAlaSerArgTyrValProGlyIleProThrSer
                 245                 250                 255 accgtgcatgctatatacctrtcaagtgcgacatgcagtagtcaatatt        816
ThrValHisAlaIleTyrLeuGlnValArgHisAlaValValAsnIle
                 260                 265                 270 ttgtggaaaaaaccccctrtgaagtatgagaccctrtcaagcacttgca        864
LeuTrpGluLysProProLeuLysTyrGluThrLeuGlnAlaLeuAla
            275                 280                 285 ctrtctctgtrtctctggccagcaaccgcccagaaagagccaccccatggac     912
LeuLeuCysLeuTrpProAlaThrAlaGlnLysGluProProMetAsp
             290                 295                 300 agctggctgctgagtrggtatcrtcaattaaccatgcaattatcgcgctc       960
SerTrpLeuLeuSerGlyIleSerIleAsnHisAlaIleIleAlaLeu
305                 310                 315                 320 gatttcrctaaactatgcgccctcgagaaagtcatggtgagacaatgaaaacg   1008
AspPheLeuAsnTyrAlaProSerGluValMetValAspAsnGluThr
                     325                 330                 335 gctgcgcagctgcggctatggaatacattatgcrttgacacagcta ca  t     1056
AlaAlaGlnLeuArgLeuTrpAsnThrTyrCysLeuThrGlnLeuHis
                     340                 345                 350 tttgcgtcgcgggaatgcgcgtcctcttcatatccagcaaagagatacctt      1104
PheAlaValGlyAsnAlaArgProPheHisIleGlnGlnArgTyrLeu
             355                 360                 365 gaccactgcccacggatactgagcacccagcagcaactgaggagaagac        1152
AspHisCysProArgIleLeuGluHisProAlaAlaThrLeuGluAsp
         370                 375                 380 gcaaggttrgtagcagaaatacagttgtatttgatgacattgcggctc         1200
AlaArgValValAlaGluIleGlnLeuTyrLeuMetThrLeuArgLeu
385                 390                 395                 400 cagagcaatagcagtcgatgcggttgggcggacctrtgactattgagaga      1248
GlnSerAsnSerSerArgMetArgLeuAlaAspLeuAspTyrGluGlu
                 405                 410                 415 ataagagcgatggaagaggagtrgggctrcaccttttct ct  gggaaaagt    1296
IleGluArgTrpLysArgGluTrpAlaHisLeuPhe   SerGlyGluSer
                 420                 425              430 tccacattgaagctgagcctrtggttctrtgcagacactrctrtccaccgc     1344
SerThrLeuGluLeuSerLeuTrpPheCysGlnThrLeuLeuHisArg
             435                 440                 445 acagcaatgaggcttrcagccccagatccgacaggctrcgatrctgagtrt     1392
ThrAlaMetArgLeuGlnProArgSerAspArgLeuAlaSerGluVal
                 450                 455                 460 ctgcaaacctrcacgtrctgataatacgcggtctctcagatcggtac         1440
LeuGlnThrSerArgLeuIleIleSerArgPheLeuGlnIleArgTyr
465                 470                 475                 480 tctaccgcattaagctrtgtcgaccaagtctatttcattgtcggctac        1488
SerThrAlaLeuSerLeuValAspGlnValTyrPheIleValGlyTyr
                 485                 490                 495 gctgcactgaatctgtgcgattrtctcatgagaccccgctrtatcgag         1536
AlaAlaLeuAsnLeuCysAspPheAsnLeuMetAspProLeuIleGlu
                         500                 505                 510 caagtgcagatgtrtcctgctgcatctrtccccgaacgaagacacatc         1584
GlnValGlnMetPheLeuLeuHisLeuSerProAsnGluAspHisIle
         515                 520                 525
```

```
gcc tac cgg ttt tcg tgc atg gtc gcc gag ttc aag cgg cga tgt ggc     1632
Ala Tyr Arg Phe Ser Cys Met Val Ala Glu Phe Lys Arg Arg Cys Gly
    530                 535                 540 agt gcg gaa tgc aat gac cca tca tcc act gtc aag ggg tct ccg tta     1680
Ser Ala Glu Cys Asn Asp Pro Ser Ser Thr Val Lys Gly Ser Pro Leu
545                 550                 555                 560 tca tcc tac ggc gac agt cgt aag atg agc atg ggg caa gca ccg ttc     1728
Ser Ser Tyr Gly Asp Ser Arg Lys Met Ser Met Gly Gln Ala Pro Phe
                565                 570                 575 atg cca ccg ctc atg gat ggc atg atc gag ggg tac ggc ttc gag caa     1776
Met Pro Pro Leu Met Asp Gly Met Ile Glu Gly Tyr Gly Phe Glu Gln
            580                 585                 590 ctg atg cca gaa gtc atg ccg agt tcc ttt ccg gat ggg ata ctc aac     1824
Leu Met Pro Glu Val Met Pro Ser Ser Phe Pro Asp Gly Ile Leu Asn
        595                 600                 605 gga atg cct gtg act ggg cta gca gcg tat cgg tca gcg acg ctg taa     1872
Gly Met Pro Val Thr Gly Leu Ala Ala Tyr Arg Ser Ala Thr Leu
    610                 615                 620
```

<210> SEQ ID NO 3
<211> LENGTH: 623
<212> TYPE: PRT
<213> ORGANISM: Aspergillus niger

<400> SEQUENCE: 3

```
Met Thr Arg Thr Val Asp Glu Ile Lys Tyr Glu Thr Pro Ser Ser Trp
1               5                   10                  15

Glu His Lys Ser Leu Asp Val Ala Glu Asp Gly Arg Arg Leu Ala Pro
            20                  25                  30

His Ser Asp Thr Ala Arg Pro Lys Gly Arg Ile Arg Arg Ser Met Thr
        35                  40                  45

Ala Cys His Thr Cys Arg Lys Leu Lys Thr Arg Cys Asp Leu Asp Pro
    50                  55                  60

Arg Gly His Ala Cys Arg Arg Cys Leu Ser Leu Arg Ile Asp Cys Lys
65                  70                  75                  80

Leu Pro Glu Thr Thr Asp Arg Phe Gln Asp Ser Ala Ala Met Trp Pro
                85                  90                  95

Asp Ala Thr Ser Ala Ile Pro Ser Ile Glu Glu Arg Leu Thr Ser Leu
            100                 105                 110

Glu Arg Cys Met Arg Glu Met Thr Gly Met Met Arg Gln Met Leu Asp
        115                 120                 125

His Ser Pro Gly Phe Ala Asn Ala Ser Val Pro His Leu Thr Lys Ser
    130                 135                 140

Ile Ile Thr Asp Glu Asn Ala Ser Met Glu Gly Ser Pro Ser Ser Pro
145                 150                 155                 160

Phe Leu Pro Lys Pro Val Arg Leu Ile Gln Asp Leu Gln Ser Asp Phe
                165                 170                 175

Phe Gly Glu Ala Glu Thr Ser Pro Val Asp Ser Pro Leu Ser Ser Asp
            180                 185                 190

Gly Asn Ala Lys Gly Ala Ile Asp Ser Lys Leu Ser Leu Lys Leu Leu
        195                 200                 205

Gln Thr Phe Val Asp His Phe Gly Ala Cys Val Ser Ile Tyr Asn Leu
    210                 215                 220

Ser Asp Ile His Asn Asp Met Lys Ala Pro Asp Ser Leu Leu Tyr Asn
225                 230                 235                 240

Thr Ala Cys Leu Leu Ala Ser Arg Tyr Val Pro Gly Ile Pro Thr Ser
                245                 250                 255
```

-continued

```
Thr Val His Ala Ile Tyr Leu Gln Val Arg His Ala Val Val Asn Ile
            260                 265                 270

Leu Trp Glu Lys Pro Pro Leu Lys Tyr Glu Thr Leu Gln Ala Leu Ala
275                 280                 285

Leu Leu Cys Leu Trp Pro Ala Thr Ala Gln Lys Glu Pro Pro Met Asp
    290                 295                 300

Ser Trp Leu Leu Ser Gly Ile Ser Ile Asn His Ala Ile Ala Leu
305                 310                 315                 320

Asp Phe Leu Asn Tyr Ala Pro Ser Glu Val Met Val Asp Asn Glu Thr
                325                 330                 335

Ala Ala Gln Leu Arg Leu Trp Asn Thr Tyr Cys Leu Thr Gln Leu His
            340                 345                 350

Phe Ala Val Gly Asn Ala Arg Pro Phe His Ile Gln Gln Arg Tyr Leu
        355                 360                 365

Asp His Cys Pro Arg Ile Leu Glu His Pro Ala Ala Thr Leu Glu Asp
    370                 375                 380

Ala Arg Val Val Ala Glu Ile Gln Leu Tyr Leu Met Thr Leu Arg Leu
385                 390                 395                 400

Gln Ser Asn Ser Ser Arg Met Arg Leu Ala Asp Leu Asp Tyr Glu Glu
                405                 410                 415

Ile Glu Arg Trp Lys Arg Glu Trp Ala His Leu Phe Ser Gly Glu Ser
            420                 425                 430

Ser Thr Leu Glu Leu Ser Leu Trp Phe Cys Gln Thr Leu Leu His Arg
        435                 440                 445

Thr Ala Met Arg Leu Gln Pro Arg Ser Asp Arg Leu Ala Ser Glu Val
    450                 455                 460

Leu Gln Thr Ser Arg Leu Ile Ile Ser Arg Phe Leu Gln Ile Arg Tyr
465                 470                 475                 480

Ser Thr Ala Leu Ser Leu Val Asp Gln Val Tyr Phe Ile Val Gly Tyr
                485                 490                 495

Ala Ala Leu Asn Leu Cys Asp Phe Asn Leu Met Asp Pro Leu Ile Glu
            500                 505                 510

Gln Val Gln Met Phe Leu Leu His Leu Ser Pro Asn Glu Asp His Ile
        515                 520                 525

Ala Tyr Arg Phe Ser Cys Met Val Ala Glu Phe Lys Arg Arg Cys Gly
    530                 535                 540

Ser Ala Glu Cys Asn Asp Pro Ser Ser Thr Val Lys Gly Ser Pro Leu
545                 550                 555                 560

Ser Ser Tyr Gly Asp Ser Arg Lys Met Ser Met Gly Gln Ala Pro Phe
                565                 570                 575

Met Pro Pro Leu Met Asp Gly Met Ile Glu Gly Tyr Gly Phe Glu Gln
            580                 585                 590

Leu Met Pro Glu Val Met Pro Ser Ser Phe Pro Asp Gly Ile Leu Asn
        595                 600                 605

Gly Met Pro Val Thr Gly Leu Ala Ala Tyr Arg Ser Ala Thr Leu
    610                 615                 620

<210> SEQ ID NO 4
<211> LENGTH: 42
<212> TYPE: PRT
<213> ORGANISM: Aspergillus niger
<220> FEATURE:
<221> NAME/KEY: ZN_FING
<222> LOCATION: (1)..(42)

<400> SEQUENCE: 4
```

```
Met Thr Ala Cys His Thr Cys Arg Lys Leu Lys Thr Arg Cys Asp Leu
1               5                   10                  15

Asp Pro Arg Gly His Ala Cys Arg Arg Cys Leu Ser Leu Arg Ile Asp
            20                  25                  30

Cys Lys Leu Pro Glu Thr Thr Asp Arg Phe
            35                  40
```

<210> SEQ ID NO 5
<211> LENGTH: 25
<212> TYPE: DNA
<213> ORGANISM: Artificial sequence
<220> FEATURE:
<223> OTHER INFORMATION: Oligonucleotide designed as PCR primer to
      generate a DNA fragment in the polymerase chain reaction

<400> SEQUENCE: 5
gggagtgggc tcaccttttc tctgg                                    25

<210> SEQ ID NO 6
<211> LENGTH: 22
<212> TYPE: DNA
<213> ORGANISM: Artificial sequence
<220> FEATURE:
<223> OTHER INFORMATION: Oligonucleotide designed as PCR primer to
      generate a DNA fragment in the polymerase chain reaction

<400> SEQUENCE: 6
atgaacggtg cttgccccat gc                                       22

<210> SEQ ID NO 7
<211> LENGTH: 29
<212> TYPE: DNA
<213> ORGANISM: Artificial sequence
<220> FEATURE:
<223> OTHER INFORMATION: Oligonucleotide designed as PCR primer to
      generate a DNA fragment in the polymerase chain reaction

<400> SEQUENCE: 7
cggcttcgaa tggctaggtg tcgattttg                                29

<210> SEQ ID NO 8
<211> LENGTH: 41
<212> TYPE: DNA
<213> ORGANISM: Artificial sequence
<220> FEATURE:
<223> OTHER INFORMATION: Oligonucleotide designed as PCR primer to
      generate a DNA fragment in the polymerase chain reaction

<400> SEQUENCE: 8
ggtagtggat cgtgtggaat tggcaggcaa tctggagagt a                  41

<210> SEQ ID NO 9
<211> LENGTH: 21
<212> TYPE: DNA
<213> ORGANISM: Artificial sequence
<220> FEATURE:
<223> OTHER INFORMATION: Oligonucleotide designed as PCR primer to
      generate a DNA fragment in the polymerase chain reaction

<400> SEQUENCE: 9
aattccacac gatccactac c                                        21

<210> SEQ ID NO 10
<211> LENGTH: 32
<212> TYPE: DNA
<213> ORGANISM: Artificial sequence
<220> FEATURE:

-continued

<223> OTHER INFORMATION: Oligonucleotide designed as PCR primer to
      generate a DNA fragment in the polymerase chain reaction

<400> SEQUENCE: 10
actaggcgcg cctttgtttg gtcgatcgga ga                                  32

<210> SEQ ID NO 11
<211> LENGTH: 31
<212> TYPE: DNA
<213> ORGANISM: Artificial sequence
<220> FEATURE:
<223> OTHER INFORMATION: Oligonucleotide designed as PCR primer to
      generate a DNA fragment in the polymerase chain reaction

<400> SEQUENCE: 11
ttgaggtacc aattccacac gatccactac c                                   31

<210> SEQ ID NO 12
<211> LENGTH: 30
<212> TYPE: DNA
<213> ORGANISM: Artificial sequence
<220> FEATURE:
<223> OTHER INFORMATION: Oligonucleotide designed as PCR primer to
      generate a DNA fragment in the polymerase chain reaction

<400> SEQUENCE: 12
tcatcccggg cgtccatcgc attgattctt                                     30

<210> SEQ ID NO 13
<211> LENGTH: 2931
<212> TYPE: DNA
<213> ORGANISM: Aspergillus oryzae
<220> FEATURE:
<221> NAME/KEY: exon
<222> LOCATION: (795)..(1027)
<220> FEATURE:
<221> NAME/KEY: Intron
<222> LOCATION: (1028)..(1135)
<220> FEATURE:
<221> NAME/KEY: exon
<222> LOCATION: (1136)..(1537)
<220> FEATURE:
<221> NAME/KEY: Intron
<222> LOCATION: (1538)..(1591)
<220> FEATURE:
<221> NAME/KEY: exon
<222> LOCATION: (1592)..(2017)
<220> FEATURE:
<221> NAME/KEY: Intron
<222> LOCATION: (2018)..(2066)
<220> FEATURE:
<221> NAME/KEY: exon
<222> LOCATION: (2067)..(2295)
<220> FEATURE:
<221> NAME/KEY: Intron
<222> LOCATION: (2296)..(2346)
<220> FEATURE:
<221> NAME/KEY: exon
<222> LOCATION: (2347)..(2931)

<400> SEQUENCE: 13
gatatctcat gatctgcgtg atcggcttgc ctcctatctt agatcacccg ggcttcttca    60
aatcagcaac aacgctcaga catgtcccct gagaggtgat ccaaatcata cacgagagaa   120
cgcggaaacg caaattaagg atgagcgaaa aagagaaaaa aatccgttgt tcctgagtca   180
tgacgaatga gcaaaagtca aacacacctt ctgcttttgg ggggtatgcc cgatcacaat   240
cttcaacccg cctgataag agacacacgc tatcgacaaa tcaccggagg tcaagattag   300
tggcagtcct tagctaattt caggtcggcg tcaacccttag ccaacccaac ccaaccccct   360

-continued

```
catggaagcg ggactccota tggagccggc ttacatcggg cgcactgcaa tggcgcacgt     420
caatcaaccc ctctcttgtt gcagtgccta gtatgccaaa ccacccttc tattcttcta     480 gaaaccacac cctagagact cggatctaca cggattggtt ggaatgctcc gattagttgg    540
catttacccc aggtcaaaat ggataatcaa tctaacggag tctatttcgt caactgcctg    600
ccagctagca caatctcctc ttcacgcccg gccgtgggct gttaaaaggg tcaattccct    660
ccccacctgt gtggattctc tatgatttgc acgggatctg acttggtttc cacaattctt    720
cttgctctca gcttgttcta ctcgccgatt attcttttca tcaacgcggc acactacccc    780
cgttgtctga tgtc atg act aga act act gtt gaa cct atc aaa tat gag      830
              Met Thr Arg Thr Thr Val Glu Pro Ile Lys Tyr Glu
              1               5                   10 gcc cct tcg tgg gag cat aag agc gtg cat gtg tcc gac gac cac agg      878
Ala Pro Ser Trp Glu His Lys Ser Val His Val Ser Asp Asp His Arg
        15                  20                  25 aga atc atc ccc aat gtc ggc gac gac gcg acg cgc cca aag ggc cgc      926
Arg Ile Ile Pro Asn Val Gly Asp Asp Ala Thr Arg Pro Lys Gly Arg
    30                  35                  40 att aga cgt tca atg acc gct tgt aat acc tgc cgc aag ctt aaa act      974
Ile Arg Arg Ser Met Thr Ala Cys Asn Thr Cys Arg Lys Leu Lys Thr
45                  50                  55                  60 cgg tgc gat ctt gat cca cga ggg cat gca tgc cgg cgg tgt cta tct     1022
Arg Cys Asp Leu Asp Pro Arg Gly His Ala Cys Arg Arg Cys Leu Ser
                65                  70                  75 tta ag  gtcgggtgcc accgttatcc actttgtcaa atctcttacg tcaaaatggg      1077
Leu Arg ggatcccatg tcctgccaag accaaataag cctttcttga gtactaatgt ttctatag g   1136 atc gac tgt cag ctc ccc gag acg agt gag cgc ttt cag gac agt act     1184
Ile Asp Cys Gln Leu Pro Glu Thr Ser Glu Arg Phe Gln Asp Ser Thr
80                  85                  90 cca atg tgg tca gac gca acg aca gct atc ccc tcc atc gag gag cgt     1232
Pro Met Trp Ser Asp Ala Thr Thr Ala Ile Pro Ser Ile Glu Glu Arg
95                  100                 105                 110 ctc act tcc cta gag agg agt atg aga gag atg acc ggc atg ctt cgg     1280
Leu Thr Ser Leu Glu Arg Ser Met Arg Glu Met Thr Gly Met Leu Arg
            115                 120                 125 cag atc ttg aat caa tca cca agc gtc tct aat atc tcc gtc cct ccg     1328
Gln Ile Leu Asn Gln Ser Pro Ser Val Ser Asn Ile Ser Val Pro Pro
        130                 135                 140 cta gct cgg agt gtt cat acg gaa gaa acg gcc tcc att gaa gga aac     1376
Leu Ala Arg Ser Val His Thr Glu Glu Thr Ala Ser Ile Glu Gly Asn
145                 150                 155 tca ttc ggt cct ttc cta cct aaa ccc gtt cgg cta att cag gac ctc     1424
Ser Phe Gly Pro Phe Leu Pro Lys Pro Val Arg Leu Ile Gln Asp Leu
            160                 165                 170 caa tct gag ttt ttt ggg gag aca aac cgc atc cct gtt gaa tct cct     1472
Gln Ser Glu Phe Phe Gly Glu Thr Asn Arg Ile Pro Val Glu Ser Pro
175                 180                 185                 190 ttc ttg ggt aac agt ttt gag aag ggt atc tta gat tct aag ttg tct     1520
Phe Leu Gly Asn Ser Phe Glu Lys Gly Ile Leu Asp Ser Lys Leu Ser
                195                 200                 205 ctc aag ttg gta cag ct gtatggtcac tcgtcatgtc catctgcctc             1567
Leu Lys Leu Val Gln Leu
                210 tatagccgct aatgcttgag ctag a ttt gtg gat aat ttc ggc cct tta gtg    1619
                          Phe Val Asp Asn Phe Gly Pro Leu Val
                                          215                 220 tcc ata aat aat cag tcg gac ttc cac aac gag atg agg aac acc gat     1667
```

```
                Ser Ile Asn Asn Gln Ser Asp Phe His Asn Glu Met Arg Asn Thr Asp
                            225                 230                 235 tcg ttg tta tat agt act gcc tgt ctt ctg gcc tcc cga tat gtg cca         1715
Ser Leu Leu Tyr Ser Thr Ala Cys Leu Leu Ala Ser Arg Tyr Val Pro
            240                 245                 250 ggc ata cca cca ccg att gtc cat acc atg aac ctc caa gtt cga cat         1763
Gly Ile Pro Pro Pro Ile Val His Thr Met Asn Leu Gln Val Arg His
    255                 260                 265 aag gca gtc aat ctg ctg tgg gaa gaa ccg cct ttg aaa tac gaa tcg         1811
Lys Ala Val Asn Leu Leu Trp Glu Glu Pro Pro Leu Lys Tyr Glu Ser
270                 275                 280                 285 ctc cag gca ctc gcc ctt ctt tgt tta tgg cca gcg gcg ggt caa aag         1859
Leu Gln Ala Leu Ala Leu Leu Cys Leu Trp Pro Ala Ala Gly Gln Lys
            290                 295                 300 gag ttc ccc ata gat ggc tgg tta ctg agc ggg act gca atc aat cat         1907
Glu Phe Pro Ile Asp Gly Trp Leu Leu Ser Gly Thr Ala Ile Asn His
            305                 310                 315 gcc ctc gtc tcc ttt gac ttc ctc aat cat gtg cct tca gag ctt ctc         1955
Ala Leu Val Ser Phe Asp Phe Leu Asn His Val Pro Ser Glu Leu Leu
            320                 325                 330 att gat aac gat atc gcc gct caa ttg cgg ctc tgg aac gct ttc tgt         2003
Ile Asp Asn Asp Ile Ala Ala Gln Leu Arg Leu Trp Asn Ala Phe Cys
            335                 340                 345 tta aca cag tta ca gtaggtacaa catttccggc ttaactccaa cttgctaatg          2057
Leu Thr Gln Leu His
350 cagaaatag t ttc gct gtt ggc aac gca cgt cca ttc cat tta cca cag         2106
            Phe Ala Val Gly Asn Ala Arg Pro Phe His Leu Pro Gln
                355                 360                 365 aga tat ctc gat tat tgc cca cga ctt ctt gag cac ccc gct gca aca         2154
Arg Tyr Leu Asp Tyr Cys Pro Arg Leu Leu Glu His Pro Ala Ala Thr
            370                 375                 380 gtt gag gat ggc aag gtc gta gca gag atc cag ttg tac ttg atc aca         2202
Val Glu Asp Gly Lys Val Val Ala Glu Ile Gln Leu Tyr Leu Ile Thr
385                 390                 395 ttg cga ctc caa gcc aac gag caa cgt atg cga ttc gcg gag gtt gaa         2250
Leu Arg Leu Gln Ala Asn Glu Gln Arg Met Arg Phe Ala Glu Val Glu
400                 405                 410                 415 tac gaa gag att gaa cga tgg aaa gtt gaa tgg gcc cat ctt ctt             2295
Tyr Glu Glu Ile Glu Arg Trp Lys Val Glu Trp Ala His Leu Leu
            420                 425                 430 ggtaaggtta agcaacgagg accatctcat ataaatgcta actattcaac a gct ggt        2352
                                                         Ala Gly gat gaa aat tca aca ttt gag ctt agt ctc tgg ttc tgt caa atc ctc         2400
Asp Glu Asn Ser Thr Phe Glu Leu Ser Leu Trp Phe Cys Gln Ile Leu
            435                 440                 445 ctg cat cgg aca gca atg agg ttc caa gcg gag tct gag aga ctc acg         2448
Leu His Arg Thr Ala Met Arg Phe Gln Ala Glu Ser Glu Arg Leu Thr
450                 455                 460 tcg gaa att ctc caa gga tcg cgc ttg atc atc tcg aaa ttc ctg caa         2496
Ser Glu Ile Leu Gln Gly Ser Arg Leu Ile Ile Ser Lys Phe Leu Gln
465                 470                 475                 480 ctc cga ttt gtc acc gct cta aga gtg gtc gat cag gcg tac ttc atc         2544
Leu Arg Phe Val Thr Ala Leu Arg Val Val Asp Gln Ala Tyr Phe Ile
            485                 490                 495 gtc ggt tat gcc gct cta aat ctt tgc gac ttc aac ttc ctc gac ccc         2592
Val Gly Tyr Ala Ala Leu Asn Leu Cys Asp Phe Asn Phe Leu Asp Pro
            500                 505                 510 ctc att gac cag atc cag atg ttt ctg ctg cat ctg tcg cca aac gaa         2640
Leu Ile Asp Gln Ile Gln Met Phe Leu Leu His Leu Ser Pro Asn Glu
```

```
                 515                 520                 525
gac cac atc gca tac cgg ttt tcg tgc atg ata gcc gag ttc aag cgt        2688
Asp His Ile Ala Tyr Arg Phe Ser Cys Met Ile Ala Glu Phe Lys Arg
        530                 535                 540 cgc tgt gcc gaa tgc aac gac cct tgc agc gca gtc gac ggt tct caa        2736
Arg Cys Ala Glu Cys Asn Asp Pro Cys Ser Ala Val Asp Gly Ser Gln
545                 550                 555                 560 tgc tcg ttc gga gat gcc cgg aag atg agc atg gaa cag gta caa ttc        2784
Cys Ser Phe Gly Asp Ala Arg Lys Met Ser Met Glu Gln Val Gln Phe
                565                 570                 575 gtg cca cca cta gta gat agc atg att ggg gga tat agc gct ctg gaa        2832
Val Pro Pro Leu Val Asp Ser Met Ile Gly Gly Tyr Ser Ala Leu Glu
            580                 585                 590 cag ctg atc cct gag gtc atg cca cac tca ttt ccg gaa agt gtc ata        2880
Gln Leu Ile Pro Glu Val Met Pro His Ser Phe Pro Glu Ser Val Ile
        595                 600                 605 agt ggc atg gct gtg act gaa gcc atc cct gtg gga tcg gcg cca tac        2928
Ser Gly Met Ala Val Thr Glu Ala Ile Pro Val Gly Ser Ala Pro Tyr
    610                 615                 620 tag                                                                    2931

<210> SEQ ID NO 14
<211> LENGTH: 1875
<212> TYPE: DNA
<213> ORGANISM: Aspergillus oryzae
<220> FEATURE:
<221> NAME/KEY: exon
<222> LOCATION: (1)..(233)
<220> FEATURE:
<221> NAME/KEY: exon
<222> LOCATION: (234)..(635)
<220> FEATURE:
<221> NAME/KEY: exon
<222> LOCATION: (636)..(1061)
<220> FEATURE:
<221> NAME/KEY: exon
<222> LOCATION: (1062)..(1291)
<220> FEATURE:
<221> NAME/KEY: exon
<222> LOCATION: (1292)..(1875)

<400> SEQUENCE: 14 atg act aga act act gtt gaa cct atc aaa tat gag gcc cct tcg tgg         48
Met Thr Arg Thr Thr Val Glu Pro Ile Lys Tyr Glu Ala Pro Ser Trp
1               5                   10                  15 gag cat aag agc gtg cat gtg tcc gac gac cac agg aga atc atc ccc         96
Glu His Lys Ser Val His Val Ser Asp Asp His Arg Arg Ile Ile Pro
            20                  25                  30 aat gtc ggc gac gac gcg acg cgc cca aag ggc cgc att aga cgt tca        144
Asn Val Gly Asp Asp Ala Thr Arg Pro Lys Gly Arg Ile Arg Arg Ser
        35                  40                  45 atg acc gct tgt aat acc tgc cgc aag ctt aaa act cgg tgc gat ctt        192
Met Thr Ala Cys Asn Thr Cys Arg Lys Leu Lys Thr Arg Cys Asp Leu
    50                  55                  60 gat cca cga ggg cat gca tgc cgg cgg tgt cta tct tta ag  g atc gac      240
Asp Pro Arg Gly His Ala Cys Arg Arg Cys Leu Ser Leu Arg     Ile Asp
65                  70                  75                      80 tgt cag ctc ccc gag acg agt gag cgc ttt cag gac agt act cca atg        288
Cys Gln Leu Pro Glu Thr Ser Glu Arg Phe Gln Asp Ser Thr Pro Met
                85                  90                  95 tgg tca gac gca acg aca gct atc ccc tcc atc gag gag cgt ctc act        336
Trp Ser Asp Ala Thr Thr Ala Ile Pro Ser Ile Glu Glu Arg Leu Thr
            100                 105                 110 tcc cta gag agg agt atg aga gag atg acc ggc atg ctt cgg cag atc        384
```

```
Ser Leu Glu Arg Ser Met Arg Glu Met Thr Gly Met Leu Arg Gln Ile
        115                 120                 125 ttg aat caa tca cca agc gtc tct aat atc tcc gtc cct ccg cta gct    432
Leu Asn Gln Ser Pro Ser Val Ser Asn Ile Ser Val Pro Pro Leu Ala
    130                 135                 140 cgg agt gtt cat acg gaa gaa acg gcc tcc att gaa gga aac tca ttc    480
Arg Ser Val His Thr Glu Glu Thr Ala Ser Ile Glu Gly Asn Ser Phe
145                 150                 155                 160 ggt cct ttc cta cct aaa ccc gtt cgg cta att cag gac ctc caa tct    528
Gly Pro Phe Leu Pro Lys Pro Val Arg Leu Ile Gln Asp Leu Gln Ser
                165                 170                 175 gag ttt ttt ggg gag aca aac cgc atc cct gtt gaa tct cct ttc ttg    576
Glu Phe Phe Gly Glu Thr Asn Arg Ile Pro Val Glu Ser Pro Phe Leu
            180                 185                 190 ggt aac agt ttt gag aag ggt atc tta gat tct aag ttg tct ctc aag    624
Gly Asn Ser Phe Glu Lys Gly Ile Leu Asp Ser Lys Leu Ser Leu Lys
        195                 200                 205 ttg gta cag ct  a ttt gtg gat aat ttc ggc cct tta gtg tcc ata aat   672
Leu Val Gln Leu   Phe Val Asp Asn Phe Gly Pro Leu Val Ser Ile Asn
    210                 215                 220 aat cag tcg gac ttc cac aac gag atg agg aac acc gat tcg ttg tta    720
Asn Gln Ser Asp Phe His Asn Glu Met Arg Asn Thr Asp Ser Leu Leu
225                 230                 235                 240 tat agt act gcc tgt ctt ctg gcc tcc cga tat gtg cca ggc ata cca    768
Tyr Ser Thr Ala Cys Leu Leu Ala Ser Arg Tyr Val Pro Gly Ile Pro
                245                 250                 255 cca ccg att gtc cat acc atg aac ctc caa gtt cga cat aag gca gtc    816
Pro Pro Ile Val His Thr Met Asn Leu Gln Val Arg His Lys Ala Val
            260                 265                 270 aat ctg ctg tgg gaa gaa ccg cct ttg aaa tac gaa tcg ctc cag gca    864
Asn Leu Leu Trp Glu Glu Pro Pro Leu Lys Tyr Glu Ser Leu Gln Ala
        275                 280                 285 ctc gcc ctt ctt tgt tta tgg cca gcg gcg ggt caa aag gag ttc ccc    912
Leu Ala Leu Leu Cys Leu Trp Pro Ala Ala Gly Gln Lys Glu Phe Pro
    290                 295                 300 ata gat ggc tgg tta ctg agc ggg act gca atc aat cat gcc ctc gtc    960
Ile Asp Gly Trp Leu Leu Ser Gly Thr Ala Ile Asn His Ala Leu Val
305                 310                 315                 320 tcc ttt gac ttc ctc aat cat gtg cct tca gag ctt ctc att gat aac    1008
Ser Phe Asp Phe Leu Asn His Val Pro Ser Glu Leu Leu Ile Asp Asn
                325                 330                 335 gat atc gcc gct caa ttg cgg ctc tgg aac gct ttc tgt tta aca cag    1056
Asp Ile Ala Ala Gln Leu Arg Leu Trp Asn Ala Phe Cys Leu Thr Gln
            340                 345                 350 tta ca  t ttc gct gtt ggc aac gca cgt cca ttc cat tta cca cag aga  1104
Leu His   Phe Ala Val Gly Asn Ala Arg Pro Phe His Leu Pro Gln Arg
        355                 360                 365 tat ctc gat tat tgc cca cga ctt ctt gag cac ccc gct gca aca gtt    1152
Tyr Leu Asp Tyr Cys Pro Arg Leu Leu Glu His Pro Ala Ala Thr Val
    370                 375                 380 gag gat ggc aag gtc gta gca gag atc cag ttg tac ttg atc aca ttg    1200
Glu Asp Gly Lys Val Val Ala Glu Ile Gln Leu Tyr Leu Ile Thr Leu
385                 390                 395                 400 cga ctc caa gcc aac gag caa cgt atg cga ttc gcg gag gtt gaa tac    1248
Arg Leu Gln Ala Asn Glu Gln Arg Met Arg Phe Ala Glu Val Glu Tyr
                405                 410                 415 gaa gag att gaa cga tgg aaa gtt gaa tgg gcc cat ctt ctt g ct  ggt   1296
Glu Glu Ile Glu Arg Trp Lys Val Glu Trp Ala His Leu Leu   Ala Gly
            420                 425                 430 gat gaa aat tca aca ttt gag ctt agt ctc tgg ttc tgt caa atc ctc    1344
```

```
                Asp Glu Asn Ser Thr Phe Glu Leu Ser Leu Trp Phe Cys Gln Ile Leu
                            435                 440                 445 ctg cat cgg aca gca atg agg ttc caa gcg gag tct gag aga ctc acg          1392
Leu His Arg Thr Ala Met Arg Phe Gln Ala Glu Ser Glu Arg Leu Thr
    450                 455                 460 tcg gaa att ctc caa gga tcg cgc ttg atc atc tcg aaa ttc ctg caa          1440
Ser Glu Ile Leu Gln Gly Ser Arg Leu Ile Ile Ser Lys Phe Leu Gln
465                 470                 475                 480 ctc cga ttt gtc acc gct cta aga gtg gtc gat cag gcg tac ttc atc          1488
Leu Arg Phe Val Thr Ala Leu Arg Val Val Asp Gln Ala Tyr Phe Ile
                485                 490                 495 gtc ggt tat gcc gct cta aat ctt tgc gac ttc aac ttc ctc gac ccc          1536
Val Gly Tyr Ala Ala Leu Asn Leu Cys Asp Phe Asn Phe Leu Asp Pro
            500                 505                 510 ctc att gac cag atc cag atg ttt ctg ctg cat ctg tcg cca aac gaa          1584
Leu Ile Asp Gln Ile Gln Met Phe Leu Leu His Leu Ser Pro Asn Glu
        515                 520                 525 gac cac atc gca tac cgg ttt tcg tgc atg ata gcc gag ttc aag cgt          1632
Asp His Ile Ala Tyr Arg Phe Ser Cys Met Ile Ala Glu Phe Lys Arg
    530                 535                 540 cgc tgt gcc gaa tgc aac gac cct tgc agc gca gtc gac ggt tct caa          1680
Arg Cys Ala Glu Cys Asn Asp Pro Cys Ser Ala Val Asp Gly Ser Gln
545                 550                 555                 560 tgc tcg ttc gga gat gcc cgg aag atg agc atg gaa cag gta caa ttc          1728
Cys Ser Phe Gly Asp Ala Arg Lys Met Ser Met Glu Gln Val Gln Phe
                565                 570                 575 gtg cca cca cta gta gat agc atg att ggg gga tat agc gct ctg gaa          1776
Val Pro Pro Leu Val Asp Ser Met Ile Gly Gly Tyr Ser Ala Leu Glu
            580                 585                 590 cag ctg atc cct gag gtc atg cca cac tca ttt ccg gaa agt gtc ata          1824
Gln Leu Ile Pro Glu Val Met Pro His Ser Phe Pro Glu Ser Val Ile
        595                 600                 605 agt ggc atg gct gtg act gaa gcc atc cct gtg gga tcg gcg cca tac          1872
Ser Gly Met Ala Val Thr Glu Ala Ile Pro Val Gly Ser Ala Pro Tyr
    610                 615                 620 tag                                                                      1875

<210> SEQ ID NO 15
<211> LENGTH: 624
<212> TYPE: PRT
<213> ORGANISM: Aspergillus oryzae

<400> SEQUENCE: 15

Met Thr Arg Thr Thr Val Glu Pro Ile Lys Tyr Glu Ala Pro Ser Trp
1               5                   10                  15

Glu His Lys Ser Val His Val Ser Asp Asp His Arg Arg Ile Ile Pro
            20                  25                  30

Asn Val Gly Asp Asp Ala Thr Arg Pro Lys Gly Arg Ile Arg Arg Ser
        35                  40                  45

Met Thr Ala Cys Asn Thr Cys Arg Lys Leu Lys Thr Arg Cys Asp Leu
    50                  55                  60

Asp Pro Arg Gly His Ala Cys Arg Cys Leu Ser Leu Arg Ile Asp
65                  70                  75                  80

Cys Gln Leu Pro Glu Thr Ser Glu Arg Phe Gln Asp Ser Thr Pro Met
                85                  90                  95

Trp Ser Asp Ala Thr Thr Ala Ile Pro Ser Ile Glu Glu Arg Leu Thr
            100                 105                 110

Ser Leu Glu Arg Ser Met Arg Glu Met Thr Gly Met Leu Arg Gln Ile
        115                 120                 125
```

```
Leu Asn Gln Ser Pro Ser Val Ser Asn Ile Ser Val Pro Pro Leu Ala
    130                 135                 140

Arg Ser Val His Thr Glu Glu Thr Ala Ser Ile Glu Gly Asn Ser Phe
145                 150                 155                 160

Gly Pro Phe Leu Pro Lys Pro Val Arg Leu Ile Gln Asp Leu Gln Ser
                165                 170                 175

Glu Phe Phe Gly Glu Thr Asn Arg Ile Pro Val Glu Ser Pro Phe Leu
            180                 185                 190

Gly Asn Ser Phe Glu Lys Gly Ile Leu Asp Ser Lys Leu Ser Leu Lys
        195                 200                 205

Leu Val Gln Leu Phe Val Asp Asn Phe Gly Pro Leu Val Ser Ile Asn
    210                 215                 220

Asn Gln Ser Asp Phe His Asn Glu Met Arg Asn Thr Asp Ser Leu Leu
225                 230                 235                 240

Tyr Ser Thr Ala Cys Leu Leu Ala Ser Arg Tyr Val Pro Gly Ile Pro
                245                 250                 255

Pro Pro Ile Val His Thr Met Asn Leu Gln Val Arg His Lys Ala Val
            260                 265                 270

Asn Leu Leu Trp Glu Glu Pro Pro Leu Lys Tyr Glu Ser Leu Gln Ala
        275                 280                 285

Leu Ala Leu Leu Cys Leu Trp Pro Ala Ala Gly Gln Lys Glu Phe Pro
    290                 295                 300

Ile Asp Gly Trp Leu Leu Ser Gly Thr Ala Ile Asn His Ala Leu Val
305                 310                 315                 320

Ser Phe Asp Phe Leu Asn His Val Pro Ser Glu Leu Leu Ile Asp Asn
                325                 330                 335

Asp Ile Ala Ala Gln Leu Arg Leu Trp Asn Ala Phe Cys Leu Thr Gln
            340                 345                 350

Leu His Phe Ala Val Gly Asn Ala Arg Pro Phe His Leu Pro Gln Arg
        355                 360                 365

Tyr Leu Asp Tyr Cys Pro Arg Leu Leu Glu His Pro Ala Ala Thr Val
    370                 375                 380

Glu Asp Gly Lys Val Val Ala Glu Ile Gln Leu Tyr Leu Ile Thr Leu
385                 390                 395                 400

Arg Leu Gln Ala Asn Glu Gln Arg Met Arg Phe Ala Glu Val Glu Tyr
                405                 410                 415

Glu Glu Ile Glu Arg Trp Lys Val Glu Trp Ala His Leu Leu Ala Gly
            420                 425                 430

Asp Glu Asn Ser Thr Phe Glu Leu Ser Leu Trp Phe Cys Gln Ile Leu
        435                 440                 445

Leu His Arg Thr Ala Met Arg Phe Gln Ala Glu Ser Glu Arg Leu Thr
    450                 455                 460

Ser Glu Ile Leu Gln Gly Ser Arg Leu Ile Ile Ser Lys Phe Leu Gln
465                 470                 475                 480

Leu Arg Phe Val Thr Ala Leu Arg Val Val Asp Gln Ala Tyr Phe Ile
                485                 490                 495

Val Gly Tyr Ala Ala Leu Asn Leu Cys Asp Phe Asn Phe Leu Asp Pro
            500                 505                 510

Leu Ile Asp Gln Ile Gln Met Phe Leu Leu His Leu Ser Pro Asn Glu
        515                 520                 525

Asp His Ile Ala Tyr Arg Phe Ser Cys Met Ile Ala Glu Phe Lys Arg
    530                 535                 540

Arg Cys Ala Glu Cys Asn Asp Pro Cys Ser Ala Val Asp Gly Ser Gln
```

```
                   545                 550                 555                 560
Cys Ser Phe Gly Asp Ala Arg Lys Met Ser Met Glu Gln Val Gln Phe
                565                 570                 575

Val Pro Pro Leu Val Asp Ser Met Ile Gly Gly Tyr Ser Ala Leu Glu
        580                 585                 590

Gln Leu Ile Pro Glu Val Met Pro His Ser Phe Pro Glu Ser Val Ile
         595                 600                 605

Ser Gly Met Ala Val Thr Glu Ala Ile Pro Val Gly Ser Ala Pro Tyr
         610                 615                 620

<210> SEQ ID NO 16
<211> LENGTH: 3467
<212> TYPE: DNA
<213> ORGANISM: Aspergillus fumigatus
<220> FEATURE:
<221> NAME/KEY: exon
<222> LOCATION: (811)..(1046)
<220> FEATURE:
<221> NAME/KEY: Intron
<222> LOCATION: (1047)..(1163)
<220> FEATURE:
<221> NAME/KEY: exon
<222> LOCATION: (1164)..(1565)
<220> FEATURE:
<221> NAME/KEY: Intron
<222> LOCATION: (1566)..(1633)
<220> FEATURE:
<221> NAME/KEY: exon
<222> LOCATION: (1634)..(2059)
<220> FEATURE:
<221> NAME/KEY: Intron
<222> LOCATION: (2060)..(2114)
<220> FEATURE:
<221> NAME/KEY: exon
<222> LOCATION: (2115)..(2344)
<220> FEATURE:
<221> NAME/KEY: Intron
<222> LOCATION: (2345)..(2395)
<220> FEATURE:
<221> NAME/KEY: exon
<222> LOCATION: (2396)..(2967)

<400> SEQUENCE: 16
ctatttgggt tggccatact aaatttaact gtatggtctc tttcaaaccc acaagggtga    60
tagcgaaaca gaagagacaa gtgaagggaa atttgattaa ggatgattag acggaccag    120 acagaggccc atcgatatcg ctgctccact gtggaaaatt taagactcaa ccgccatgat   180
gcacatccag accctccgca agattaccat cttggatgtt caagataagc aacgttgttt   240
atcaacaaat cagaatgtcc cggacaatgt cttccaacta attgcgtgct ggtgctactt   300
tcctcctttt ctttccatcg ctaaaatcaa acccctcatt gctctgaaag cgggaatttc   360
agagaacccg gttctcatcg gatgcaggag gatcaagatg gcgcatgtca gtcaacccct   420
ctttgactgc agccagcaaa gtatcgttac caccttcttc cgcctgtttc tacttttcta   480
gaagcccgct agaggcgcct cttggtggca tcgcgcccct gattagcttt taccccaggt   540
tcaagatagg ttggccggcc gtggcggcgc agaacaccta actaccagtg gagtctattt   600
cgtcaacggc tagcaagcta acaccatttc attcccctag cccatcatgg cctgttaaaa   660
aggcaattgt ctcgctccac atgtccaagc tacttaatga tttgcgctgg atcttttgtt   720
ttctggattc ccacacccgt ccgttccctc tccgcctatt agatagtcat tgtcggctg    780 ctgatccatc agtgcccata ctctgaggcc atg acg cgc acc act tct gtt gaa    834
                                Met Thr Arg Thr Thr Ser Val Glu
                                 1               5 gat gtc aaa ttt gag atc ccc gcg tgg gac aac tcg aat gtt gat gtc     882
```

-continued

```
Asp Val Lys Phe Glu Ile Pro Ala Trp Asp Asn Ser Asn Val Asp Val
     10                  15                  20 gct gac ggc agc ggc cga cca gaa tcc agt acc agc ggc gac aca ata        930
Ala Asp Gly Ser Gly Arg Pro Glu Ser Ser Thr Ser Gly Asp Thr Ile
 25                  30                  35                  40 cgt cca aaa ggt cgc ata cga cga tca atg acg gct tgt aat act tgt        978
Arg Pro Lys Gly Arg Ile Arg Arg Ser Met Thr Ala Cys Asn Thr Cys
                 45                  50                  55 cgc aag ctg aag acc cgg tgc gat tta gat cca cgc ggt cat gct tgc       1026
Arg Lys Leu Lys Thr Arg Cys Asp Leu Asp Pro Arg Gly His Ala Cys
                 60                  65                  70 cgc cgc tgt ctc tcc ttg ag gttcgtacca tagagactct acactgaagg           1076
Arg Arg Cys Leu Ser Leu Arg
                 75 atacgagacg ttcaaaatcc cgaagatctc tgttgcttca attggccggc tgggatcgaa     1136 tttttgctga acatgctttc ctcgcag g ata gag tgc aag ctg cct gag aca       1188
                               Ile Glu Cys Lys Leu Pro Glu Thr
                                80                  85 gct gag cgc ttt caa gat aat gct tca atg tgg tcg gat gcc aca gca       1236
Ala Glu Arg Phe Gln Asp Asn Ala Ser Met Trp Ser Asp Ala Thr Ala
                 90                  95                 100 gct att ccg tcc att gaa gag cgc ctc atc tcg ctg gaa cga agt atg       1284
Ala Ile Pro Ser Ile Glu Glu Arg Leu Ile Ser Leu Glu Arg Ser Met
    105                 110                 115 aca gaa atg acc agc atg atg cga cgg atg atg gac cgg tca ccc agt       1332
Thr Glu Met Thr Ser Met Met Arg Arg Met Met Asp Arg Ser Pro Ser
120                 125                 130                 135 ata tct ggc agc tcg gta tcc atg ctg aca agg agt ggt atc act gat       1380
Ile Ser Gly Ser Ser Val Ser Met Leu Thr Arg Ser Gly Ile Thr Asp
                140                 145                 150 gag acc gct tcg atc gaa ggg agt caa tcg tcc tcc ttc gct cct aga       1428
Glu Thr Ala Ser Ile Glu Gly Ser Gln Ser Ser Ser Phe Ala Pro Arg
                155                 160                 165 cct atc cgt ctc ttt cag gac ctg cag tcc gac ttc acg ggt gag gca       1476
Pro Ile Arg Leu Phe Gln Asp Leu Gln Ser Asp Phe Thr Gly Glu Ala
                170                 175                 180 aat gtc cta cct gcg gat tca agg tca ctc ggt gat ctt ttc acc aag       1524
Asn Val Leu Pro Ala Asp Ser Arg Ser Leu Gly Asp Leu Phe Thr Lys
    185                 190                 195 gga att atc gac cct aaa tta tct cag aaa tta att cag tt                1565
Gly Ile Ile Asp Pro Lys Leu Ser Gln Lys Leu Ile Gln Leu
200                 205                 210 gtatgcaacc tttctcgtct gattttgatc cgtctgagga tctctccgct aatctactca     1625 ttccaaag g ttt gtt gat cat ttt ggg atc tgg atc tcg gtc gac aat        1673
         Phe Val Asp His Phe Gly Ile Trp Ile Ser Val Asp Asn
            215                 220                 225 cca tca gat att cat aat gag ttg aga gct aca gat ccg ctg ctc tat       1721
Pro Ser Asp Ile His Asn Glu Leu Arg Ala Thr Asp Pro Leu Leu Tyr
            230                 235                 240 agt aca gct tgt ctg tta gca tct cgc tac gtc ccc ggt ata cca tta       1769
Ser Thr Ala Cys Leu Leu Ala Ser Arg Tyr Val Pro Gly Ile Pro Leu
            245                 250                 255 tcc gta atc cat gct atg tat ctt cag ata cgg cat gca aca gtc aat       1817
Ser Val Ile His Ala Met Tyr Leu Gln Ile Arg His Ala Thr Val Asn
            260                 265                 270 gtt ctc tgg aat aag aca ccc ctc aag cac gaa act ctt cag gct ctt       1865
Val Leu Trp Asn Lys Thr Pro Leu Lys His Glu Thr Leu Gln Ala Leu
275                 280                 285                 290 gct ctt ctt gcc tta tgg cct aca gca gta caa aag gag act ccg atg       1913
Ala Leu Leu Ala Leu Trp Pro Thr Ala Val Gln Lys Glu Thr Pro Met
```

```
                Ala Leu Leu Ala Leu Trp Pro Thr Ala Val Gln Lys Glu Thr Pro Met
                            295                 300                 305 gat agt tgg ttg ctg agc ggg atc tcg atc aac cac gct atc att tcc      1961
Asp Ser Trp Leu Leu Ser Gly Ile Ser Ile Asn His Ala Ile Ile Ser
            310                 315                 320 ttt gac ttt ctc aac cat gct ccg tcc gat ctt att gtg gac aat gac      2009
Phe Asp Phe Leu Asn His Ala Pro Ser Asp Leu Ile Val Asp Asn Asp
            325                 330                 335 atg gtc gcg aaa ctc cgc gtg tgg aat gct cta tgc ctg act cag tta      2057
Met Val Ala Lys Leu Arg Val Trp Asn Ala Leu Cys Leu Thr Gln Leu
            340                 345                 350 ca  gtatgtattc accgtattca agggtttaca cggcattgc taagtaggcc tctag       2114
Gln g tct gcc att gga aac gct cgc ccc ttt cac ata cag cag agg tac ctc    2163
  Ser Ala Ile Gly Asn Ala Arg Pro Phe His Ile Gln Gln Arg Tyr Leu
                360                 365                 370 gag cat tgt cca cga ctg ctt gag cac cca gct gct aca ttt gaa gac      2211
Glu His Cys Pro Arg Leu Leu Glu His Pro Ala Ala Thr Phe Glu Asp
            375                 380                 385 gga aaa att gtg gca gag atc cag tta tat ctg atc gcc cta aag ttg      2259
Gly Lys Ile Val Ala Glu Ile Gln Leu Tyr Leu Ile Ala Leu Lys Leu
            390                 395                 400 cag aat ttc agc cac cgt atg cgg ctg gga gac ttt gaa tac gag gaa      2307
Gln Asn Phe Ser His Arg Met Arg Leu Gly Asp Phe Glu Tyr Glu Glu
            405                 410                 415 atc gaa cgt tgg aag atg gag tgg gca cat ctc tta a gtaaataacc         2354
Ile Glu Arg Trp Lys Met Glu Trp Ala His Leu Leu
420                 425                 430 accgaagtct gtcacaggag gtgccctaac tgattgagca g ct  ggc gag caa cat   2409
                                                         Thr Gly Glu Gln His
                                                                     435 tcg aca tta gag ctt agc ctc tgg tat tgc caa cta cta ctc tat cga      2457
Ser Thr Leu Glu Leu Ser Leu Trp Tyr Cys Gln Leu Leu Leu Tyr Arg
            440                 445                 450 acc gca atg agg ttc cat tgg gag tcc gaa cac ctc atc tca gaa atc      2505
Thr Ala Met Arg Phe His Trp Glu Ser Glu His Leu Ile Ser Glu Ile
            455                 460                 465 ctt cga aat tcg cgc ctc atc ctc tca aaa ttc cta ttg gtc cgg ttt      2553
Leu Arg Asn Ser Arg Leu Ile Leu Ser Lys Phe Leu Leu Val Arg Phe
            470                 475                 480 ccg aac gca ctc gcc ttc cca gat cag ata tac tac atc gtg ggc tac      2601
Pro Asn Ala Leu Ala Phe Pro Asp Gln Ile Tyr Tyr Ile Val Gly Tyr
485                 490                 495                 500 gcc gcc cta aat ctc tgc gac ttt agc ccg atg gat ccg ctt atc gac      2649
Ala Ala Leu Asn Leu Cys Asp Phe Ser Pro Met Asp Pro Leu Ile Asp
            505                 510                 515 caa gtc caa acc ttc ctg ctg cat ctg tca ccg aac gaa gat cac atc      2697
Gln Val Gln Thr Phe Leu Leu His Leu Ser Pro Asn Glu Asp His Ile
            520                 525                 530 gcc tac cgc ttc tca tat aca atc aca gag ctc aag cgc cgc tgc gca      2745
Ala Tyr Arg Phe Ser Tyr Thr Ile Thr Glu Leu Lys Arg Arg Cys Ala
            535                 540                 545 aca ggg cct aac ccc cac aat gta gtc aaa ggt gcg ttc ggg gat act      2793
Thr Gly Pro Asn Pro His Asn Val Val Lys Gly Ala Phe Gly Asp Thr
            550                 555                 560 cgg aaa ctg agc atg gga cag cag ata ccc ttc atg aat cca ttg atg      2841
Arg Lys Leu Ser Met Gly Gln Gln Ile Pro Phe Met Asn Pro Leu Met
565                 570                 575                 580 gat acc atg atg ggg gag tac ggt ggc tta gag cat ctc ata ccc gaa      2889
Asp Thr Met Met Gly Glu Tyr Gly Gly Leu Glu His Leu Ile Pro Glu
```

-continued

```
                585                 590                 595
gtt cct cca aac tcc ttg ccc gac atg ctc acc agt gta gct ggt gag      2937
Val Pro Pro Asn Ser Leu Pro Asp Met Leu Thr Ser Val Ala Gly Glu
            600                 605                 610 ctg caa gcg ttt cgt aca gcg att ctt tga tattgtcaat catacatgga        2987
Leu Gln Ala Phe Arg Thr Ala Ile Leu
            615                 620 attcttgcat gcaccgtgac caatacggat gcgcctcgtg tgcgaacagc cgtccgtaca   3047
gcgcggcatt aatgtattta gttatctctt tccacagcgt gaagcaggct tcacctccct   3107
gcgtcgggcg attttcaacc ctgttttttaa ctccatttcg tcaatttaat tgtgaaaccc  3167
gctctggctt cctggcgcta ggtttcattg ggtgtaatca tagacgtttt aaagtcgatc   3227
gatgcttcgt ttggaggcgt aacgactgag gtaggtagga gactttagtc gtttaggctg   3287
tagtggccat agtctttgaa tcctctttga aagccaaata ggcacgaacg tctgaacctc    3347
gatcgcaagg ggtccattgt ccaacaatga accctcgagg gtcacttggt cctcactgag    3407
atatatgtta ttcttccgcg atatacattc tactgtagca gtgctagccc tattaatcga   3467

<210> SEQ ID NO 17
<211> LENGTH: 1866
<212> TYPE: DNA
<213> ORGANISM: Aspergillus fumigatus
<220> FEATURE:
<221> NAME/KEY: exon
<222> LOCATION: (1)..(236)
<220> FEATURE:
<221> NAME/KEY: exon
<222> LOCATION: (237)..(638)
<220> FEATURE:
<221> NAME/KEY: exon
<222> LOCATION: (639)..(1064)
<220> FEATURE:
<221> NAME/KEY: exon
<222> LOCATION: (1065)..(1293)
<220> FEATURE:
<221> NAME/KEY: exon
<222> LOCATION: (1294)..(1866)

<400> SEQUENCE: 17 atg acg cgc acc act tct gtt gaa gat gtc aaa ttt gag atc ccc gcg      48
Met Thr Arg Thr Thr Ser Val Glu Asp Val Lys Phe Glu Ile Pro Ala
1               5                   10                  15 tgg gac aac tcg aat gtt gat gtc gct gac ggc agc ggc cga cca gaa      96
Trp Asp Asn Ser Asn Val Asp Val Ala Asp Gly Ser Gly Arg Pro Glu
                20                  25                  30 tcc agt acc agc ggc gac aca ata cgt cca aaa ggt cgc ata cga cga     144
Ser Ser Thr Ser Gly Asp Thr Ile Arg Pro Lys Gly Arg Ile Arg Arg
            35                  40                  45 tca atg acg gct tgt aat act tgt cgc aag ctg aag acc cgg tgc gat     192
Ser Met Thr Ala Cys Asn Thr Cys Arg Lys Leu Lys Thr Arg Cys Asp
        50                  55                  60 tta gat cca cgc ggt cat gct tgc cgc cgc tgt ctc tcc ttg ag  g ata   240
Leu Asp Pro Arg Gly His Ala Cys Arg Arg Cys Leu Ser Leu Arg   Ile
65                  70                  75                      80 gag tgc aag ctg cct gag aca gct gag cgc ttt caa gat aat gct tca     288
Glu Cys Lys Leu Pro Glu Thr Ala Glu Arg Phe Gln Asp Asn Ala Ser
                85                  90                  95 atg tgg tcg gat gcc aca gca gct att ccg tcc att gaa gag cgc ctc     336
Met Trp Ser Asp Ala Thr Ala Ala Ile Pro Ser Ile Glu Glu Arg Leu
            100                 105                 110 atc tcg ctg gaa cga agt atg aca gaa atg acc agc atg atg cga cgg     384
Ile Ser Leu Glu Arg Ser Met Thr Glu Met Thr Ser Met Met Arg Arg
        115                 120                 125
```

```
atg atg gac cgg tca ccc agt ata tct ggc agc tcg gta tcc atg ctg      432
Met Met Asp Arg Ser Pro Ser Ile Ser Gly Ser Ser Val Ser Met Leu
130                 135                 140 aca agg agt ggt atc act gat gag acc gct tcg atc gaa ggg agt caa      480
Thr Arg Ser Gly Ile Thr Asp Glu Thr Ala Ser Ile Glu Gly Ser Gln
145                 150                 155                 160 tcg tcc tcc ttc gct cct aga cct atc cgt ctc ttt cag gac ctg cag      528
Ser Ser Ser Phe Ala Pro Arg Pro Ile Arg Leu Phe Gln Asp Leu Gln
                165                 170                 175 tcc gac ttc acg ggt gag gca aat gtc cta cct gcg gat tca agg tca      576
Ser Asp Phe Thr Gly Glu Ala Asn Val Leu Pro Ala Asp Ser Arg Ser
            180                 185                 190 ctc ggt gat ctt ttc acc aag gga att atc gac cct aaa tta tct cag      624
Leu Gly Asp Leu Phe Thr Lys Gly Ile Ile Asp Pro Lys Leu Ser Gln
        195                 200                 205 aaa tta att cag tt  g ttt gtt gat cat ttt ggg atc tgg atc tcg gtc    672
Lys Leu Ile Gln Leu   Phe Val Asp His Phe Gly Ile Trp Ile Ser Val
210                         215                 220 gac aat cca tca gat att cat aat gag ttg aga gct aca gat ccg ctg      720
Asp Asn Pro Ser Asp Ile His Asn Glu Leu Arg Ala Thr Asp Pro Leu
225                 230                 235                 240 ctc tat agt aca gct tgt ctg tta gca tct cgc tac gtc ccc ggt ata      768
Leu Tyr Ser Thr Ala Cys Leu Leu Ala Ser Arg Tyr Val Pro Gly Ile
                245                 250                 255 cca tta tcc gta atc cat gct atg tat ctt cag ata cgg cat gca aca      816
Pro Leu Ser Val Ile His Ala Met Tyr Leu Gln Ile Arg His Ala Thr
            260                 265                 270 gtc aat gtt ctc tgg aat aag aca ccc ctc aag cac gaa act ctt cag      864
Val Asn Val Leu Trp Asn Lys Thr Pro Leu Lys His Glu Thr Leu Gln
        275                 280                 285 gct ctt gct ctt ctt gcc tta tgg cct aca gca gta caa aag gag act      912
Ala Leu Ala Leu Leu Ala Leu Trp Pro Thr Ala Val Gln Lys Glu Thr
290                 295                 300 ccg atg gat agt tgg ttg ctg agc ggg atc tcg atc aac cac gct atc      960
Pro Met Asp Ser Trp Leu Leu Ser Gly Ile Ser Ile Asn His Ala Ile
305                 310                 315                 320 att tcc ttt gac ttt ctc aac cat gct ccg tcc gat ctt att gtg gac     1008
Ile Ser Phe Asp Phe Leu Asn His Ala Pro Ser Asp Leu Ile Val Asp
                325                 330                 335 aat gac atg gtc gcg aaa ctc cgc gtg tgg aat gct cta tgc ctg act     1056
Asn Asp Met Val Ala Lys Leu Arg Val Trp Asn Ala Leu Cys Leu Thr
            340                 345                 350 cag tta ca  g tct gcc att gga aac gct cgc ccc ttt cac ata cag cag   1104
Gln Leu Gln   Ser Ala Ile Gly Asn Ala Arg Pro Phe His Ile Gln Gln
        360                 365 agg tac ctc gag cat tgt cca cga ctg ctt gag cac cca gct gct aca     1152
Arg Tyr Leu Glu His Cys Pro Arg Leu Leu Glu His Pro Ala Ala Thr
        370                 375                 380 ttt gaa gac gga aaa att gtg gca gag atc cag tta tat ctg atc gcc     1200
Phe Glu Asp Gly Lys Ile Val Ala Glu Ile Gln Leu Tyr Leu Ile Ala
385                 390                 395                 400 cta aag ttg cag aat ttc agc cac cgt atg cgg ctg gga gac ttt gaa     1248
Leu Lys Leu Gln Asn Phe Ser His Arg Met Arg Leu Gly Asp Phe Glu
                405                 410                 415 tac gag gaa atc gaa cgt tgg aag atg gag tgg gca cat ctc tta act     1296
Tyr Glu Glu Ile Glu Arg Trp Lys Met Glu Trp Ala His Leu Leu Thr
            420                 425                 430 ggc gag caa cat tcg aca tta gag ctt agc ctc tgg tat tgc caa cta     1344
Gly Glu Gln His Ser Thr Leu Glu Leu Ser Leu Trp Tyr Cys Gln Leu
        435                 440                 445
```

```
cta ctc tat cga acc gca atg agg ttc cat tgg gag tcc gaa cac ctc      1392
Leu Leu Tyr Arg Thr Ala Met Arg Phe His Trp Glu Ser Glu His Leu
    450                 455                 460 atc tca gaa atc ctt cga aat tcg cgc ctc atc ctc tca aaa ttc cta      1440
Ile Ser Glu Ile Leu Arg Asn Ser Arg Leu Ile Leu Ser Lys Phe Leu
465                 470                 475                 480 ttg gtc cgg ttt ccg aac gca ctc gcc ttc cca gat cag ata tac tac      1488
Leu Val Arg Phe Pro Asn Ala Leu Ala Phe Pro Asp Gln Ile Tyr Tyr
                485                 490                 495 atc gtg ggc tac gcc gcc cta aat ctc tgc gac ttt agc ccg atg gat      1536
Ile Val Gly Tyr Ala Ala Leu Asn Leu Cys Asp Phe Ser Pro Met Asp
            500                 505                 510 ccg ctt atc gac caa gtc caa acc ttc ctg ctg cat ctg tca ccg aac      1584
Pro Leu Ile Asp Gln Val Gln Thr Phe Leu Leu His Leu Ser Pro Asn
        515                 520                 525 gaa gat cac atc gcc tac cgc ttc tca tat aca atc aca gag ctc aag      1632
Glu Asp His Ile Ala Tyr Arg Phe Ser Tyr Thr Ile Thr Glu Leu Lys
    530                 535                 540 cgc cgc tgc gca aca ggg cct aac ccc cac aat gta gtc aaa ggt gcg      1680
Arg Arg Cys Ala Thr Gly Pro Asn Pro His Asn Val Val Lys Gly Ala
545                 550                 555                 560 ttc ggg gat act cgg aaa ctg agc atg gga cag cag ata ccc ttc atg      1728
Phe Gly Asp Thr Arg Lys Leu Ser Met Gly Gln Gln Ile Pro Phe Met
                565                 570                 575 aat cca ttg atg gat acc atg atg ggg gag tac ggt ggc tta gag cat      1776
Asn Pro Leu Met Asp Thr Met Met Gly Glu Tyr Gly Gly Leu Glu His
            580                 585                 590 ctc ata ccc gaa gtt cct cca aac tcc ttg ccc gac atg ctc acc agt      1824
Leu Ile Pro Glu Val Pro Pro Asn Ser Leu Pro Asp Met Leu Thr Ser
        595                 600                 605 gta gct ggt gag ctg caa gcg ttt cgt aca gcg att ctt tga              1866
Val Ala Gly Glu Leu Gln Ala Phe Arg Thr Ala Ile Leu
    610                 615                 620

<210> SEQ ID NO 18
<211> LENGTH: 621
<212> TYPE: PRT
<213> ORGANISM: Aspergillus fumigatus

<400> SEQUENCE: 18

Met Thr Arg Thr Thr Ser Val Glu Asp Val Lys Phe Glu Ile Pro Ala
1               5                   10                  15

Trp Asp Asn Ser Asn Val Asp Val Ala Asp Gly Ser Gly Arg Pro Glu
                20                  25                  30

Ser Ser Thr Ser Gly Asp Thr Ile Arg Pro Lys Gly Arg Ile Arg Arg
            35                  40                  45

Ser Met Thr Ala Cys Asn Thr Cys Arg Lys Leu Lys Thr Arg Cys Asp
        50                  55                  60

Leu Asp Pro Arg Gly His Ala Cys Arg Arg Cys Leu Ser Leu Arg Ile
65                  70                  75                  80

Glu Cys Lys Leu Pro Glu Thr Ala Glu Arg Phe Gln Asp Asn Ala Ser
                85                  90                  95

Met Trp Ser Asp Ala Thr Ala Ala Ile Pro Ser Ile Glu Glu Arg Leu
            100                 105                 110

Ile Ser Leu Glu Arg Ser Met Thr Glu Met Thr Ser Met Met Arg Arg
        115                 120                 125

Met Met Asp Arg Ser Pro Ser Ile Ser Gly Ser Ser Val Ser Met Leu
    130                 135                 140
```

-continued

```
Thr Arg Ser Gly Ile Thr Asp Glu Thr Ala Ser Ile Glu Gly Ser Gln
145                 150                 155                 160

Ser Ser Ser Phe Ala Pro Arg Pro Ile Arg Leu Phe Gln Asp Leu Gln
            165                 170                 175

Ser Asp Phe Thr Gly Glu Ala Asn Val Leu Pro Ala Asp Ser Arg Ser
        180                 185                 190

Leu Gly Asp Leu Phe Thr Lys Gly Ile Ile Asp Pro Lys Leu Ser Gln
    195                 200                 205

Lys Leu Ile Gln Leu Phe Val Asp His Phe Gly Ile Trp Ile Ser Val
210                 215                 220

Asp Asn Pro Ser Asp Ile His Asn Glu Leu Arg Ala Thr Asp Pro Leu
225                 230                 235                 240

Leu Tyr Ser Thr Ala Cys Leu Leu Ala Ser Arg Tyr Val Pro Gly Ile
            245                 250                 255

Pro Leu Ser Val Ile His Ala Met Tyr Leu Gln Ile Arg His Ala Thr
        260                 265                 270

Val Asn Val Leu Trp Asn Lys Thr Pro Leu Lys His Glu Thr Leu Gln
    275                 280                 285

Ala Leu Ala Leu Leu Ala Leu Trp Pro Thr Ala Val Gln Lys Glu Thr
290                 295                 300

Pro Met Asp Ser Trp Leu Leu Ser Gly Ile Ser Ile Asn His Ala Ile
305                 310                 315                 320

Ile Ser Phe Asp Phe Leu Asn His Ala Pro Ser Asp Leu Ile Val Asp
            325                 330                 335

Asn Asp Met Val Ala Lys Leu Arg Val Trp Asn Ala Leu Cys Leu Thr
        340                 345                 350

Gln Leu Gln Ser Ala Ile Gly Asn Ala Arg Pro Phe His Ile Gln Gln
    355                 360                 365

Arg Tyr Leu Glu His Cys Pro Arg Leu Leu Glu His Pro Ala Ala Thr
370                 375                 380

Phe Glu Asp Gly Lys Ile Val Ala Glu Ile Gln Leu Tyr Leu Ile Ala
385                 390                 395                 400

Leu Lys Leu Gln Asn Phe Ser His Arg Met Arg Leu Gly Asp Phe Glu
            405                 410                 415

Tyr Glu Glu Ile Glu Arg Trp Lys Met Glu Trp Ala His Leu Leu Thr
        420                 425                 430

Gly Glu Gln His Ser Thr Leu Glu Leu Ser Leu Trp Tyr Cys Gln Leu
    435                 440                 445

Leu Leu Tyr Arg Thr Ala Met Arg Phe His Trp Glu Ser Glu His Leu
450                 455                 460

Ile Ser Glu Ile Leu Arg Asn Ser Arg Leu Ile Leu Ser Lys Phe Leu
465                 470                 475                 480

Leu Val Arg Phe Pro Asn Ala Leu Ala Phe Pro Asp Gln Ile Tyr Tyr
            485                 490                 495

Ile Val Gly Tyr Ala Ala Leu Asn Leu Cys Asp Phe Ser Pro Met Asp
        500                 505                 510

Pro Leu Ile Asp Gln Val Gln Thr Phe Leu Leu His Leu Ser Pro Asn
    515                 520                 525

Glu Asp His Ile Ala Tyr Arg Phe Ser Tyr Thr Ile Thr Glu Leu Lys
530                 535                 540

Arg Arg Cys Ala Thr Gly Pro Asn Pro His Asn Val Val Lys Gly Ala
545                 550                 555                 560

Phe Gly Asp Thr Arg Lys Leu Ser Met Gly Gln Gln Ile Pro Phe Met
            565                 570                 575
```

```
Asn Pro Leu Met Asp Thr Met Met Gly Glu Tyr Gly Gly Leu Glu His
        580                 585                 590

Leu Ile Pro Glu Val Pro Pro Asn Ser Leu Pro Asp Met Leu Thr Ser
        595                 600                 605

Val Ala Gly Glu Leu Gln Ala Phe Arg Thr Ala Ile Leu
        610                 615                 620

<210> SEQ ID NO 19
<211> LENGTH: 3000
<212> TYPE: DNA
<213> ORGANISM: Penicillium chrysogenum
<220> FEATURE:
<221> NAME/KEY: exon
<222> LOCATION: (575)..(792)
<220> FEATURE:
<221> NAME/KEY: Intron
<222> LOCATION: (793)..(890)
<220> FEATURE:
<221> NAME/KEY: exon
<222> LOCATION: (891)..(1283)
<220> FEATURE:
<221> NAME/KEY: Intron
<222> LOCATION: (1284)..(1336)
<220> FEATURE:
<221> NAME/KEY: exon
<222> LOCATION: (1337)..(1750)
<220> FEATURE:
<221> NAME/KEY: Intron
<222> LOCATION: (1751)..(1803)
<220> FEATURE:
<221> NAME/KEY: exon
<222> LOCATION: (1804)..(2033)
<220> FEATURE:
<221> NAME/KEY: Intron
<222> LOCATION: (2034)..(2102)
<220> FEATURE:
<221> NAME/KEY: exon
<222> LOCATION: (2103)..(2761)

<400> SEQUENCE: 19
taagacaaac tagtcaagaa tcaaacgaaa aaggatgtac ctagtataga tcgcgccact    60 cagcccctc aaacccctc tcctacggtt ttcgtcgggg aaatcggctc aggggggtag     120
ttaatacgac attatcaacc cctcttgaaa gtatgcaccg acaatcgcta cctttctaga   180
agccaacggg aagttgtcgg attggtggat gcatattcga ttaccccagg tccgccatgg   240
tccgctataa tccgccatga acaggatatg tatgttgtac ctgcgcggac gcttcgatat   300
cgtcagtaat cggtttcttg tcgcaattgg ctcaatctcc tcaccagcc  tagtggccct   360 aatgacccgc tattataagg cttggatctc cctgatagac atgagatgat cttcaggttg   420
tttgatttgg tctttgctta agggtctaat tgttgatcag cctttccttc ctatttccca   480
acttctcaac cttcccggtc gatcaggcat agacgatccc ctaaacagta catacctcca   540
gtacacttac agtaaccatt caacctccga taca atg acg aga act ggc cct cca   595
                                    Met Thr Arg Thr Gly Pro Pro
                                     1               5 att aat cct atc tcg tgg gac acc aag act att gtt cca gat gat ggc    643
Ile Asn Pro Ile Ser Trp Asp Thr Lys Thr Ile Val Pro Asp Asp Gly
         10                  15                  20 agc aga atc gat tcg gtc gct tgc cag gat gcg agg cca aaa ggg cgc    691
Ser Arg Ile Asp Ser Val Ala Cys Gln Asp Ala Arg Pro Lys Gly Arg
     25                  30                  35 atc cga cga tca atg act gct tgt cat acc tgt cgc aag ctc aag act    739
Ile Arg Arg Ser Met Thr Ala Cys His Thr Cys Arg Lys Leu Lys Thr
 40                  45                  50                  55 cgc tgt gat gtt gat ccc cgt ggt cat tct tgc cgt cgc tgt ttg tca    787
```

```
                    Arg Cys Asp Val Asp Pro Arg Gly His Ser Cys Arg Arg Cys Leu Ser
                                    60                  65                  70 ctt ag  gttggtttcg ccttttttatt catgtgtttg acatatcccc gattttttact              842
Leu Arg cttttttgaag tctcccgttt ctctatatgc tgactattgt cataaaaag g ctt gac              897
                                                         Leu Asp
                                                             75 tgc gag ctc ccc gag aca aca gag cgg ttc cag gac aat gca tca acc              945
Cys Glu Leu Pro Glu Thr Thr Glu Arg Phe Gln Asp Asn Ala Ser Thr
                80                  85                  90 tgg tct gac gcc acc gct gta ccc tcg att gag gaa cgg ctc gtc tct              993
Trp Ser Asp Ala Thr Ala Val Pro Ser Ile Glu Glu Arg Leu Val Ser
                95                  100                 105 ctc gaa cga gga atg ggg gag atg ata cat ctg atg cgg cag ata gtg             1041
Leu Glu Arg Gly Met Gly Glu Met Ile His Leu Met Arg Gln Ile Val
            110                 115                 120 aaa agc tcc ccc agc atg ccc tgc agc cca acc ttc caa act aga aac             1089
Lys Ser Ser Pro Ser Met Pro Cys Ser Pro Thr Phe Gln Thr Arg Asn
            125                 130                 135 cac agc ata gat gga aca tct tca agt gat agc atg tcc tca tct ttc             1137
His Ser Ile Asp Gly Thr Ser Ser Ser Asp Ser Met Ser Ser Ser Phe
140                 145                 150                 155 tat ccg ctc aag cca gcg cag ctc att cgg gac ctg caa gcc gaa tgc             1185
Tyr Pro Leu Lys Pro Ala Gln Leu Ile Arg Asp Leu Gln Ala Glu Cys
                160                 165                 170 ttc ggc gag aga gct cac ttc tcc gat gct gac atc ctc ggg gat atc             1233
Phe Gly Glu Arg Ala His Phe Ser Asp Ala Asp Ile Leu Gly Asp Ile
                175                 180                 185 gtc acc cag ggc atc gta gat tcc aag ctt tcc gtg aag ctg att gaa             1281
Val Thr Gln Gly Ile Val Asp Ser Lys Leu Ser Val Lys Leu Ile Glu
            190                 195                 200 ct  gtgtctga ttgtgtgtct gtcactggat cgccctgcta atgatctcgc cag t              1337
Leu ttt gtc gaa cat ttc ggc cac tgg gtc tca ata aat cac tcg tcc agc             1385
Phe Val Glu His Phe Gly His Trp Val Ser Ile Asn His Ser Ser Ser
205                 210                 215                 220 ctt caa cgg tcg aat aca ctc ctt ttc aat act gca tgt ctc ctg gct             1433
Leu Gln Arg Ser Asn Thr Leu Leu Phe Asn Thr Ala Cys Leu Leu Ala
                225                 230                 235 tcg cgc tat atg cct ggc cta cca caa cac act gtc cgc gat atc tca             1481
Ser Arg Tyr Met Pro Gly Leu Pro Gln His Thr Val Arg Asp Ile Ser
                240                 245                 250 ctc tat gta caa cat gcc gtc gcg aag gtg ttg tgg aag ccc ccg ccc             1529
Leu Tyr Val Gln His Ala Val Ala Lys Val Leu Trp Lys Pro Pro Pro
            255                 260                 265 atg aca agc gat atg ctg cag gcc ttg acc ttg ctt tgt ctc tat tcc             1577
Met Thr Ser Asp Met Leu Gln Ala Leu Thr Leu Leu Cys Leu Tyr Ser
        270                 275                 280 act tct att cac aaa gaa ggc ctg atg gac gac tgg ttg ctg agc ggg             1625
Thr Ser Ile His Lys Glu Gly Leu Met Asp Asp Trp Leu Leu Ser Gly
285                 290                 295                 300 atc tcg atc aac cat gcc ctc atc tct ttt aac ttt ctc aat act ttg             1673
Ile Ser Ile Asn His Ala Leu Ile Ser Phe Asn Phe Leu Asn Thr Leu
                305                 310                 315 cca gga gac aat tta agt cca gac gaa ctc ctt gct cag ttg cgt ttg             1721
Pro Gly Asp Asn Leu Ser Pro Asp Glu Leu Leu Ala Gln Leu Arg Leu
                320                 325                 330 tgg aat aca ctc tgt gca acc caa cta ca gtatgtcctg cccaacaatt               1770
Trp Asn Thr Leu Cys Ala Thr Gln Leu His
335                 340
```

```
cgtcaggtat acaatctaac accaatccaa cag c tcc gcc ctc gca aac ggc    1822
                                      Ser Ala Leu Ala Asn Gly
                                                      345 cgc act gtc aac atc caa caa caa tac atc aac caa tgt ccc cgc atc    1870
Arg Thr Val Asn Ile Gln Gln Gln Tyr Ile Asn Gln Cys Pro Arg Ile
350                 355                 360 cta gag cat gca ggt gcc aca cca gaa gac gga aga atc gtc gca gag    1918
Leu Glu His Ala Gly Ala Thr Pro Glu Asp Gly Arg Ile Val Ala Glu
365                 370                 375                 380 att caa cta tac cgc atc gcc ctc cga ctc caa cac agc cag agc cgc    1966
Ile Gln Leu Tyr Arg Ile Ala Leu Arg Leu Gln His Ser Gln Ser Arg
                385                 390                 395 ctc caa ttt gca gaa tct gaa tac gaa gaa ctg gag cgc tgg aga atg    2014
Leu Gln Phe Ala Glu Ser Glu Tyr Glu Glu Leu Glu Arg Trp Arg Met
            400                 405                 410 gag tgg gca cat ctc cta a gtacatcaac cctcccctat atgcccagcc         2063
Glu Trp Ala His Leu Leu
                415 actgcaatcc caatccaaat ctaacagcga cacccacag cc  acc aac gga gac     2116
                                              Thr Asn Gly Asp
                                                          420 tca act ctc aac cta aac ctc tgg ttc tgc caa ctc ctc cta cac cga    2164
Ser Thr Leu Asn Leu Asn Leu Trp Phe Cys Gln Leu Leu Leu His Arg
425                 430                 435 acc gcc gcg cgc ctc caa cca gac agc gag cgc ctc ctc cca gaa ata    2212
Thr Ala Ala Arg Leu Gln Pro Asp Ser Glu Arg Leu Leu Pro Glu Ile
440                 445                 450                 455 tgc ggc acc gcc cgc cta ata ata acc caa ttc ctt caa acg cgc ttc    2260
Cys Gly Thr Ala Arg Leu Ile Ile Thr Gln Phe Leu Gln Thr Arg Phe
                460                 465                 470 acg tcc gca ccc gct cta atc gac cac gtc tac ttc atc gtc ggc tac    2308
Thr Ser Ala Pro Ala Leu Ile Asp His Val Tyr Phe Ile Val Gly Tyr
            475                 480                 485 gcc gcg ctc aca ctc tgc gac tac acg ctc acc gac cca tta atc aac    2356
Ala Ala Leu Thr Leu Cys Asp Tyr Thr Leu Thr Asp Pro Leu Ile Asn
        490                 495                 500 caa gtg cgc ggc ttc cta ctg cac ctc gcg cca ggc ggc gac aac ctc    2404
Gln Val Arg Gly Phe Leu Leu His Leu Ala Pro Gly Gly Asp Asn Leu
505                 510                 515 tcc tac cgg atc gcg tgt att gtc ggc gaa gtg cag cgg cgc tac tca    2452
Ser Tyr Arg Ile Ala Cys Ile Val Gly Glu Val Gln Arg Arg Tyr Ser
520                 525                 530                 535 gag gcg act gct gtt gtg gcg gcg ggg tcg cat tcg tcg tcg ccg gtt    2500
Glu Ala Thr Ala Val Val Ala Ala Gly Ser His Ser Ser Ser Pro Val
                540                 545                 550 gcc gag gtc aag ggc gcg cag atg ttc ggt tca tcg cac cat cat cgt    2548
Ala Glu Val Lys Gly Ala Gln Met Phe Gly Ser Ser His His His Arg
            555                 560                 565 acc ggt atg gag ctc tcg cag ctg atg tct agc ccc gag ggc ttg gat    2596
Thr Gly Met Glu Leu Ser Gln Leu Met Ser Ser Pro Glu Gly Leu Asp
        570                 575                 580 tcc ctt gtt gag gga tat aat tgt ctt gag cag atg atg cct ggg tat    2644
Ser Leu Val Glu Gly Tyr Asn Cys Leu Glu Gln Met Met Pro Gly Tyr
585                 590                 595 gcg gct tcg cag cct gca ttt gag gcg ccg gat ttg ttt cat cat tct    2692
Ala Ala Ser Gln Pro Ala Phe Glu Ala Pro Asp Leu Phe His His Ser
600                 605                 610                 615 cct acg act ggt gtt act ggt ggg gct atg cct att ggt ctc gtg ccc    2740
Pro Thr Thr Gly Val Thr Gly Gly Ala Met Pro Ile Gly Leu Val Pro
                620                 625                 630
```

```
agg gct ttg cat gat tgg tga tgaggttatg ggttggtctt ttggttctag    2791
Arg Ala Leu His Asp Trp
            635 attattggag ttggtgcatg ttgaactaat accgaggttg gatttgggat ttgggtgttg    2851 tgttatgttt cttttttactt gaggatcgta ataacaaaag tacaaatgga aatttgtcct    2911 gacttcttca actggcttct ctgtttcgtg ttgctattca tcaaagtaat atatattacc    2971 tatagctgga ttcaaattgt attaccttg                                      3000

<210> SEQ ID NO 20
<211> LENGTH: 1914
<212> TYPE: DNA
<213> ORGANISM: Penicillium chrysogenum
<220> FEATURE:
<221> NAME/KEY: exon
<222> LOCATION: (1)..(218)
<220> FEATURE:
<221> NAME/KEY: exon
<222> LOCATION: (219)..(611)
<220> FEATURE:
<221> NAME/KEY: exon
<222> LOCATION: (612)..(1025)
<220> FEATURE:
<221> NAME/KEY: exon
<222> LOCATION: (1026)..(1255)
<220> FEATURE:
<221> NAME/KEY: exon
<222> LOCATION: (1256)..(1914)

<400> SEQUENCE: 20 atg acg aga act ggc cct cca att aat cct atc tcg tgg gac acc aag     48
Met Thr Arg Thr Gly Pro Pro Ile Asn Pro Ile Ser Trp Asp Thr Lys
1               5                   10                  15 act att gtt cca gat gat ggc agc aga atc gat tcg gtc gct tgc cag    96
Thr Ile Val Pro Asp Asp Gly Ser Arg Ile Asp Ser Val Ala Cys Gln
                20                  25                  30 gat gcg agg cca aaa ggg cgc atc cga cga tca atg act gct tgt cat   144
Asp Ala Arg Pro Lys Gly Arg Ile Arg Arg Ser Met Thr Ala Cys His
            35                  40                  45 acc tgt cgc aag ctc aag act cgc tgt gat gtt gat ccc cgt ggt cat   192
Thr Cys Arg Lys Leu Lys Thr Arg Cys Asp Val Asp Pro Arg Gly His
        50                  55                  60 tct tgc cgt cgc tgt ttg tca ctt ag g ctt gac tgc gag ctc ccc gag   240
Ser Cys Arg Arg Cys Leu Ser Leu Arg   Leu Asp Cys Glu Leu Pro Glu
65                  70                  75                  80 aca aca gag cgg ttc cag gac aat gca tca acc tgg tct gac gcc acc   288
Thr Thr Glu Arg Phe Gln Asp Asn Ala Ser Thr Trp Ser Asp Ala Thr
                85                  90                  95 gct gta ccc tcg att gag gaa cgg ctc gtc tct ctc gaa cga gga atg   336
Ala Val Pro Ser Ile Glu Glu Arg Leu Val Ser Leu Glu Arg Gly Met
                100                 105                 110 ggg gag atg ata cat ctg atg cgg cag ata gtg aaa agc tcc ccc agc   384
Gly Glu Met Ile His Leu Met Arg Gln Ile Val Lys Ser Ser Pro Ser
            115                 120                 125 atg ccc tgc agc cca acc ttc caa act aga aac cac agc ata gat gga   432
Met Pro Cys Ser Pro Thr Phe Gln Thr Arg Asn His Ser Ile Asp Gly
        130                 135                 140 aca tct tca agt gat agc atg tcc tca tct ttc tat ccg ctc aag cca   480
Thr Ser Ser Ser Asp Ser Met Ser Ser Ser Phe Tyr Pro Leu Lys Pro
145                 150                 155                 160 gcg cag ctc att cgg gac ctg caa gcc gaa tgc ttc ggc gag aga gct   528
Ala Gln Leu Ile Arg Asp Leu Gln Ala Glu Cys Phe Gly Glu Arg Ala
                165                 170                 175
```

```
cac ttc tcc gat gct gac atc ctc ggg gat atc gtc acc cag ggc atc      576
His Phe Ser Asp Ala Asp Ile Leu Gly Asp Ile Val Thr Gln Gly Ile
            180                 185                 190 gta gat tcc aag ctt tcc gtg aag ctg att gaa ct  t ttt gtc gaa cat    624
Val Asp Ser Lys Leu Ser Val Lys Leu Ile Glu Leu   Phe Val Glu His
        195                 200                 205 ttc ggc cac tgg gtc tca ata aat cac tcg tcc agc ctt caa cgg tcg      672
Phe Gly His Trp Val Ser Ile Asn His Ser Ser Ser Leu Gln Arg Ser
        210                 215                 220 aat aca ctc ctt ttc aat act gca tgt ctc ctg gct tcg cgc tat atg      720
Asn Thr Leu Leu Phe Asn Thr Ala Cys Leu Leu Ala Ser Arg Tyr Met
225                 230                 235                 240 cct ggc cta cca caa cac act gtc cgc gat atc tca ctc tat gta caa      768
Pro Gly Leu Pro Gln His Thr Val Arg Asp Ile Ser Leu Tyr Val Gln
                245                 250                 255 cat gcc gtc gcg aag gtg ttg tgg aag ccc ccg ccc atg aca agc gat      816
His Ala Val Ala Lys Val Leu Trp Lys Pro Pro Pro Met Thr Ser Asp
            260                 265                 270 atg ctg cag gcc ttg acc ttg ctt tgt ctc tat tcc act tct att cac      864
Met Leu Gln Ala Leu Thr Leu Leu Cys Leu Tyr Ser Thr Ser Ile His
        275                 280                 285 aaa gaa ggc ctg atg gac gac tgg ttg ctg agc ggg atc tcg atc aac      912
Lys Glu Gly Leu Met Asp Asp Trp Leu Leu Ser Gly Ile Ser Ile Asn
        290                 295                 300 cat gcc ctc atc tct ttt aac ttt ctc aat act ttg cca gga gac aat      960
His Ala Leu Ile Ser Phe Asn Phe Leu Asn Thr Leu Pro Gly Asp Asn
305                 310                 315                 320 tta agt cca gac gaa ctc ctt gct cag ttg cgt ttg tgg aat aca ctc     1008
Leu Ser Pro Asp Glu Leu Leu Ala Gln Leu Arg Leu Trp Asn Thr Leu
                325                 330                 335 tgt gca acc caa cta ca  c tcc gcc ctc gca aac ggc cgc act gtc aac   1056
Cys Ala Thr Gln Leu His     Ser Ala Leu Ala Asn Gly Arg Thr Val Asn
            340                 345                 350 atc caa caa caa tac atc aac caa tgt ccc cgc atc cta gag cat gca     1104
Ile Gln Gln Gln Tyr Ile Asn Gln Cys Pro Arg Ile Leu Glu His Ala
        355                 360                 365 ggt gcc aca cca gaa gac gga aga atc gtc gca gag att caa cta tac     1152
Gly Ala Thr Pro Glu Asp Gly Arg Ile Val Ala Glu Ile Gln Leu Tyr
370                 375                 380 cgc atc gcc ctc cga ctc caa cac agc cag agc cgc ctc caa ttt gca     1200
Arg Ile Ala Leu Arg Leu Gln His Ser Gln Ser Arg Leu Gln Phe Ala
385                 390                 395                 400 gaa tct gaa tac gaa gaa ctg gag cgc tgg aga atg gag tgg gca cat     1248
Glu Ser Glu Tyr Glu Glu Leu Glu Arg Trp Arg Met Glu Trp Ala His
                405                 410                 415 ctc cta a cc  acc aac gga gac tca act ctc aac cta aac ctc tgg ttc   1296
Leu Leu     Thr Thr Asn Gly Asp Ser Thr Leu Asn Leu Asn Leu Trp Phe
            420                 425                 430 tgc caa ctc ctc cta cac cga acc gcc gcg cgc ctc caa cca gac agc     1344
Cys Gln Leu Leu Leu His Arg Thr Ala Ala Arg Leu Gln Pro Asp Ser
        435                 440                 445 gag cgc ctc ctc cca gaa ata tgc ggc acc gcc cgc tta ata ata acc     1392
Glu Arg Leu Leu Pro Glu Ile Cys Gly Thr Ala Arg Leu Ile Ile Thr
        450                 455                 460 caa ttc ctt caa acg cgc ttc acg tcc gca ccc gct cta atc gac cac     1440
Gln Phe Leu Gln Thr Arg Phe Thr Ser Ala Pro Ala Leu Ile Asp His
465                 470                 475                 480 gtc tac ttc atc gtc ggc tac gcc gcg ctc aca ctc tgc gac tac acg     1488
Val Tyr Phe Ile Val Gly Tyr Ala Ala Leu Thr Leu Cys Asp Tyr Thr
                485                 490                 495
```

```
ctc acc gac cca tta atc aac caa gtg cgc ggc ttc cta ctg cac ctc      1536
Leu Thr Asp Pro Leu Ile Asn Gln Val Arg Gly Phe Leu Leu His Leu
            500                 505                 510 gcg cca ggc ggc gac aac ctc tcc tac cgg atc gcg tgt att gtc ggc      1584
Ala Pro Gly Gly Asp Asn Leu Ser Tyr Arg Ile Ala Cys Ile Val Gly
        515                 520                 525 gaa gtg cag cgg cgc tac tca gag gcg act gct gtt gtg gcg gcg ggg      1632
Glu Val Gln Arg Arg Tyr Ser Glu Ala Thr Ala Val Val Ala Ala Gly
    530                 535                 540 tcg cat tcg tcg tcg ccg gtt gcc gag gtc aag ggc gcg cag atg ttc      1680
Ser His Ser Ser Ser Pro Val Ala Glu Val Lys Gly Ala Gln Met Phe
545                 550                 555                 560 ggt tca tcg cac cat cat cgt acc ggt atg gag ctc tcg cag ctg atg      1728
Gly Ser Ser His His His Arg Thr Gly Met Glu Leu Ser Gln Leu Met
                565                 570                 575 tct agc ccc gag ggc ttg gat tcc ctt gtt gag gga tat aat tgt ctt      1776
Ser Ser Pro Glu Gly Leu Asp Ser Leu Val Glu Gly Tyr Asn Cys Leu
            580                 585                 590 gag cag atg atg cct ggg tat gcg gct tcg cag cct gca ttt gag gcg      1824
Glu Gln Met Met Pro Gly Tyr Ala Ala Ser Gln Pro Ala Phe Glu Ala
        595                 600                 605 ccg gat ttg ttt cat cat tct cct acg act ggt gtt act ggt ggg gct      1872
Pro Asp Leu Phe His His Ser Pro Thr Thr Gly Val Thr Gly Gly Ala
    610                 615                 620 atg cct att ggt ctc gtg ccc agg gct ttg cat gat tgg tga              1914
Met Pro Ile Gly Leu Val Pro Arg Ala Leu His Asp Trp
625                 630                 635

<210> SEQ ID NO 21
<211> LENGTH: 637
<212> TYPE: PRT
<213> ORGANISM: Penicillium chrysogenum

<400> SEQUENCE: 21

Met Thr Arg Thr Gly Pro Pro Ile Asn Pro Ile Ser Trp Asp Thr Lys
1               5                   10                  15

Thr Ile Val Pro Asp Asp Gly Ser Arg Ile Asp Ser Val Ala Cys Gln
            20                  25                  30

Asp Ala Arg Pro Lys Gly Arg Ile Arg Arg Ser Met Thr Ala Cys His
        35                  40                  45

Thr Cys Arg Lys Leu Lys Thr Arg Cys Asp Val Asp Pro Arg Gly His
    50                  55                  60

Ser Cys Arg Arg Cys Leu Ser Leu Arg Leu Asp Cys Glu Leu Pro Glu
65                  70                  75                  80

Thr Thr Glu Arg Phe Gln Asp Asn Ala Ser Thr Trp Ser Asp Ala Thr
                85                  90                  95

Ala Val Pro Ser Ile Glu Glu Arg Leu Val Ser Leu Glu Arg Gly Met
            100                 105                 110

Gly Glu Met Ile His Leu Met Arg Gln Ile Val Lys Ser Ser Pro Ser
        115                 120                 125

Met Pro Cys Ser Pro Thr Phe Gln Thr Arg Asn His Ser Ile Asp Gly
    130                 135                 140

Thr Ser Ser Ser Asp Ser Met Ser Ser Phe Tyr Pro Leu Lys Pro
145                 150                 155                 160

Ala Gln Leu Ile Arg Asp Leu Gln Ala Glu Cys Phe Gly Glu Arg Ala
                165                 170                 175

His Phe Ser Asp Ala Asp Ile Leu Gly Asp Ile Val Thr Gln Gly Ile
            180                 185                 190
```

```
Val Asp Ser Lys Leu Ser Val Lys Leu Ile Glu Leu Phe Val Glu His
    195                 200                 205

Phe Gly His Trp Val Ser Ile Asn His Ser Ser Ser Leu Gln Arg Ser
210                 215                 220

Asn Thr Leu Leu Phe Asn Thr Ala Cys Leu Leu Ala Ser Arg Tyr Met
225                 230                 235                 240

Pro Gly Leu Pro Gln His Thr Val Arg Asp Ile Ser Leu Tyr Val Gln
                245                 250                 255

His Ala Val Ala Lys Val Leu Trp Lys Pro Pro Met Thr Ser Asp
            260                 265                 270

Met Leu Gln Ala Leu Thr Leu Leu Cys Leu Tyr Ser Thr Ser Ile His
        275                 280                 285

Lys Glu Gly Leu Met Asp Asp Trp Leu Leu Ser Gly Ile Ser Ile Asn
290                 295                 300

His Ala Leu Ile Ser Phe Asn Phe Leu Asn Thr Leu Pro Gly Asp Asn
305                 310                 315                 320

Leu Ser Pro Asp Glu Leu Leu Ala Gln Leu Arg Leu Trp Asn Thr Leu
                325                 330                 335

Cys Ala Thr Gln Leu His Ser Ala Leu Ala Asn Gly Arg Thr Val Asn
            340                 345                 350

Ile Gln Gln Gln Tyr Ile Asn Gln Cys Pro Arg Ile Leu Glu His Ala
        355                 360                 365

Gly Ala Thr Pro Glu Asp Gly Arg Ile Val Ala Glu Ile Gln Leu Tyr
370                 375                 380

Arg Ile Ala Leu Arg Leu Gln His Ser Gln Ser Arg Leu Gln Phe Ala
385                 390                 395                 400

Glu Ser Glu Tyr Glu Glu Leu Glu Arg Trp Arg Met Glu Trp Ala His
                405                 410                 415

Leu Leu Thr Thr Asn Gly Asp Ser Thr Leu Asn Leu Asn Leu Trp Phe
            420                 425                 430

Cys Gln Leu Leu Leu His Arg Thr Ala Ala Arg Leu Gln Pro Asp Ser
        435                 440                 445

Glu Arg Leu Leu Pro Glu Ile Cys Gly Thr Ala Arg Leu Ile Ile Thr
450                 455                 460

Gln Phe Leu Gln Thr Arg Phe Thr Ser Ala Pro Ala Leu Ile Asp His
465                 470                 475                 480

Val Tyr Phe Ile Val Gly Tyr Ala Ala Leu Thr Leu Cys Asp Tyr Thr
                485                 490                 495

Leu Thr Asp Pro Leu Ile Asn Gln Val Arg Gly Phe Leu Leu His Leu
            500                 505                 510

Ala Pro Gly Gly Asp Asn Leu Ser Tyr Arg Ile Ala Cys Ile Val Gly
        515                 520                 525

Glu Val Gln Arg Arg Tyr Ser Glu Ala Thr Ala Val Val Ala Ala Gly
530                 535                 540

Ser His Ser Ser Ser Pro Val Ala Glu Val Lys Gly Ala Gln Met Phe
545                 550                 555                 560

Gly Ser Ser His His Arg Thr Gly Met Glu Leu Ser Gln Leu Met
                565                 570                 575

Ser Ser Pro Glu Gly Leu Asp Ser Leu Val Glu Gly Tyr Asn Cys Leu
            580                 585                 590

Glu Gln Met Met Pro Gly Tyr Ala Ala Ser Gln Pro Ala Phe Glu Ala
        595                 600                 605

Pro Asp Leu Phe His His Ser Pro Thr Thr Gly Val Thr Gly Gly Ala
610                 615                 620
```

```
Met Pro Ile Gly Leu Val Pro Arg Ala Leu His Asp Trp
625                 630                 635

<210> SEQ ID NO 22
<211> LENGTH: 12
<212> TYPE: PRT
<213> ORGANISM: Aspergillus niger

<400> SEQUENCE: 22

Glu Trp Ala His Leu Phe Ser Gly Glu Ser Ser Thr
1               5                   10

<210> SEQ ID NO 23
<211> LENGTH: 25
<212> TYPE: DNA
<213> ORGANISM: Artificial sequence
<220> FEATURE:
<223> OTHER INFORMATION: Oligonucleotide designed as PCR primer to
      generate a DNA fragment in the polymerase chain reaction

<400> SEQUENCE: 23
ctctgcagga attcaagcta gatgc                                           25

<210> SEQ ID NO 24
<211> LENGTH: 24
<212> TYPE: DNA
<213> ORGANISM: Artificial sequence
<220> FEATURE:
<223> OTHER INFORMATION: Oligonucleotide designed as PCR primer to
      generate a DNA fragment in the polymerase chain reaction

<400> SEQUENCE: 24
ttatgcacac ccactacata catg                                            24

<210> SEQ ID NO 25
<211> LENGTH: 42
<212> TYPE: PRT
<213> ORGANISM: Aspergillus oryzae
<220> FEATURE:
<221> NAME/KEY: ZN_FING
<222> LOCATION: (1)..(42)

<400> SEQUENCE: 25

Met Thr Ala Cys Asn Thr Cys Arg Lys Leu Lys Thr Arg Cys Asp Leu
1               5                   10                  15

Asp Pro Arg Gly His Ala Cys Arg Arg Cys Leu Ser Leu Arg Ile Asp
            20                  25                  30

Cys Gln Leu Pro Glu Thr Ser Glu Arg Phe
        35                  40

<210> SEQ ID NO 26
<211> LENGTH: 42
<212> TYPE: PRT
<213> ORGANISM: Aspergillus fumigatus
<220> FEATURE:
<221> NAME/KEY: ZN_FING
<222> LOCATION: (1)..(42)

<400> SEQUENCE: 26

Met Thr Ala Cys Asn Thr Cys Arg Lys Leu Lys Thr Arg Cys Asp Leu
1               5                   10                  15

Asp Pro Arg Gly His Ala Cys Arg Arg Cys Leu Ser Leu Arg Ile Glu
            20                  25                  30

Cys Lys Leu Pro Glu Thr Ala Glu Arg Phe
        35                  40
```

```
<210> SEQ ID NO 27
<211> LENGTH: 42
<212> TYPE: PRT
<213> ORGANISM: Penicillium chrysogenum
<220> FEATURE:
<221> NAME/KEY: ZN_FING
<222> LOCATION: (1)..(42)

<400> SEQUENCE: 27

Met Thr Ala Cys His Thr Cys Arg Lys Leu Lys Thr Arg Cys Asp Val
 1               5                  10                  15

Asp Pro Arg Gly His Ser Cys Arg Arg Cys Leu Ser Leu Arg Leu Asp
            20                  25                  30

Cys Glu Leu Pro Glu Thr Thr Glu Arg Phe
            35                  40
```